(12) United States Patent
Rosemeyer et al.

(10) Patent No.: US 9,902,752 B2
(45) Date of Patent: Feb. 27, 2018

(54) 5-FLUOROURACIL DERIVATIVES

(71) Applicant: B. Braun Melsungen AG, Melsungen (DE)

(72) Inventors: Helmut Rosemeyer, Osnabrück (DE); Edith Malecki, Bad Zwischenahn (DE)

(73) Assignee: B. Braun Melsungen AG, Melsungen (DE)

( * ) Notice: Subject to any disclaimer, the term of this patent is extended or adjusted under 35 U.S.C. 154(b) by 62 days.

(21) Appl. No.: 14/417,860

(22) PCT Filed: Sep. 25, 2013

(86) PCT No.: PCT/EP2013/069981
§ 371 (c)(1),
(2) Date: Jan. 28, 2015

(87) PCT Pub. No.: WO2014/048998
PCT Pub. Date: Apr. 3, 2014

(65) Prior Publication Data
US 2015/0291649 A1    Oct. 15, 2015

(30) Foreign Application Priority Data

Sep. 28, 2012    (EP) .................................... 12186564

(51) Int. Cl.
*A01N 43/04* (2006.01)
*A61K 31/70* (2006.01)
(Continued)

(52) U.S. Cl.
CPC .................. *C07H 19/06* (2013.01)

(58) Field of Classification Search
CPC ..................................................... C07H 19/06
See application file for complete search history.

(56) References Cited

U.S. PATENT DOCUMENTS 7,378,401 B2    5/2008    Boehm et al.
7,816,516 B2    10/2010    Sommermeyer et al.

FOREIGN PATENT DOCUMENTS

EP    0 588 317 A1    3/1994
GB    2 168 350 A     6/1986
GB    2 168 353 A     6/1988

OTHER PUBLICATIONS

Abstract of Japanese Patent—JPS57128699, Aug. 10, 1982, 2 pages.

(Continued)

*Primary Examiner* — Lawrence E Crane
(74) *Attorney, Agent, or Firm* — Dority & Manning, P.A.

(57) ABSTRACT

The present invention is directed to a compound that can be used in the treatment of cancer. The compound is represented by formula (I)

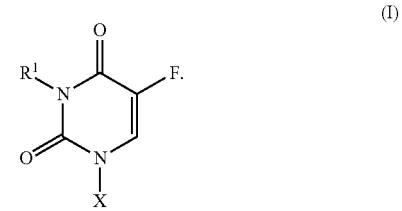

Further, X is

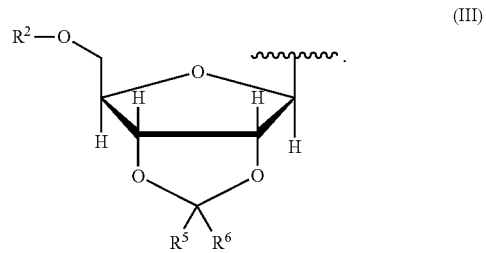

In addition, $R^1$ is selected from H,

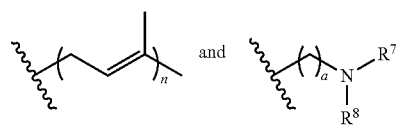

and
substituted or unsubstituted cyclic terpene moieties; $R^7$ and $R^8$ are independently selected from $C_1$ to $C_{30}$ alkyl; n is an integer ranging 1 to 4; and a is an integer ranging from 1 to 20. Moreover, $R^2$ is H; a Mono-phosphate, Di-phosphate, Tri-phosphate or phosphoamidite moiety; or —Y—$X^1$ or —Y-L-$Y^1$—$X^1$, where Y and $Y^1$ are independently from each other a single bond or a functional connecting moiety, $X^1$ is a colloid-active compound, a fluorescence marker, or a polynucleotide moiety having up to 50 nucleotide residues. L is a linker where Y and $X^1$ are covalently linked together; $R^5$ and $R^6$ represent independently from each other a $C_1$-$C_{28}$-alkyl moiety which may optionally be substituted/ interrupted by one or more heteroatom(s) and/or functional group(s); a $C_1$-$C_{28}$-alkyl moiety substituted with one or more moieties selected from the group —Y—$X^1$ or —Y-L-$Y^1$—$X^1$; form a ring having at least 5 members, wherein the ring may be substituted or interrupted by one or more hetero atom(s) and/or functional group(s); or $R^5$ and $R^6$ represent independently from each other —Y—$X^1$ or —Y-L-$Y^1$—$X^1$; with the provisos that $R^1$ and $R^2$ are not both H and the (Continued)

compound comprises at least two chains each of which having 4 or more carbon atoms.

5 Claims, 10 Drawing Sheets

(51) Int. Cl.
*C07H 19/00* (2006.01)
*C07H 19/06* (2006.01)

(56) References Cited

OTHER PUBLICATIONS

Abstract of Japanese Patent —JPH0597887, Apr. 20, 1993, 2 pages.
Abstract of Japanese Patent—JPH10218893, Aug. 18, 1998, 1 page.
Article—Crosasso et al., "Antitumoral Activity of Liposomes and Immunoliposomes Containing 5-Fluorouridine Prodrugs," *Journal of Pharmaceutical Sciences*, vol. 86, No. 7, Jul. 1997, pp. 832-839.
Article—Czuchajowski et al., "Porphyrinyl-Nucleosides Containing Fluorinated Nucleobases," *Tetrahedren Letters*, vol. 34, No. 34, 1993, pp. 5409-5412.
Article—Hanessian et al., "Synthesis of chemically functionalized superparamagnetic nanoparticles as delivery vectors for chemotheraputic drugs," *Bioorganic & Medicinal Chemistry*, vol. 16, 2008, pp. 2921-2931.
Article—Heidelberger et al., "Fluorinated Pyrimidines VI Effects of 5-Fluorouridine and 5-Fluoro-2'-Deoxyuridine on Transplanted Tumors," *P.S.E.B.M.*, vol. 97, Dec. 1957, pp. 470-475.
Article—Im et al., "A Blood-brain Barrier Permeable Derivative of 5-Fluorouracil: Preparation, Intracellular Localization, and Mouse Tissue Distribution," *Bull. Korean Chem. Soc.*, vol. 32, No. 3, 2011, pp. 873-879.
Article—Luo et al., "A novel 5-fluorouracil prodrug using hydroxyethyl starch as a macromolecular carrier for sustained release," *Carbohydrate Polymers*, vol. 87, 2012, pp. 2642-2647.
Article—Malecki et al., "O-2',3'-Ketal-Nucleolipids of the Cytostatic t-Fluorouridine: Synthesis, Lipophilicity, and Acidic Stability," *Helvetica Chimica Acta*, vol. 93, 2010, pp. 1500-1512.
Article—Malecki et al., "Synthesis and Crystal Structures of O-2',3'-Cyclic Cyclopentanone and Cyclohexanone Ketals of the Cytostatic 5-Fluorouridine," *Helvetica Chimica Acta*, vol. 92, 2009, pp. 1923-1932.
Article—Suda et al., "Inhibition of Experimental Pulmonary Metastasis of Mouse Colon Adenocarcinoma 26 Sublines by a Sialic Acid: Nucleoside Conjugate having Sialyltransferase Inhibiting Activity," *Cancer Research*, vol. 46, Feb. 1986, pp. 858-862.
Article—Werz et al., "Specific DNA Duplex Formation of an Artificial Lipid Bilayer: towards a New DNA Biosensor Technology," *Chemistry & Biodiversity*, vol. 9, 2012, pp. 272-281.
Article—Yamada et al., "In vitro study on the intrathecal use of 5-fluoro-2'-deoxyuridine (FdUrd) for meningeal dissemination of malignant brain tumors," *Journal of Neuro-Oncology*, Vol. 37, 1998, pp. 115-121.
Part of Book—*Selective Toxicity*—The physic-chemical basis of therapy, Adrien Albert, Seventh Edition, 1985, pp. 125-126.
International Search Report for PCT/EP2013/069981 dated Oct. 28, 2013, 5 pages.

Fig.15-1
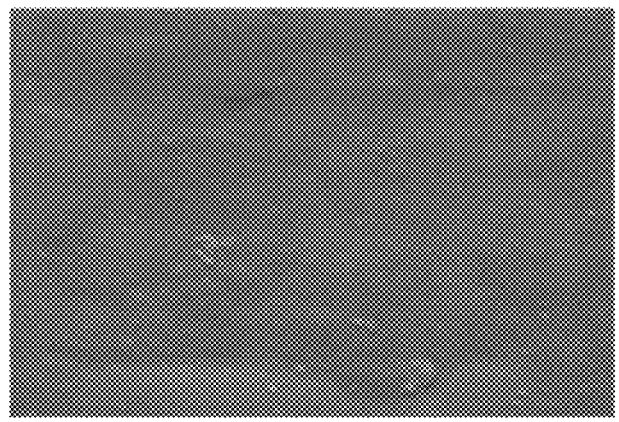
1μm  Fig.15-2
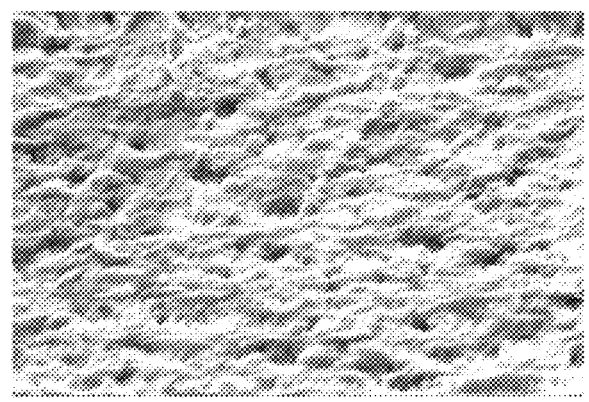
250μm  Fig.16

5-FLUOROURACIL DERIVATIVES

CROSS REFERENCE TO RELATED APPLICATIONS

This application is the national stage entry of International Patent Application No. PCT/EP2013/069981 having a filing date of Sep. 25, 2013, which claims priority to and the benefit of European Patent Application No. 12186564.6 filed in the European Patent Office on Sep. 28, 2012, the entire contents of which are incorporated herein by reference.

The present invention relates to 5-fluorouracil derivatives represented by formula (I), pharmaceutical compositions comprising said derivative and their use in the treatment of cancer as well as a process for preparing the 5-fluorouracil derivative represented by formula (I).

GB 2 168 353 and GB 2 168 350 describe a steroid which is connected to a 5-fluorouracil base via a 5'-monophosphate moiety.

JP 05097887 describes 2'-deoxy-β-D-ribunucleosides of 5-fluorouracil derivatives carrying an amino acid moiety as well as a method for the production of the same.

JP 57128699 describes pharmacological active 5-fluorouracil β-D-ribonucleoside derivatives carrying a mono-phosphate ester moiety.

JP 10218893 describes the preparation of oligonucleodites having a 5-fluorouracil moiety being linked to cyanophosphoramidite.

However, none of the above mentioned citations describe compounds comprising at least two carbon chains each of which having 4 or more carbons that are linearly-linked as described in the present invention.

The fluorinated analogue of uracil, fluorouracil (5-fluorouracil, 5-Fluoruracil-Biosyn®, Fluoruracil-GRY®, 5-FU HEXAL®, 5-FU Lederle® etc.) is one of the oldest tumor antimetabolites. It has been developed in the 1950's. Since then, fluorouracil has been employed for the treatment of various solid tumors, such as prostate, pancreatic, colon, rectum, breast, liver, head, neck and bladder carcinomas. In the cell, fluorouracil is converted to the active nucleotides 5-fluoro-2'-deoxyuridine 5'-monophosphate (5-FdUMP), 5-fluorouridine 5'-triphosphate (5-FUTP) and 5-fluoro-2'-deoxyuridine 5'-triphosphate (5-FdUTP). The metabolism is very complex. Fluorouracil is first converted by phosphoribosyl transferase to 5-fluorouridine 5'-monophosphate (5-FUMP), which is phosphorylated by means of nucleotide kinases through the 5'-diphosphate (5-FUDP) to form the 5'-triphosphate (5-FUTP). The nucleotide 5-FUTP is incorporated by RNA polymerases into the RNA instead of UTP and thus interferes with the function of the RNA. The metabolite 5-FUDP is converted with the aid of ribonucleotide reductase to 5-FdUDP, which is then phosphorylated by nucleoside diphosphate kinase to form 5-FdUTP. 5-FdUTP may also be incorporated into DNA as a false building block by DNA polymerases. Removal of the wrong nucleotides by uracil glycosylase results in DNA single strand breaks, which leads to inhibition of DNA synthesis, DNA fragmentation and eventually apoptosis. Dephosphorylation of 5-FdUTP by means of dUTPase forms the third active metabolite 5-fluorodeoxyuridine monophosphate (5-FdUMP). It inhibits thymidylate synthase (TS), which catalyzes the reductive methylation of deoxyuridine monophosphate (dUMP) to deoxythymidine monophosphate (dTMP) together with the cofactor 5,10-methylenetetrahydrofolate. After binding of 5-FdUMP to TS, the enzyme is blocked in a tertiary complex (TS, 5-FdUMP and folate), whereby methylation at the C-5 is inhibited. This results in inhibition of DNA synthesis.

The deoxynucleoside floxuridine (5-fluoro-2'-deoxyuridine, 5-FUdR) is a prodrug of 5-fluorouracil. The bioactivation thereof is simpler because it is phosphorylated by thymidine kinase to the active metabolite 5-FdUMP. Floxuridine serves to treat metastatic colorectal carcinoma. Like fluorouracil, it has a very low oral bioavailability and is therefore administered as an intra-arterial injection. Since floxuridine actually has no advantage over 5-FU, it is used only rarely today. In the recent decades, orally applicable prodrugs of fluorouracil have been developed that also enable the drug to be selectively guided to the tumor cells. The fluorouracil prodrug doxifluridine (5'-deoxy-5-fluorouridine) is converted by thymidine phosphorylase (TP) to 5-fluorouracil (5-FU), which catalyzes the phosphorolysis of pyrimidine nucleosides. Since this enzyme is present in higher concentrations in the tumor as compared to normal cells, the drug exhibits a tumor-selective activity. However, upon oral administration, doxifluridine causes severe gastrointestinal toxicity (diarrhea), because 5-fluorouracil is released already in the gastro-intestinal tract. This is why doxifluridine cannot be employed clinically. The fluoropyrimidine carbamate capecitabin (N(4)-pentyloxycarbonyl-5'-deoxy-5-fluorocytidine, Xeloda®) is the first approved orally administered 5-fluorouracil prodrug. Because of its increased lipophilicity that is due to the pentyloxycarbonyl group, it is very quickly absorbed as a prodrug in the gastro-intestinal tract. Subsequently, it is metabolized in a three-step enzymatic process to form 5-fluorouracil. The side chain is cleaved off in the liver by a carboxyl esterase. Thereafter, the 5'-deoxy-5-fluorocytidine (5'-DFCR) formed is converted to 5'-deoxy-5-fluorouridine (5'-DFUR, doxifluridine), by means of cytidine deaminase in the liver and in the tumor. Because of the absence of the 5'-hydroxy group, this metabolite cannot be converted to fluorouracil nucleotides by nucleoside kinases. In the last activation step, the 5-fluorouracil is formed from 5'-DFUR by means of thymidine phosphorylase. The enzymes cytidine deaminase and thymidine phosphorylase are more abundant in many tumors (3-10 times increased concentrations). Therefore, the activation of capecitabine in tumor cells proceeds more effectively as compared to normal cells, which leads to selective enrichment of 5-fluorouracil in the tumor. Capecitabine is employed for the treatment of metastatic colorectal carcinoma. A better response rate as compared to 5-fluorouracil could be observed in clinical studies. Further, capecitabine is also employed in advanced or metastatic breast carcinoma. The patients are administered 1250 mg/m$^2$ of body surface area twice a day for two weeks, followed by one week of therapy break. The most frequent side effects include gastro-intestinal disorders and hand-foot syndrome (hand-foot skin reaction); myelosuppression occurs rarely. The tetrahydrofuryl derivative tegafur (ftorafur, 5-fluoro-1-(tetrahydro-2-furyl)uracil) is another orally applicable prodrug of 5-FU, developed as early as in the 1960's in the Soviet Union by S. Hiller. This medicament contains a racemic mixture of R and S isomers. Tegafur is metabolized by the cytochrome P450 system in the liver or by means of pyrimidine nucleoside phosphorylase to form 5-fluorouracil. However, because of its severe gastro-intestinal toxicity, cardio- and neurotoxicity, tegafur is used only in combination with uracil (UFT®) and dihydropyrimidine dehydrogenase inhibitors. The active form 5-fluorouracil is metabolized in the liver very quickly by saturating the double bond by means of dihydropyrimidine dehydrogenase (DPD) to form 5,6-dihdyro-5-fluorouracil, and is thus inactivated. UFT® contains tegafur and uracil in a molar ratio of 1:4. Uracil is a natural substrate of DPD and has a higher affinity for this enzyme than 5-fluorouracil has. It competitively inhibits DPD and thus slows down the degradation of 5-FU. The half life of fluorouracil is prolonged thereby (10-14 hours instead of 10-30 minutes), and its plasma level and bioavailability are significantly increased. The cofactor 5,10-methylene tetrahydrofolate is necessary for thymidilate synthase. Therefore, the cytotoxicity of fluorouracil and fluoropyrimidines can be enhanced by simultaneously administering folinic acid (leucovorine, LV, 5-formyl-THF) or calcium folinate. Folinic acid is a precursor that is intracellularly converted to 5,10-methylene tetrahydrofolate. The combination of UFT® and calcium folinate is more tolerable than 5-FU and folinic acid, and toxic side effects are less frequent. Together with calcium folinate, UFT® serves for the primary therapy of metastatic colorectal carcinoma. The coadministration of DPD inhibitors, such as eniluracil (5-ethynyluracil) and 5-chloro-2,4-dihydroxypyridine (CDHP), can also increase the cytotoxicity of the fluoropyrimidine derivatives. The S-1 formulation also contains potassium oxonate in addition to CDHP and tegafur, which inhibits the phosphoriboxylation of fluorouracil in the gastro-intestinal tract. This can decrease the gastro-intestinal toxicity. DPD inhibitors are examined in combination with 5-fluorouracil, capecitabine and tegafur in clinical studies.

5-Fluorouracil as well as its 8-D-ribo-(1a) and 2'-deoxy-β-D-ribonucleosides (1b) (Scheme 1) possess antitumor activity against various types of carcinomas, particularly of the breast and the gastrointestinal tract.

Scheme 1

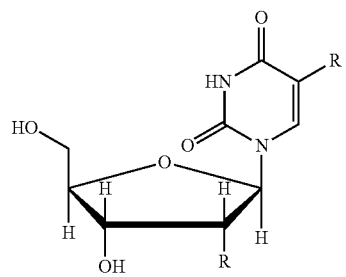

1a, R = OH
1b, R = H

Furthermore, positive results have been obtained in the topical treatment of premalignant keratosis of the skin and basal cell carcinomas [A. Albert, "Selective Toxicity—The physico-chemical basis of therapy", Chapman and Hall, London, New York, $7^{th}$ edition, 1985, pp. 60, 125-126; C. Heidelberger, L. Griesbach, O. Cruz, R. Schnitzer, F. Gruenberg, *Proc. Soc. Exper. Biol. Med.* 1958, 97, 470].

The intrathecal use of 5-fluoro-2'-deoxyuridine (1b) has been studied for meningeal dissemination of malignant brain tumors, and it has been found that this nucleoside has an excellent antitumor activity and minimal neurotoxicity [M. Yamada, H. Nakagawa, M. Fukushima, K. Shimizu, T. Hayakawa, K. Ikenaka, *J. Neuro-Oncology* 1998, 37, 115].

A large number of lipophilic prodrugs of 5-fluorouracil and its nucleosides have been prepared and found to possess useful antitumor properties. Besides Ftorafur and its derivatives recently 5-fluoro-5'-uridylic acid, mono[2-(decyloxy)-3-(dodecylsulfanyl)-propyl]ester and its salts (Fosfluridine, Tidoxil) have been used for the treatment of intraepithelial proliferative diseases [U.S. Pat. No. 7,378,401]. Further described is the synthesis of cyclic and acyclic O-2',3'-ketal derivatives of the cytostatic 5-fluorouridine [E. Malecki, H. Rosemeyer, *Helv. Chim. Acta* 2010, 93, 1500-1512; E. Malecki, F. Ye, H. Reuter, H. Rosemeyer, Helv. Chim. Acta 2009, 92, 1923-1932.]

However, the cancerostatic drugs on basis of 5-fluorouridine known in the prior art suffer from a sufficient and effective membrane uptake and permeability as well as a sufficient cancerostatic effect.

Therefore, it was an object of the present invention to provide anticancer drugs which have an improved membrane uptake and permeability as well as an improved cancerostatic effect. In particular it was an object of the present invention to provide an improved and more effective anticancer drug.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which;

FIG. 1-1 illustrates a Z-scan of an empty bilayer;

FIG. 1-2 illustrates a Z-scan after injection of a dilute solution of isolated product 36 in MeCN (1 microliter) into the cis compartment of the slide and torn of the bilayer;

FIG. 1-3 illustrates a Z-Scan after 5 minutes of incubation, where there is slowly massing of aggregates at the Teflon annulus;

FIG. 1-4 illustrates a Z-Scan after 5 further minutes of incubation, where most of the aggregates are covering the Teflon annulus;

FIG. 1-5 illustrates a repeat of the experiment as reflected in FIG. 1-1 and shows a Z-scan of an empty bilayer;

FIG. 1-6 illustrates a Z-scan after injection of a MeCN solution of compound 36 (1 microliter) to the cis compartment of the slide and 5 minutes of incubation;

FIG. 2 illustrates the relative brightness intensities of the bilayer before and after addition of isolated product 36;

FIG. 3-1 illustrates a side view of an empty bilayer;

FIG. 3-2 illustrates a sloped view of an empty bilayer;

FIG. 3-3 illustrates a side view of a bilayer after addition of oligomer 41;

FIG. 3-4 illustrates a side view of a bilayer after addition of oligomer 41;

FIG. 3-5 illustrates a side view of a filled bilayer after one perfusion;

FIG. 3-6 illustrates a sloped view of a filled bilayer after one perfusion;

FIG. 3-7 illustrates a side view of a filled bilayer after two perfusions;

FIG. 3-8 illustrates a sloped view of a filled bilayer after two perfusions;

FIG. 4-1 illustrates a side view of an empty bilayer;

FIG. 4-2 illustrates a sloped view of an empty bilayer;

FIG. 4-3 illustrates a side view of a bilayer after addition of oligomer 42;

FIG. 4-4 illustrates a side view of a bilayer after addition of oligomer 42;

FIG. 4-5 illustrates a side view of a filled bilayer after one perfusion;

FIG. 4-6 illustrates a sloped view of a filled bilayer after one perfusion;

FIG. 4-7 illustrates a side view of a filled bilayer after two perfusions;

FIG. 4-8 illustrates a sloped view of a filled bilayer after two perfusions;

FIG. 5 illustrates a schematic breadboard construction for the determination of the diffusion times of oligonucleotides;

FIG. 6 illustrates the viability/survival of human colon carcinoma cell line HT-29 after 24 h incubation with 5-fluorouridin (5-FU), its derivatives 5-FU-A, -B, -C, -D or -E or 5-fluorouracil as a control;

FIG. 7 illustrates the viability/survival of human colon carcinoma cell line HT-29 after 48 h incubation with 5-fluorouridin (5-FU), its derivatives 5-FU-A, -B, -C, -D or -E or 5-fluorouracil as a control;

FIG. 8 illustrates the viability/survival of human colon carcinoma cell line HT-29 after 72 h incubation with 5-fluorouridin (5-FU), its derivatives 5-FU-A, -B, -C, -D or -E or 5-fluorouracil as a control;

FIG. 15-1 illustrates a chitosan foil according to the present invention, fabricated from a material with a molecular weight of 20-200 kDa;

FIG. 15-2 illustrates an REM picture of the chitosan foil shown in FIG. 15-1; and FIG. 16 illustrates an REM picture of a chitosan foil which has been fabricated in the presence of PEG 600.

DETAILED DESCRIPTION OF THE INVENTION

Figure 1:
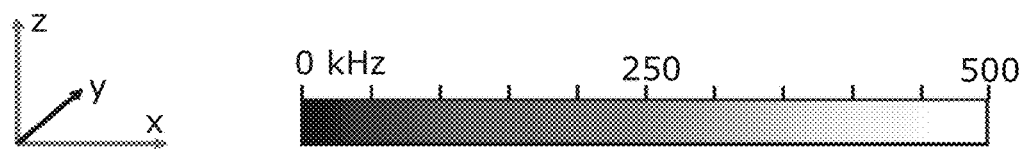
FIG. 1 llustrates an X, Y, and Z axis for scanning and a fluorescence fluctuation scale.
Figure 1:
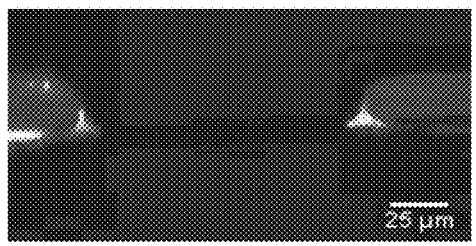

It has been surprisingly found that the specifically lipophilized 5-fluorouracil derivatives lead to drugs having an improved anticancer activity.

A first embodiment of the present invention is a compound represented by formula (I)

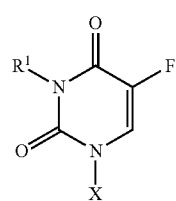

(I)

wherein X is selected from the group of formulae (II) or (III)

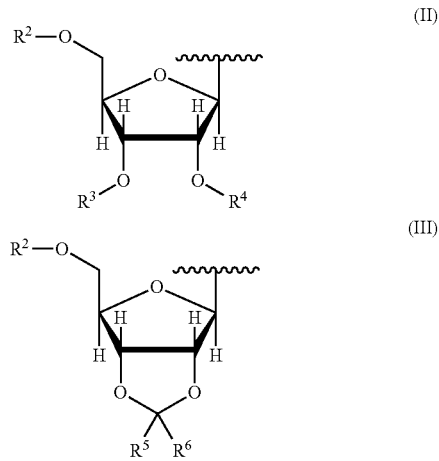

wherein
$R^1$ is H or $C_1$-$C_{50}$ chain which may be branched or linear and which may be saturated or unsaturated and which may optionally be interrupted and/or substituted by one or more hetero atom(s) (Het1) and/or functional group(s)(G1); or
$R^1$ is a $C_3$-$C_{28}$ moiety which comprises at least one cyclic structure and which may be saturated or unsaturated and which may optionally be interrupted and/or substituted by one or more hetero atom(s) (Het1) and functional group(s) (G1);
$R^2$ is H; or
$R^2$ is a Mono-phosphate, Di-phosphate, Tri-phosphate or phosphoamidite moiety;
or
$R^2$ is —Y—X or —Y-L-$Y^1$—X;
Y and $Y^1$ are independently from each other a single bond or a functional connecting moiety,
X is a colloid-active compound (CA) or a fluorescence marker (FA) or a polynucleotide moiety having up to 50 nucleotide residues, preferably 10 to 25 nucleotides, especially a polynucleotide having an antisense or antigen effect;
L is a linker by means of which Y and X are covalently linked together;
$R^3$ and $R^4$ represent independently from each other a $C_1$-$C_{28}$-alkyl moiety which may optionally be substituted or interrupted by one or more heteroatom(s) and/or functional group(s); or
$R^3$ and $R^4$ form a ring having at least 5 members, preferably a ring having 5 to 8 carbon atoms and wherein the ring may be substituted or interrupted by one or more hetero atom(s) and/or functional group(s); or
$R^3$ and $R^4$ represent independently from each other a $C_1$-$C_{28}$-alkyl moiety substituted with one or more moieties selected from the group —Y—X or —Y-L-$Y^1$—X; or
$R^3$ and $R^4$ represent independently from each other —Y—X or —Y-L-$Y^1$—X;
$R^5$ and $R^6$ represent independently from each other a $C_1$-$C_{28}$-alkyl moiety which may optionally be substituted or interrupted by one or more heteroatom(s) and/or functional group(s); or
$R^5$ and $R^6$ represent independently from each other a $C_1$-$C_{28}$-alkyl moiety substituted with one or more moieties selected from the group —Y—X or —Y-L-$Y^1$—X; or
$R^5$ and $R^6$ form a ring having at least 5 members, preferably a ring having 5 to 18 carbon atoms and wherein the ring may be substituted or interrupted by one or more hetero atom(s) and/or functional group(s);

and/or one or more moieties selected from the group —Y—X or —Y-L-Y¹—X;

$R^5$ and $R^6$ represent independently from each other —Y—X or —Y-L-Y¹—X; with the proviso that $R^1$ and $R^2$ are not both H and/or with the proviso that the compound comprises at least two chains each of which having 4 or more carbon atoms, preferably 6 or more, more preferably 8 or more carbon atoms.

The compound of the invention comprises at least two chains each which having 4 or more carbon atoms which may be carbon chains wherein the carbon atoms are linearly-linked. The chains may not be part of a cyclic system. The chains are usually not interrupted by hetero atoms.

In a preferred embodiment $R^1$ is not H.

In a preferred embodiment substituent $R^1$ is a linear or branched chain comprising 1 to 50 carbon which may be interrupted and/or substituted by one or more hetero atom(s) (Het1) and/or functional group(s) (G1). Preferably, $R^1$ is a linear or branched chain comprising 2 to 40, more preferably 3 to 30, especially 4 to 28 or 6 to 20 or 8 to 16 carbon atoms. In one aspect of the invention $R^1$ is a linear or branched $C_1$-$C_{28}$-alkyl, preferably $C_2$-$C_{20}$-alkyl, more preferably $C_4$-$C_{20}$-alkyl or $C_6$-$C_{18}$-alkyl, especially $C_8$-$C_{16}$-alkyl which may be substituted or unsubstituted. In a further aspect of the invention the carbon chain is interrupted by one or more hetero atom(s) (Het1) wherein the Het1 is preferably selected from O, S and N, more preferably selected from O or N. In one aspect the substituent $R^1$ is interrupted by up to 3 hetero atom(s) (Het1), preferably 1 or 2 hetero atoms such as O. In a further aspect of the invention the carbon chain of substituent $R^1$ is interrupted by nitrogen which preferably further branches the chain. An exemplary embodiment of this type of substituent is reflected in the following formula:

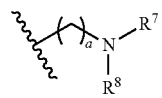

wherein $R^7$ and $R^8$ are independently selected from a $C_1$ to $C_{30}$ chain which can be saturated or unsaturated, preferably a $C_1$ to $C_{30}$ alkyl, preferably $C_4$ to $C_{24}$ alkyl, more preferably $C_8$ to $C_{22}$ alkyl and especially $C_{12}$ to $C_{18}$ alkyl; or a $C_2$ to $C_{30}$ chain having one or more carbon-carbon double and/or carbon-carbon triple bond(s); and "a" is an integer ranging from 1 to 20, preferably 2 to 18, more preferably 3 to 12 or 4 to 8. However, the linking moiety which links the nitrogen atom with substituents $R^7$ and $R^8$ to 5-fluorouracil moiety can also be a unsaturated carbon chain having one 2 to 20 carbon atoms and one or more carbon-carbon double and or carbon-carbon triple bonds. The exemplary substituent of the following formula:

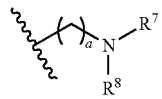

can be synthesized by various synthetic routes. Scheme 2 shows several synthetic routes for precursors which can be attached to the 5-fluorouracil moiety.

Scheme 2

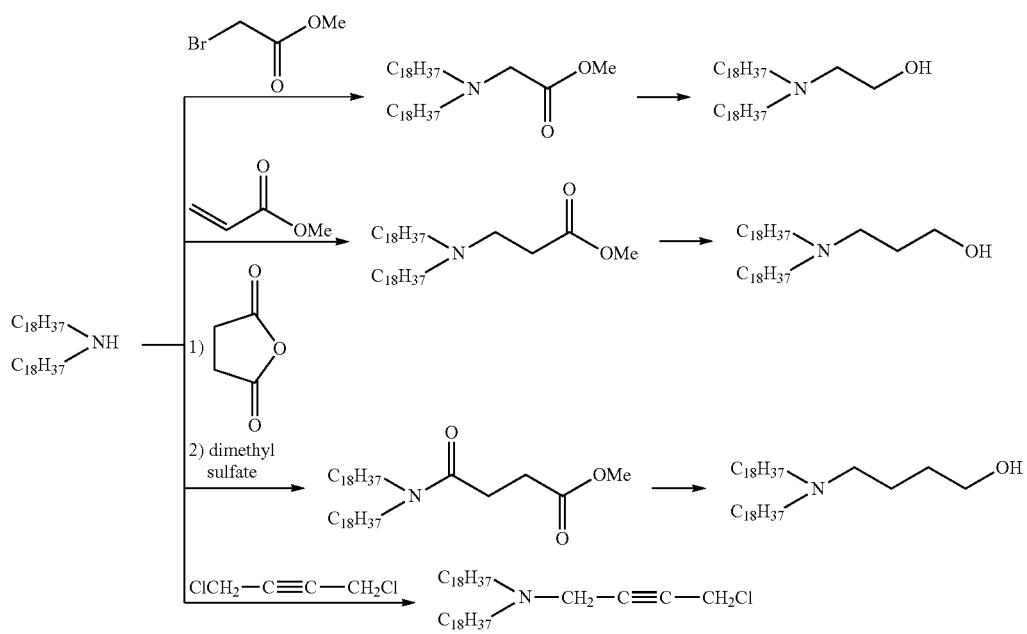

As can be seen from Scheme 2 various precursor for the connection with the nitrogen atom of the 5-fluorouracil moiety can be obtained by different synthetic routes. In a preferred embodiment of the present invention substituent $R^1$ is a double chained substituent. The double chained substituents can be obtained as reflected in Scheme 2.

In a first aspect the dioctadecylamine is reacted with methyl bromoacetate in the presence of dibenzo-[18]- crown-6 which leads to the pure methyl ester in almost quantitative yield. The ester can be reduced with LiAlH$_4$ to give the alcohole.

In order to extend the spacer between the hydroxyl group and the nitrogen carrying the carbon chains the dioctadecylamine can be reacted with methyl acrylate which results in almost quantitative yield to the ester which was further reduced with LiAlH$_4$ to give a lipophilic aminopropanol derivative.

In a further aspect the dioctadecylamine was reacted with succinic anhydride to give the acid which can be converted to the methyl ester by reaction with dimethyl sulphate in the presence of K$_2$CO$_3$. The methyl ester can then be reduced with LiAlH$_4$ yielding the further extended alcohole, namely a lipophilized 4-aminobutanol derivative.

In a further reaction the dioctadecylamine can be alkylated with 1,4-dichlorobut-2-ine in the presence of Na$_2$CO$_3$ in benzene.

In the following Scheme 3 various synthetic routes to obtain single chain precursor or double chain precursor with different chains for the substitution of the 5-fluorouracil moiety are disclosed. The single chain precursor reflected in Scheme 3 is interrupted by a hetero atom (N) or a functional group (amid; NHCO).

Scheme 3

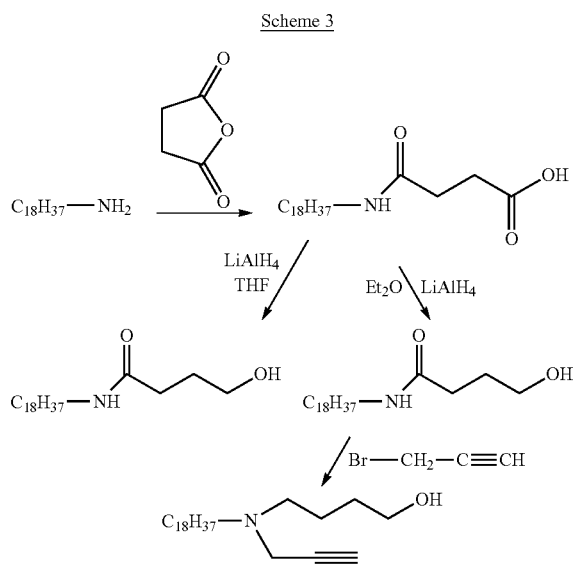

As can be seen from Scheme 3 lipid single chain precursors can be obtained by the reaction of octadecylamine with succinic anhydride which leads to the acid which can be reduced with LiAlH$_4$ in THF at ambient temperature which leads to the reduction of the carboxylic group only, but not of the amide moiety and results into the amidoalcohole in 82% yield. Replacement of THF by Et$_2$O however results in the amino alcohol in a high yield of 84%. Subsequent reaction of amino alcohol with propargyl bromide results in the double chained alkine in 61% yield.

It has surprisingly been found that the lipophilic carbon chains comprising a hydroxyl functional group or a halide can be introduced regioselectively into the 5-fluorouracil derivative. The lipophilic groups can principally be positioned either at the heterocyclic base or at the glyconic moiety and can be introduced by various methods, e.g. by base-catalysed alkylation with alkyl halides.

The reaction of unprotected 5-fluorouracil derivatives with halogenated alkyls, alkenes or alkines can be performed in DMF/K$_2$CO$_3$ (direct alkylation) and leads to the alkylation of the unsubstituted nitrogen atom in the 5-fluorouracil ring.

Preferably, the unsubstituted nitrogen atom in the 5-fluorouracil ring is substituted by a halogen substituted precursor under the proviso that the hydroxyl groups present in the 5-fluorouracil derivative are protected by protecting groups. Suitable protecting groups are known to the person skilled in the art. Examples are dimethoxytrityl (DMT) and a tert-butyl-dimethylsilyl group.

Surprisingly it has been found that the hydroxyl functional lipophilic precursor (such as the amino alcohols reflected in Scheme 2 and 3) can be selectively reacted with the unsubstituted nitrogen atom of the 5-fluorouracil derivative by a Mitsunobu reaction. This reaction is carried out by first protecting any hydroxyl groups which may be present in the 5-fluorouracil derivative.

The Mitsunobu reaction is generally carried out by reacting the alcohol and the 5-fluorouracil derivative which comprises the unsubstituted ring nitrogen atom in the presence of triphenylphosphine and diisopropylazo dicarboxylate (DIAD).

Further, R$^1$ is preferably a C$_2$ to C$_{40}$ chain which is unsaturated, more preferably a C$_8$ to C$_{28}$ chain which is unsaturated. In one embodiment of the invention Fe comprises one or more carbon-carbon double bond(s) and/or one or more carbon-carbon triple bond(s). In a particular preferred embodiment R$^1$ comprises two or more, especially 2 to 6, such as 2 to 4 carbon-carbon double bonds.

In a specially preferred embodiment the substituents are derived from nature. Suitable naturally derived substituents have a structure derived from terpenes. When terpenes are chemically modified such as by oxidation or rearrangement of the carbon skeleton, the resulting compounds are generally referred to as terpenoids. In a preferred embodiment Fe is a cyclic or alicyclic terpenoid, preferably a terpenoid having 8 to 36 carbon atoms.

The terpenes are preferably selected from monoterpenes, sesquiterpenes, diterpenes, sesterterpenes, triterpenes and sesquaterpenes.

Suitable monoterpenes or monoterpenoids which can be acyclic or cyclic are selected from the group consisting of geraniol, limonene, pinen, bornylen, nerol.

Suitable sesquiterpenes sesquiterpenoids which can be acyclic or cyclic may inter alia be selected from farnesol.

Suitable sesterterpenes or sesterterpenoids are inter alial selected from geranylfarnesol.

Suitable diterpenes or diterpenoids can be selected from the group consisting of abietic acid, aphidicolin, cafestol, cembrene, ferruginol, forskolin, guanacastepene A, kahweol, labdane, lagochilin, sclarene, stemarene, steviol, taxadiene (precursor of taxol), tiamulin, geranylgeraniol and phytol.

According to an especially preferred embodiment of the invention R$^1$ is selected from the group consisting of geranyl, farnesyl, neryl and phythyl.

According to a further alternative aspect R$^1$ is H or C$_3$-C$_{28}$ chain which may be branched or linear and which may be saturated or unsaturated and which may optionally be interrupted and/or substituted by one or more hetero atom(s) (Het1) and/or functional group(s)(G1); or
R$^1$ is a C$_1$-C$_{28}$ moiety which comprises at least one cyclic structure and which may be saturated or unsaturated and which may optionally be interrupted and/or substituted by one or more hetero atom(s) (Het1) and functional group(s) (G1);

According to a preferred embodiment $R^1$ is selected from H,

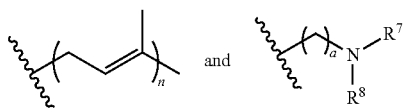

and substituted or unsubstituted cyclic terpene moieties, wherein
$R^7$ and $R^8$ are independently selected from $C_1$ to $C_{30}$ alkyl,
n is an integer ranging 1 to 4, preferably n is 1 or 2; and
a is an integer ranging from 1 to 20, preferably 2 to 18

In a preferred embodiment $R^3$ and $R^4$ represent independently from each other a $C_1$-$C_{28}$-alkyl moiety which may optionally be substituted or interrupted by one or more heteroatom(s) and/or functional group(s). Preferably the one or more heteroatom(s) are selected from the group consisting of O, S and N. Further, the one or more functional group(s) is/are preferably selected from the group consisting of ester, amide, carboxylic acid, thioester, thioamides and thioether.

Alternatively, preferred is an embodiment wherein $R^3$ and $R^4$ form a ring having at least 5 members, preferably a ring having 5 to 8 carbon atoms and wherein the ring may be substituted or interrupted by one or more heteroatom(s) and/or functional group(s) and wherein the one or more heteroatom(s) are selected from O, S and N. Preferably, the one or more functional group(s) is/are selected from ester, amide, carboxylic acid, thioester, thioamides and thioether.

In a preferred embodiment $R^5$ and $R^6$ represent independently from each other a $C_1$-$C_{28}$-alkyl moiety which may optionally be substituted or interrupted by one or more heteroatom(s) and/or functional groups. Preferably, the one or more heteroatoms are selected from the group consisting of O, S and N. Further, the one or more functional group(s) is/are preferably selected from the group consisting of ester, amide, carboxylic acid, thioester, thioamides and thioether.

Alternatively, preferred is an embodiment wherein $R^5$ and $R^6$ form a ring having at least 5 members, preferably a ring having 5 to 8 carbon atoms and wherein the ring may be substituted or interrupted by one or more heteroatom(s) and/or functional group(s) and wherein the one or more heteroatom(s) are selected from O, S and N. Preferably, the one or more functional group(s) are selected from ester, amide, carboxylic acid, thioester, thioamides and thioether.

Preferably, Y and $Y^1$ is are functional connecting groups which are independently selected from a group consisting of carboxylic acid ester, carboxylic acid amides, urethane, ether, amino group, thioester, thioamides and thioether.

According to preferred embodiment the hetero atom(s) Het1 is selected from O, S and NH.

Further, preferably the functional group(s)(G1) are selected from ester, amide, carboxylic acid, thioester, thioamides and thioether.

In a further aspect of the invention linker L is a moiety comprising 1 to 30 carbon atoms which can be saturated or unsaturated, cyclic or alicyclic, branched or unbranched and which may be substituted or interrupted by heteroatoms.

Preferably, linker L is selected from $C_2$ to $C_{20}$ alkandiyls, preferably selected from ethylene or propylene.

In a further aspect of the invention linker L is selected from a single bond or a saturated or unsaturated moiety having 1 to 30, preferably 2 to 20 carbon atoms, more preferably a carbon chain which may be substituted and/or interrupted by one or more functional groups selected from carboxylic acid ester, phosphate ester, carboxylic acid amides, urethane, ether and amine groups. L may also comprise cyclic moieties.

According to a preferred embodiment linker L is selected from a single bond; alkandiyl, preferably $C_1$-$C_{20}$-alkandiyl; alkendiyl, preferably a $C_2$-$C_{20}$-alkendiyl; alkyndiyl, preferably a $C_2$-$C_{20}$-alkyndiyl; aryl moiety, aralkyl moiety and herterocyclic moiety.

Preferably, the alkandiyl represents a straight-chain or branched-chain alkandiyl group bound by two different carbon atoms to the molecule, it preferably represents a straight-chain or branched-chain $C_{1-12}$ alkandiyl, particularly preferably represents a straight-chain or branched-chain $C_{1-6}$ alkandiyl; for example, methandiyl (—$CH_2$—), 1,2-ethanediyl (—$CH_2$—$CH_2$—), 1,1-ethanediyl ((—CH($CH_3$)—), 1,1-, 1,2-, 1,3-propanediyl and 1,1-, 1,2-, 1,3-, 1,4-butanediyl, with particular preference given to methandiyl, 1,1-ethanediyl, 1,2-ethanediyl, 1,3-propanediyl, 1,4-butanediyl.

Further, preferably the alkendiyl represents a straight-chain or branched-chain alkendiyl group bound by two different carbon atoms to the molecule, it preferably represents a straight-chain or branched-chain $C_{2-6}$ alkendiyl; for example, —CH=CH—, —CH=C($CH_3$)—, —CH=CH—$CH_2$—, —C($CH_3$)=CH—$CH_2$—, —CH=C($CH_3$)—$CH_2$—, —CH=CH—C($CH_3$)H—, —CH=CH—CH=CH—, —C($CH_3$)=CH—CH=CH—, —CH=C($CH_3$)—CH=CH—, with particular preference given to —CH=CH—$CH_2$—, —CH=CH—CH=CH—.

The aryl moiety preferably represents an aromatic hydrocarbon group, preferably a $C_{6-10}$ aromatic hydrocarbon group; for example phenyl, naphthyl, especially phenyl which may optionally be substituted.

Aralkyl moiety denotes an "Aryl" bound to an "Alkyl" and represents, for example benzyl, α-methylbenzyl, 2-phenylethyl, α,α-dimethylbenzyl, especially benzyl.

Heterocyclic moiety represents a saturated, partly saturated or aromatic ring system containing at least one hetero atom. Preferably, heterocycles consist of 3 to 11 ring atoms of which 1-3 ring atoms are hetero atoms. Heterocycles may be present as a single ring system or as bicyclic or tricyclic ring systems; preferably as single ring system or as benz-annelated ring system. Bicyclic or tricyclic ring systems may be formed by annelation of two or more rings, by a bridging atom, e.g. oxygen, sulfur, nitrogen or by a bridging group, e.g. alkendiyl or alkenediyl. A Heterocycle may be substituted by one or more substituents selected from the group consisting of oxo (=O), halogen, nitro, cyano, alkyl, alkoxy, alkoxyalkyl, alkoxycarbonyl, alkoxycarbonylalkyl, halogenalkyl, aryl, aryloxy, arylalkyl. Examples of heterocyclic moieties are: pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, furazane (oxadiazole), dioxolane, thiophene, dihydrothiophene, tetrahydrothiophene, oxazole, oxazoline, oxazolidine, isoxazole, isoxazoline, isoxazolidine, thiazole, thiazoline, thiazlolidine, isothiazole, istothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine, morpholine, purine, pterine, and the corresponding benz-annelated heterocycles, e.g. indole, isoindole, cumarine, cumaronecinoline, isochinoline, cinnoline and the like.

Heteroatoms are atoms other than carbon and hydrogen, preferably nitrogen (N), oxygen (O) or sulfur (S).

In a preferred embodiment of the present invention linker $L^1$ is selected from the group consisting of a single bond and a $C_1$-$C_{10}$ alkandiyl, preferably a $C_2$-$C_6$-alkandiyl, especially ethan-1,2-diyl (ethylene) or propan-1,2-diyl or propan-1,3-diyl.

Specifically, X is a colloid-active compound (CA) selected from the group consisting of amyloses, amylopectins, acemannans, arabinogalactans, galactomannans, galactoglucomannans, xanthans, carrageenan, hyaluronic acid, deacetylated hyaluronic acid, chitosan, starch and modified starch.

In a preferred embodiment X is a modified starch which is selected from the group consisting of hydroxyalkyl starches, esterified starches, carboxyalkyl starches, hydroxyalkyl carboxyalkyl starch, aminated hydroxyalkyl starch, aminated hydroxyalkyl carboxyalkyl starch and aminated carboxyalkyl starch.

In a particularly preferred embodiment said modified starch is selected from hydroxyethyl starch or aminated hydroxyethyl starch or carboxmethyl starch or carboxyethyl starch.

Generally, the colloid-active compound (CA) has an average molecular weight of from 20,000 to 800,000 daltons, preferably from 25,000 to 500,000 daltons, especially from 30,000 to 200,000 daltons.

Suitable modified starches preferably have a degree of substitution, DS, of the modified starch, especially hydroxyethyl starch, from 0.2 to 0.8, preferably from 0.3 to 0.6.

According to an alternative embodiment X is a fluorescence marker which is selected from the group consisting of fluorescein isothiocyanate (FITC), phycoerythrin, rhodamide and 2-aminopyridine, carbocyamine dyes and bodipy dyes.

In a preferred embodiment the compound according to the invention is represented by formula (I)

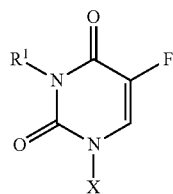

(I)

wherein X is selected from the group of formulae (II) or (III)

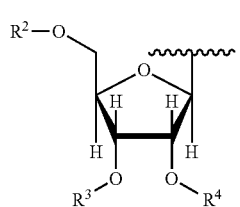

(II)

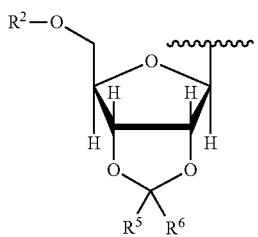

(III)

wherein
$R^1$ is H or $C_1$-$C_{50}$ chain which may be branched or linear and which may be saturated or unsaturated and which may optionally be interrupted and/or substituted by one or more heteroatom(s) (Het1) and/or functional group(s)(G1); or
$R^1$ is a $C_3$-$C_{28}$ moiety which comprises at least one cyclic structure and which may be saturated or unsaturated and which may optionally be interrupted and/or substituted by one or more heteroatom(s) (Het1) and functional group(s) (G1);
$R^2$ is H; or
$R^2$ is a Mono-phosphate, Di-phosphate, Tri-phosphate or phosphoamidite moiety;
or
$R^2$ is —Y—X or —Y-L-$Y^1$—X;
Y and $Y^1$ are independently from each other a single bond or a functional connecting moiety,
X is a colloid-active compound (CA) or a fluorescence marker (FA) or a polynucleotide moiety having up to 50 nucleotide residues, preferably 10 to 25 nucleotides, especially a polynucleotide having an antisense or antigen effect;
L is a linker by means of which Y and X are covalently linked together;
$R^3$ and $R^4$ represent independently from each other a $C_1$-$C_{28}$-alkyl moiety which may optionally be substituted or interrupted by one or more heteroatom(s) and/or functional group(s); or
$R^3$ and $R^4$ form a ring having at least 5 members, preferably a ring having 5 to 8 carbon atoms and wherein the ring may be substituted or interrupted by one or more heteroatom(s) and/or functional group(s); or
$R^3$ and $R^4$ represent independently from each other a $C_1$-$C_{28}$-alkyl moiety substituted with one or more moieties selected from the group —Y—X or —Y-L-$Y^1$—X; or
$R^3$ and $R^4$ represent independently from each other —Y—X or —Y-L-$Y^1$—X;
$R^5$ and $R^6$ represent independently from each other a $C_1$-$C_{28}$-alkyl moiety which may optionally be substituted or interrupted by one or more heteroatom(s) and/or functional group(s); or
$R^5$ and $R^6$ represent independently from each other a $C_1$-$C_{28}$-alkyl moiety substituted with one or more moieties selected from the group —Y—X or —Y-L-$Y^1$—X; or
$R^5$ and $R^6$ form a ring having at least 5 members, preferably a ring having 5 to 18 carbon atoms and wherein the ring may be substituted or interrupted by one or more heteroatom(s) and/or functional group(s);
and/or one or more moieties selected from the group —Y—X or —Y-L-Y'—X;
$R^5$ and $R^6$ represent independently from each other —Y—X or —Y-L-$Y^1$—X;
wherein the heteroatoms (Het1) are selected from the group consisting of 0, S and H;

the functional group(s) are preferably independently selected from ester, amide, carboxylic acid, thioester, thioamides and thioether;

Y and Y1 are independently selected from the group consisting of carboxylic acid ester, carboxylic acid amides, urethane, ether, amino groups, thioester, thioamides and thioether;

L is selected from the group consisting of ethylene and propylene;

X is a colloid active compound selected from the group consisting of amylases, amylopectines, acemannans, arabinogalactans, galactomannans, galactoglucomannans, xanthans, carrageenan, chitosan, starch, modified starch hyluronic acid and deacetylated hyaluronic acid, or a fluorescence marker selected from the group consisting of fluorescein isocyanate, phycoerythrin, rhodamine and 2-aminopyridine, carbocyanine dyes, bodipy dyes and coumarine dyes.

According to preferred embodiment the compound (I) of the invention can be represented by the following formula (IIa)

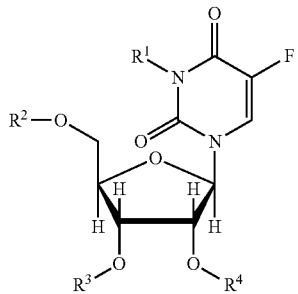

According to preferred embodiment the compound (I) of the invention can be represented by the following formula (IIIc):

(IIIa)

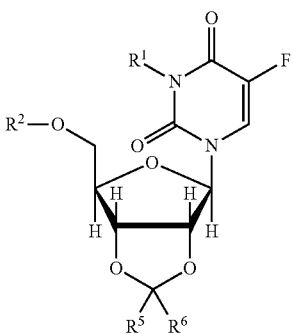

Further preferred is an embodiment of the present invention wherein the compound (I) of the invention is represented by formula (IIIc) wherein $R^1$ is selected from the group consisting of H, farnesyl, phytyl, neryl and abietyl;

$R^2$ is selected from the group consisting of H, Atto 488, (MeO$_2$)Tr-, —SiMe$_2^t$Bu and a phosphoramidite moiety;

$R^5$ and $R^6$ are independently selected from the group consisting of methyl, propyl, nonyl, 4-oxobutylidene, chitosan and Atto 488; or $R^5$ and $R^6$ form a ring consisting of at least 5 carbon atoms, preferably 10 to 15 carbon atoms.

A further embodiment of the present invention is a pharmaceutical composition comprising a compound of the present invention.

Especially the pharmaceutical composition is suitable for use in the treatment of cancer, especially selected from tumors of the gastro-intestinal tract, e.g. HT29 human colon cancer, breast cancer, premalignant keratosis of the skin and basal all carcinomas.

A further embodiment of the present invention is a process for preparing a compound represented by formula (I)

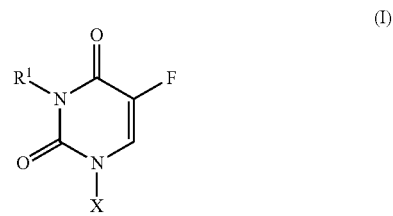

wherein $R^1$ is $C_1$-$C_{28}$ chain which may be branched or linear and which may be saturated or unsaturated and which may optionally be interrupted and/or substituted by one or more hetero atom(s) (Het1) and/or functional group(s)(G1); or $R^1$ is a $C_1$-$C_{28}$ moiety which comprises at least one cyclic structure and which may be saturated or unsaturated and which may optionally be interrupted and/or substituted by one or more hetero atom(s) (Het1) and functional group(s) (G1);

X is as defined in at least one of the preceding claims comprising the following steps:

a) providing a compound of formula (IA) and introducing protecting groups for hydroxyl groups, if present

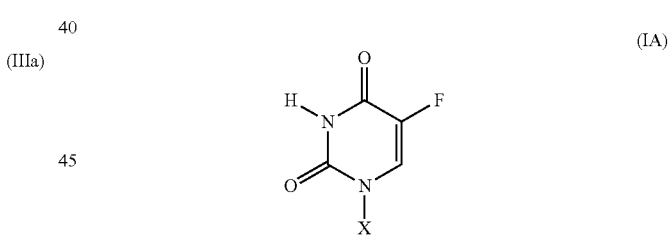

b) converting an alcohol of the formula $R^1$—OH in a Mitsunobu type reaction with the compound (IA) and c) optionally, removing the protecting groups.

According to a preferred embodiment of the process of the invention $R^1$—OH is selected from the group consisting of nerol, phythol, eicosapentaenol and docosahexaenol.

In an exemplary aspect of the invention the biomimetic lipophilization of 5-fluorouridine has been conducted by use of the terpenols phytol as well as nerol which are coupled to N(3) of the nucleoside applying Mitsunobu reaction conditions. Nerol is a monoterpene found in many essential oils such as lemongrass and hops. The diterpene phytol is—inter alia—a constituent of chlorophyll with which the latter is embedded in the thylakoid membranes of chloroplasts.

Scheme 4 which follows shows an exemplary reaction sequence for the lipophilasation of the 5-fluoruoracil derivative (1) by the Mitsunobu reaction.

Scheme 4

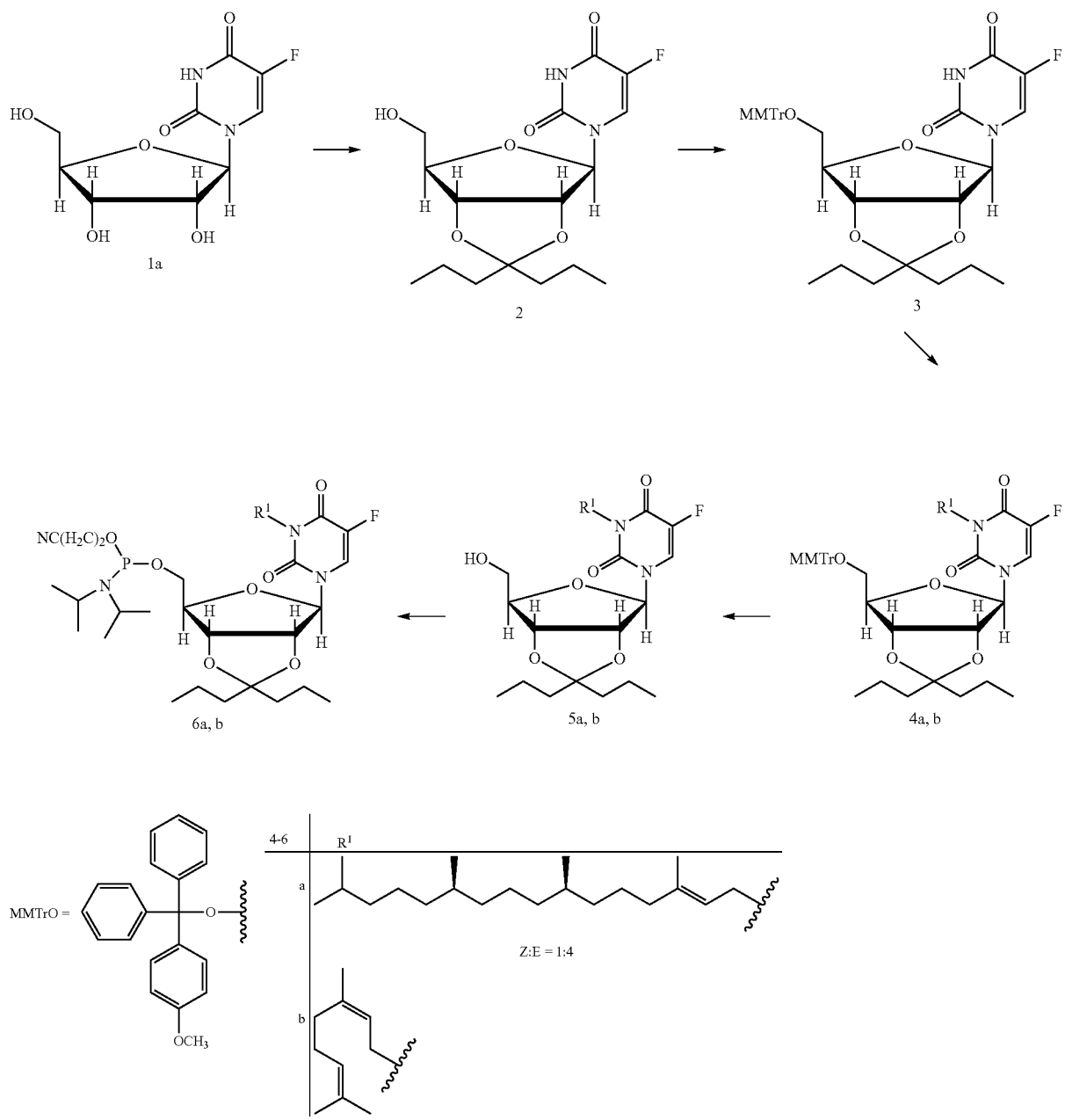

It has surprisingly found that Mitsunobu reactions between an alcohol and the nucleoside lead preferably and predominantly to a main base-alkylated product, if the nucleoside is fully protected at the glyconic moiety.

Moreover, such a reaction requires a $pK_{BH+}$ value of the nucleosidic educt which ranges between 0 and 14. 5-fluorouridine (1a) or its derivatives having a $pK_{BH+}=8.0\pm0.1$ is therefore suitable for the Mitsunobu alkylations. Scheme 4 shows that compound 1a has been protected first at the 2',3' hydroxyls by reaction with heptan-4-one in the presence of ethyl orthoformate and 4M HCl in 1,4-dioxane and obtained compound 2b. This had been prepared before and possesses a suitably high acidic stability at the ketal group [T=130 min in 1N aq. HCl/MeCN, 1:1, (v/v)]. The latter can then be protected at the 5'-OH group with a 4-monomethoxy-triphenylmethyl residue (→3). This intermediate was next submitted to Mitsunobu alkylations with either phytol or nerol (PPh₃, DEAD, THF, 0° C.) which gave compounds 4a, b. Both were subsequently detritylated in 4% dichloroacetic acid in dichloromethane at room temperature for 10 min leading to compounds 5a,b which possess significantly enhanced log P values compared to 5-fluorouridine (1a: log P=−1.34±0.46; 4a: log P=+12.5±0.63; 5b: log P=+7.65±0.65). The latters were then phosphitylated to give the phosphoramidites 6a, b.

In the following scheme 5 a further way to lipophilize the 5-fluorouracil derivatives using the cyclic diterpene abietol 14 is shown.

Scheme 5
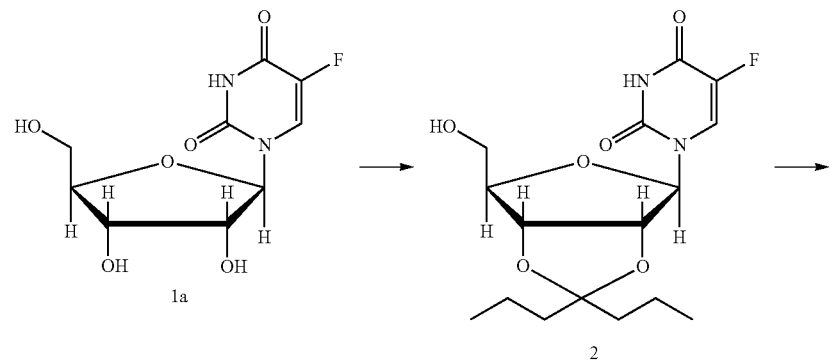
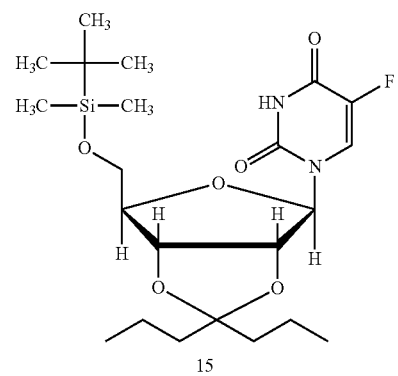
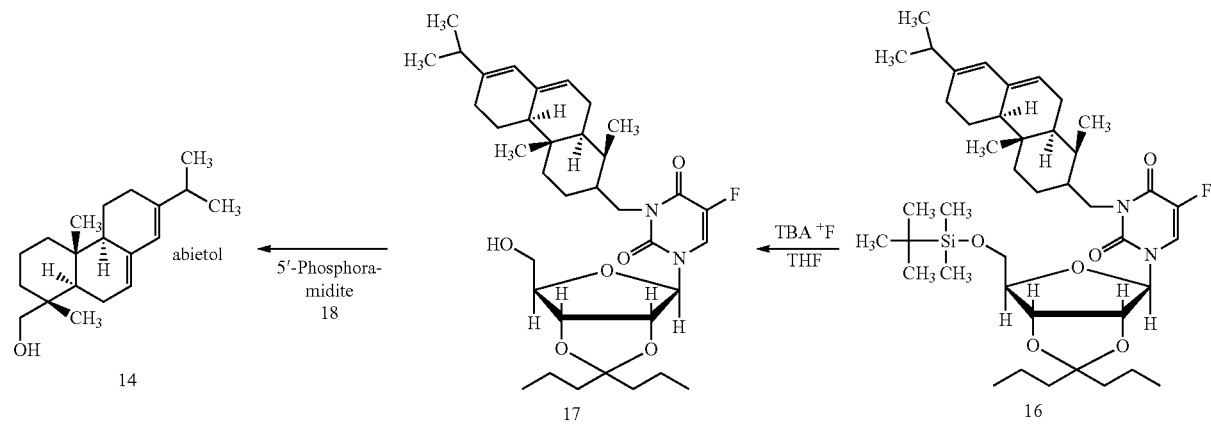

The following scheme 6 shows further exemplary ways to obtain lipophilized 5-fluorouracil derivatives.
Scheme 6
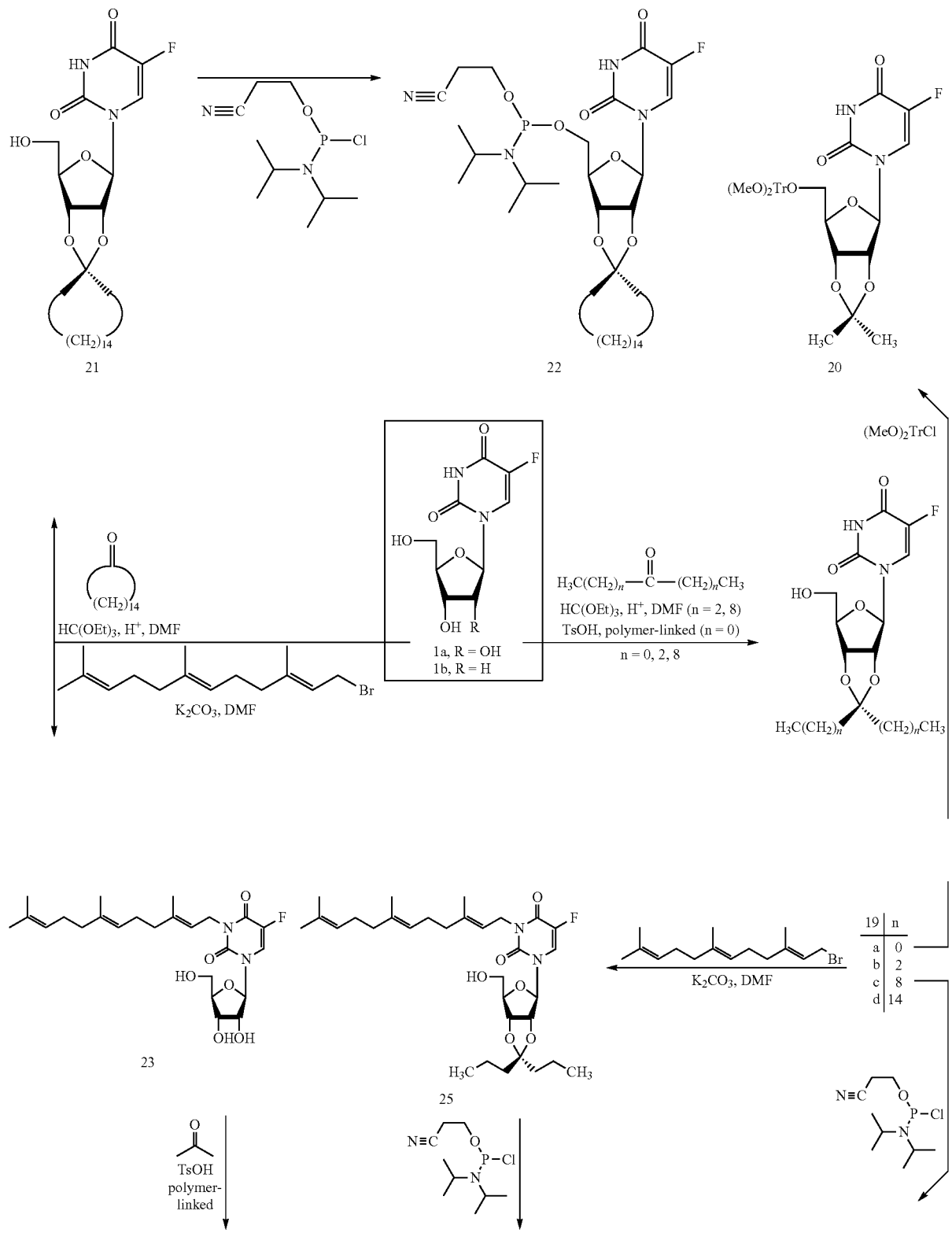

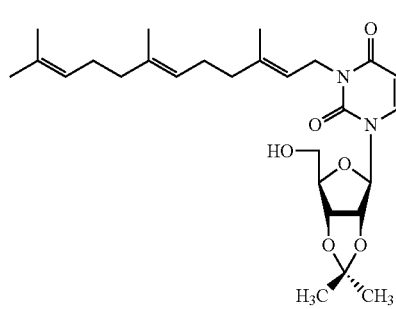

24

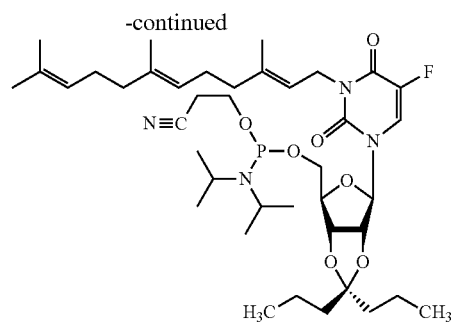

26

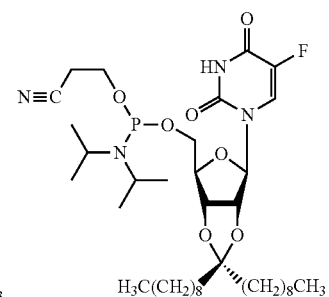

27

In a further preferred embodiment the compound of the present invention comprises a colloid-active compound (CA) which is linked to the 5-fluorouridine moiety preferably via a functional connecting moiety, such as via an ester. Preferred colloid-active compounds are selected from the group consisting of chitosan, hydroxyethyl starch and carboxyethyl starch.

In an exemplary embodiment compound 28a was saponified in situ to yield the acid 37. The ester 28a was, moreover, alkylated with farnesylbromide to give the lipophilized ester 29a which could be also saponified to the acid 38. The compounds referred to are reflected in the following scheme 7.

Scheme 7

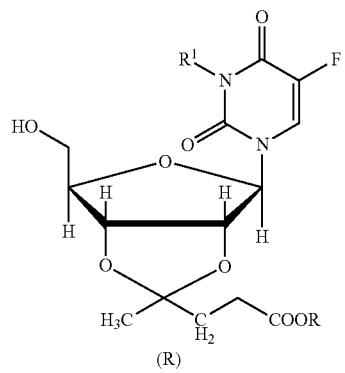

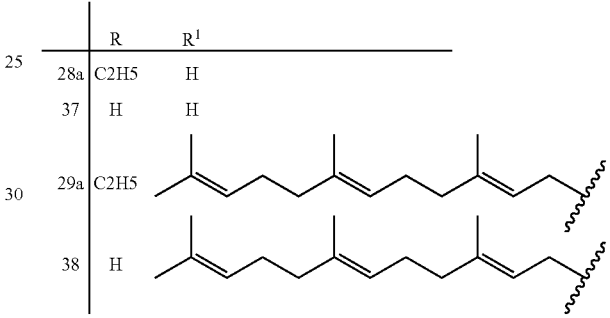

(R) Notation refers to the stereogenic center at the actal C-atom

Both acids (37, 38) can be coupled to chitosan—either with an $M_w$, 12.000 Da (pH: 3.5 to 5.0) or with an $M_w$, of 1.100 Da (pH: 5.0)-(deacetylation grade, 97.5% or 75%, respectively) by EDC-coupling in aqueous solution (pH 4.0-5). After intensive dialysis against water (for 2 days), the resulting conjugates 39, 40 were dried by lyophilization, and their ligand concentration was determined UV-spectrophotometrically after complete hydrolysis in 6 N HCl aq. for 1 hour. The following scheme 8 shows the exemplary coupling products 39 and 40.

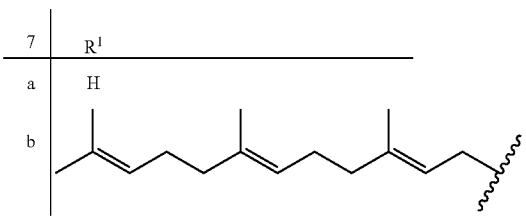

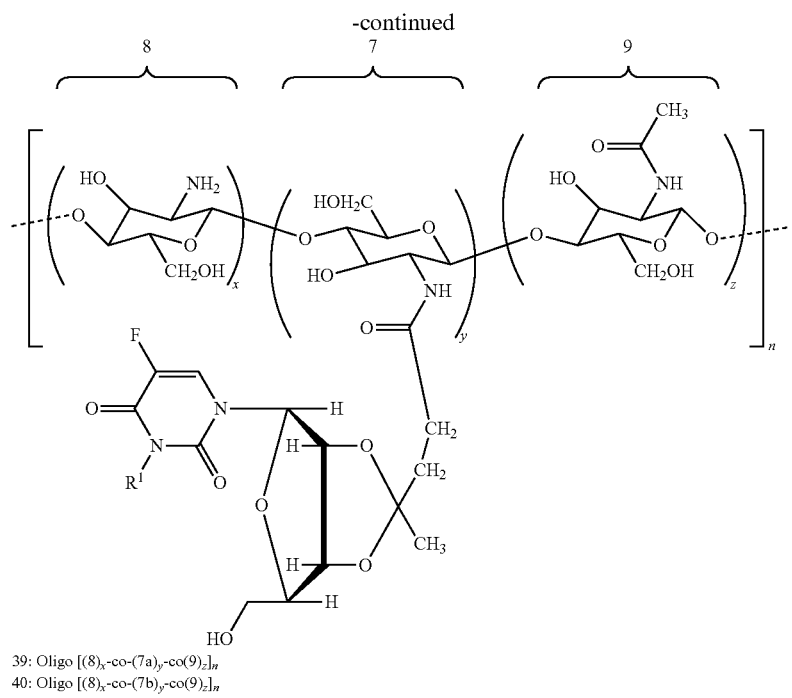

39: Oligo [(8)$_x$-co-(7a)$_y$-co(9)$_z$]$_n$
40: Oligo [(8)$_x$-co-(7b)$_y$-co(9)$_z$]$_n$ wherein n, x, y, and z are integers which are independently ranging from 1 to 10000, preferably 2 to 1000, more preferably 5 to 500, especially 8 to 100.

In a further preferred embodiment the compound of the present invention is represented by formula (IIIa)

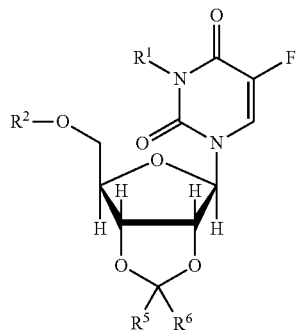

(IIIa)

wherein
$R^1$ is H;
$R^2$ is H;
$R^5$ and $R^6$ are independently selected from methyl and —Y-L-Y$^1$—X, with the provisio that when $R^5$ is methyl than $R^6$ is —Y-L-Y$^1$—X;
And when $R^5$ is —Y-L-Y$^1$—X than $R^6$ is methyl;
Y is a single bond;
L is a carbon chain comprising 2 carbon atoms, preferably ethylene;
$Y^1$ is an amide moiety; and
X is chitosan.

A further aspect of the invention is a chitosan to which the 5-fluorouridine is bound and which is present in the form of a foil. Preferably, the chitosan foil is a ductile and tear-proof foil.

According to a further preferred embodiment of the invention the chitosan foil can be prepared by dissolving the chitosan derivative carrying the 5'-fluorouracil derivative in a mixture of water, a weak acid and an alcohol. In a preferred embodiment the solvent can be a mixture of, for example water, formic acid and methanol. The chitosan used may have an average molecular weight ranging from 10 kDa to 250 kDa, for example 14 kDa, 34 kDa, 82 kDa or 20-200 kDa. The solution comprising the dissolved chitosan derivative may then be poured into a suitable dish, dried, neutralized with a dilute aqueous NaOH solution and washed with water to obtain the ductile and tear-proof chitosan foils according to the invention which carry 5'fluorouracil derivatives according to the invention.

Further, preferred is an embodiment of the present invention wherein the chitosan foils according to the invention are used in the topical treatment of dermatological diseases or as wound pads.

In a further preferred embodiment of the present invention the 5'-fluoruridine derivative bound to the chitosan foil in such a way that it can be released under controlled conditions. The degradation may be carried out chemically or enzymatically. A suitable enzyme is, for example, chitosanase from Streptomyces sp. 174. The acidic stability of the foils according to the invention can be measured via RP-18 HPLC.

Therefore, a further aspect of the invention is a wound dressing comprising a compound of the invention having a colloid active compound (moiety), preferably a chitosan or chitin moiety.

Scheme 8

In a further approach the acids 37 and 38 were coupled sequentially with the fluorescent dye Atto-488® (as butanoate) to chitosane (1.1 kDa) to give the oligomers 11 and 12 which proved both water soluble. Scheme 9 shows the exemplary coupling products 11 and 12.

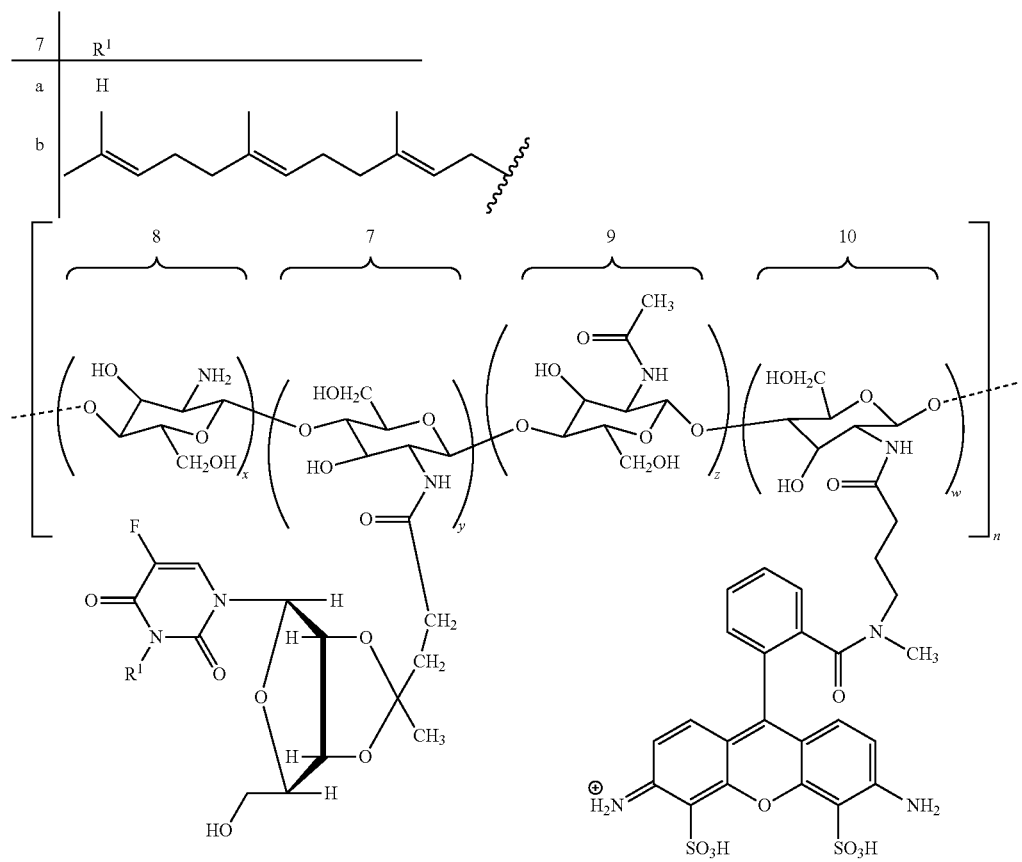

11: Oligo [(8)$_x$-co-(7a)$_y$-co(9)$_z$-co(10)$_w$]$_n$
12: Oligo [(8)$_x$-co-(7b)$_y$-co(9)$_z$-co(10)$_w$]$_n$ wherein n, x, y, and z as well as w are integers which are independently ranging from 1 to 10000, preferably 2 to 1000, more preferably 5 to 500, especially 8 to 100.

Scheme 9
Synthesis of Lipooligonucleotides and Incorporation into a Bilayer

The phosphoramidite 27 was used to prepare the following oligonucleotides with an appending nucleolipid 19c according to methods known to the person skilled in the art:

```
5'-d(19c-Cy5-TAG GTC AAT ACT)-3'     33

5'-d(19c-TAG GTC AAT ACT)-3'         34

3'-d(ATC CAG TTA TGA)-5'             35
```

The cyanine-5—labelled oligomer 33 was used to study the incorporation efficiency of lipid bilayer incorporation with respect to velocity and stability. The oligomer 34 was used to study the duplex formation between this lipooligonucleotide and its complementary strand 35 at the lipid bilayer—water phase boundary layer using SYBR Green as intercalating fluorescent dye.

Experimental Part
General.

All chemicals were purchased from Sigma-Aldrich (D-Deisenhofen) or from TCI—Europe (B-Zwijndrecht). Solvents were of laboratory grade and were distilled before use. TLC: aluminum sheets, silica gel 60 F$_{254}$, 0.2 mm layer (Merck, Germany). M.p. Büchi SMP-20, uncorrected. UV Spectra: Cary 1E spectrophotometer (Varian, D-Darmstadt). NMR Spectra: AMX-500 spectrometer (Bruker, D-Rheinstetten); $^1$H: 500.14 MHz, $^{13}$C: 125.76 MHz, and $^{31}$P: 101.3 MHz. Chemical shifts are given in ppm relative to TMS as internal standard for 1H and $^{13}$C nuclei and external 85% H$_3$PO$_4$; J values in Hz. ESI MS Spectra were measured on a Bruker Daltronics Esquire HCT instrument (Bruker Daltronics, D-Leipzig); ionization was performed with a 2% aq. formic acid soln. Elemental analyses (C, H, N) of crystallized compounds were performed on a VarioMICRO instrument (Fa. Elementar, D-Hanau). log P values were calculated using the program suite ChemSketch (version 12.0, provided by Advanced Chemistry Developments Inc.; Toronto, Canada; http://www.acdlabs.com. Oligonucleotides were synthesized, purified, and characterized (MALDI-TOF MS) by Eurogentec (Eurogentec S. A., Liege Science Park, B-Seraing).

RP-18 HPLC.

RP-18 HPLC was carried out on a 250×4 mm RP-18 column (Merck, Germany) on a Merck-Hitachi HPLC apparatus with one pump (Model 655A-12) connected with a proportioning valve, a variable wavelength monitor (Model 655 A), a controller (Model L-5000), and an integrator (Model D-2000). Solvent: MeCN/0.1 M Et$_3$NH$^+$OAc$^-$ (35:65, v/v, pH 7.0).

Oligonucleotide Incorporation into Artificial Bilayers.

The incorporation of the oligonucleotides into artificial bilayers was performed at a lipid mixture of 1-palmitoyl-2- oleyl-sn-glycero-3-phosphoethanolamine (POPE) and 1-palmitoyl-2-oleyl-sn-glycero-3-phosphocholine (POPC) (8:2, w/w, 100 mg/ml of n-decane). For the preparation of the horizontal bilayers, planar slides (Ionovation GmbH, D-Osnabrück) were used. These slides contain chambers for cis- and trans compartments as well as electrode access (see FIG. 1). The main body of the slides contains of PTFE foil (thickness, 25 μm) with an aperture of ~100 μm diameter. This foil separates the chamber into the cis- and trans compartments which are only connected by the aperture. After filling of the chamber with buffer (250 mM KCl, 10 mM MOPS/TRIS, pH 7), the cis- and trans compartments were linked with Ag/AgCl electrodes—embedded in agarose/3 M KCl). Then, a soln. of the POPC/POPE lipid mixture (0.2 μl) is applied onto the aperture of the PTFE foil using a Hamilton syringe (Hamilton, CH-Bonaduz). A small Faraday cage shields the bilayer and the electrodes from HF-electrical noise. Next, a bilayer is made-up automatically using a perfusion system (Bilayer Explorer V01, Ionovation GmbH, D-Osnabrück). The formation of a stable bilayer was monitored both, optically using a laser scanning microscope (Insight Cell 3D, Evotec Technologies GmbH, D-Hamburg) as well as electrically by capacity measurements. When a stable bilayer had been obtained (capacity, 50-75 μF), the corresponding oligonucleotide soln. (50 nM, 4 μl) was injected into the cis compartment of the chip. During an incubation time of 25 min the intactness of the bilayer was electro-physiologically controlled using a head-stage EPC 10 USB with a patch clamp amplifier (software: Patchmaster, HEKA Elektronik Dr. Schulze GmbH, D-Lambrecht). The optical pictures of fluorescence fluctuations were obtained with a confocal laser scanning microscope (Insight Cell 3D, Evotec Technologies GmbH, D-Hamburg), equipped with a He—Ne laser (543 nm), a 40× water-immersion objective (UApo 340, 40×, NA=1.15, Olympus, 3-Tokyo), and an Avalanche photodiode detector (SPCM-AQR-13-FC, Perkin-Elmer Optoelectronics, Fremont, USA). Fluorescence irradiation was obtained with a laser power of 200±5 μW. 2D and 3D scans were performed by scanning the confocal spot in XY direction with a rotating beam scanner and movement of the objective in Z direction. The movement in both directions was piezo controlled which allows a nano-meter precise positioning. For the 2D pictures (Z-scans, FIGS. 2 and 3) the confocal plane was moved in 100 nm steps.

From the fluorescence signals of single molecules which pass the excitation volume, the diffusion constants can be calculated. In order to determine the diffusion times of the fluorescent oligonucleotides within and near the bilayer, they were measured at five different positions above, below and within the layer. At each point five measurements for 30 s, each, were taken. In summary, each measuring protocol was as follows: (i) a reference scan of the stable (empty) bilayer; (ii) addition of the sample with 25 min of incubation, followed by a scan series; (iii) additional scan series, each after a 1., 2., and 3. perfusion (60 s, each).

Preparation of Compounds i)

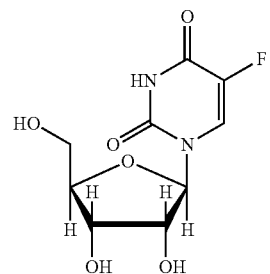

(1a)

5-Fluorouridine (1a) is commercially available from (TCI-Europe, B-Zwijndrecht).

ii) 5-Fluoro-1-((3aR,4R,6R,6aR)-6-(hydroxymethyl)-2,2-dimethyltetrahydrofuro[3,4-d][1,3]dioxol-4-yl)pyrimidine-2,4(1H,3H)-dione (19a)

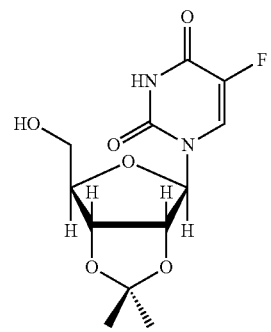

(19a)

Anhydrous 5-fluorouridine (1a, 1.0 g, 3.82 mmol, dried for 48 h at 75° C. over $CaCl_2$ under high vacuum) was suspended in dry acetone (200 ml). To this suspension polymer-linked p-toluene sulfonic acid (15.24 g, 38.1 mmol) was added, and the mixture was stirred at ambient temperature for 1 h. Subsequently, the polymer-bound acid was filtered off, and the filtrate was evaporated to a small volume, whereupon the crude product crystallized. This was filtered and recrystallized from $CHCl_3$/MeOH, 97:3, v/v) to give 1.12 g (97%) of pure 19a as colourless needles. TLC (silica gel, $CHCl_3$): $R_f$ 0.77. M.p. 196-197° C. $^1$H-NMR (($D_6$) DMSO): 11.866 (d, $^4$J(NH, F)=5.0, NH); 8.182 (d, $^3$J(F, H—C(6))=7.0, H—C(6)); 5.840 (d, $^3$J(H—C(1'), H—C(2'))=1.5, H—C(1')); 4.887 (dd, $^3$J(H—C(2'), H—C(1'))=2.5, $^3$J(H—C(2'), H—C(3'))=6.5, H—C(2')); 4.767 (dd, $^3$J(H—C(3'), H—C(4'))=3.5, $^3$J(H—C(3'), H—C(2'))=6.5, H—C(3')); 4.114 (ψq, $^3$J(H—C(4'), H—C(3'))=3.5, $^3$J(H—C(4'); $H_2$C(5'))=4.0, H—C(4')); 3.642 (dd, $^3$J($H_a$—C(5'), H—C(4'))=4.0, $^2$J($H_a$—C(5'), $H_b$—C(5'))=−12, $H_a$—C(5')); 3.588 (dd, $^2$J($H_b$—C(5') H—C(4'))=4.5, $^3$J($H_b$—C(5'), $H_a$—C(5'))=−12, $H_b$—C(5')), 1.493 (s, 3$H_{endo}$—C(α')), 1.296 (s, 3$H_{exo}$—C(α)). $^{13}$C-NMR (($D_6$) DMSO): 157.02 (d, $^2$J(C(4), F)=26.2, C(4)); 148.947 (C(2)); 139.898 (d, $^1$J(C(5), F)=230.14, C(5)); 125.782 (d, $^2$J(C(6), F)=34.6, C(6)); 112.91 (C(acetal)); 90.948 (C(1')); 86.502

(C(4')); 83.740 (C(2')); 80.215 (C(3')); 61.127 (C(5')); 26.982 ($C_{endo}(\alpha')$); 25.147 ($C_{exo}(\alpha)$). HR ESI MS: m/z calculated for $C_{12}H_{16}FN_2O_6$ (MH$^+$), 303.914. found m/z 305.10.

iii) 1-((3aR,4R,6R,6aR)-6-((Bis(4-methoxyphenyl) (phenyl)methoxy)methyl)-2,2-dimethyltetrahydrofuro[3,4-d][1,3]dioxol-4-yl)-5-fluoropyrimidine-2,4 (1H,3H)-dione (20)

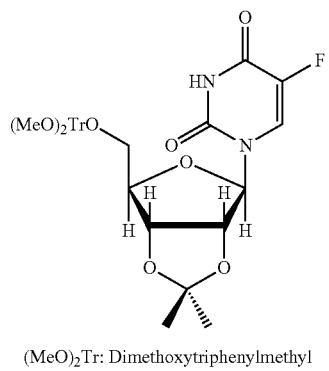

(20)

(MeO)$_2$Tr: Dimethoxytriphenylmethyl

Compound 19a (317.3 mg, 1.05 mmol) was dried by repeated evaporation with anhydr. pyridine and then dissolved in dry pyridine (6 ml). Then, 4,4'-dimethoxytriphenylmethyl chloride (397.5 mg, 1.15 mmol) was added, and the reaction mixture was stirred for 3 h under $N_2$ atmosphere at room temperature. Subsequently, the reaction was quenched by addition of 30 ml of a 5% aq. NaHCO$_3$ soln. The mixture was washed three times with CHCl$_3$ (50 ml, each), the combined organic layers were dried (Na$_2$SO$_4$), filtered and evaporated to dryness. The oily residue was chromatographed (silica gel, column: 6.5×13 cm, CHCl$_3$/MeOH, 98:2, v/v) to give 207 mg (32%) of colourless 20. TLC (silica gel, CHCl$_3$/MeOH, 98:2, v/v): $R_f$ 0.37. $^1$H-NMR ((D$_6$)DMSO): 11.891 (d, $^4$J(NH, F)=4.0, NH); 8.02 (d, $^3$J(F, H—C(6))=7.0, H—C(6)); 7.394-7.367, 7.305-7.205, 6.883-6.854 (3 m, 13H, H—C(trityl)); 5.840 (d, $^3$J(H—C(1'), H—C(2'))=1.5, H—C(1')); 4.969 (dd, $^3$J(H—C(2'), H—C(1'))=2.0, $^3$J(H—C(2'), H—C(3'))=6.5, H—C(2')); 4.685 (dd, $^3$J(H—C(3'), H—C(4'))=4.5, $^3$J(H—C(3'), H—C(2'))=6.0, H—C(3')); 4.143 ($\psi$q, $^3$J(H—C(4'), H—C(3'))=3.0, $^3$J(H—C(4'); H$_2$C(5'))=4.0, H—C(4')); 3.736, 3.732 (2 s, 2 OCH$_3$); 3.310 (dd, $^3$J(H$_a$—C(5'), H—C(4'))=6.9, $^2$J(H$_a$—C(5'), H$_b$—C(5'))=−10.5, H$_a$—C(5')); 3.120 (dd, $^2$J(H$_b$—C(5'), H—C(4'))=3.3, $^3$J(H$_b$—C(5'), H$_a$—C(5'))=−10.5, H$_b$—C(5')); 1.470 (s, 3H$_{endo}$—C($\alpha'$)), 1.268 (s, 3H$_{exo}$—C($\alpha$)). $^{13}$C-NMR ((D$_6$)DMSO): 158.054, 158.026 (2×C(5")); 156.90 (d, $^2$J(C(4), F)=26.2, C(4)); 148.775 (C(2)); 144.607 (C(7")); 139.849 (d, $^1$J(C(5), F)=231.4, C(5)); 135.99 (C(2"); 135.284, 135.225 (2×C(9")); 129.591, 129.533 (2×C(8")); 127.704, 127.540 (2×C(3")); 126.616 C(10")); 126.368 (d, $^2$J(C(6), F)=34.5, C(6)); 113.218 (C(acetal)); 113.102 (C(4")); 91.511 (C(1')); 85.690 (C(4')); 85.396 (C(1")); 83.483 (C(2')); 80.223 (C(3')); 63.737 (C(5')); 54.926, 54.905 (2×OCH$_3$); 26.898 ($C_{endo}$($\alpha'$)); 25.152 ($C_{exo}(\alpha)$). HR ESI MS: m/z calculated for $C_{33}H_{33}FN_2O_8$ (MH$^+$), 604.622. found m/z 604.481.

iv) 1-((2R,3R,4S,5R)-3,4-dihydroxy-5-(hydroxymethyl)tetrahydrofuran-2-yl)-5-fluoro-3-((2E,6E)-3,7,11-trimethyldodeca-2,6,10-trien-1-yl)pyrimidine-2,4 (1H,3H)-dione (23)

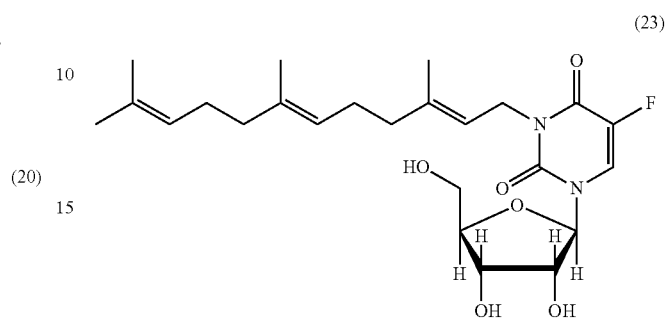

(23)

Anhydrous 5-fluorouridine (1a, 1.048 g, 4 mmol) was dissolved in anhydr. DMF (24 ml), and dry potassium carbonate (1.44 g, 10.64 mmol) was added. After stirring for 10 min at room temperature farnesyl bromide (1.4 ml, 4.4 mmol) was added dropwise under $N_2$ atmosphere. The reaction mixture was stirred for further 24 h at ambient temperature. Then, the potassium carbonate was filtered off and washed with dichloromethane. The filtrate was evaporated and dried over night in high vacuo. The residue was chromatographed (silica gel, 6.5×15 cm, CH$_2$Cl$_2$/MeOH, 9:1, v/v) to give compound 23 (0.78 g, 43%) as a colourless oil. TLC (silica gel, column: 6.5×15 cm, CH$_2$Cl$_2$/MeOH, 9:1, v/v): $R_f$ 0.57. UV (MeOH): $\lambda_{max}$, 267 nm ($\epsilon$, 8.800 M$^{-1}$ cm$^{-1}$). $^1$H-NMR ((D$_6$)DMSO): 8.381 (d, H—C(6))=7.0, H—C(6)); 5.787 (dd, $^3$J(H—C(1'), H—C(2'))=1.5, $^5$J(H—C(1'), F)=4.5, H—C(1')); 5.388 (d, $^3$J(HO—C(2'), H—C(2'))=5.0, HO—C(2')); 5.249 (t, $^3$J(HO—C(5'), H$_2$—C(5'))=4.5, HO—C(5')); 5.130 (t, $^3$J(H—C(2"), H—C(1"))=6.5, H—C(2")); 5.082 (m, 3H, $^3$J(HO—C(3'), H—C(3'))=5.5, HO—C(3'), H$_2$—C(1")); 4.407 (m, 2H, $^3$J=5.5, H—C(6"), H—C(10")); 4.043-3.977 (m, 2H, H—C(2'), H—C(3')); 3.871 ($\psi$quint., $^3$J(H—C(4'), H—C(3'))=5.0, $^3$J(H—C(4'), H$_2$C(5'))=2.5, H—C(4')); 3.704 (ddd, $^3$J(H$_a$—C(5'), H—C(4'))=4.5, $^2$J(H$_a$—C(5'), H$_b$—C(5'))=−12.0, $^3$J(H$_a$—C(5'), HO—C(5'))=2.5, H$_a$—C(5')); 3.592 (ddd, $^3$J(H$_b$—C(5'), H—C(4'))=5.0, $^2$J(H$_b$—C(5'), H$_a$—C(5'))=−12.0, $^3$J (H$_b$—C(5'), HO—C(5'))=3.0, H$_b$—C(5')); 2.057-1.888 (m, 8H, H$_2$—C(8"), H$_2$—C(9"), H$_2$—C(5"), H$_2$—C(4")); 1.741 (s, 3H, H—C(13")); 1.629 (s, 3H, H—C(14")); 1.548 (s, 3H, H—C(15")); 1.535 (s, 3H, H—C(12")). $^{13}$C-NMR ((D$_6$)DMSO): 156.073 (d, $^2$J(C(4), F)=26.2, C(4)); 148.931 (C(2)); 139.364 (d, $^1$J(C(5), F)=231.4, C(5)); 139.344 C(3")); 134.534 (C(7")); 130.537 (C(11")); 124.004 (C(6")); 123.432 (d, $^2$J(C(6), F)=35.0, C(6)); 118.170 (C(2")); 89.250 (C(4')); 84.550 (C(1')); 73.845 (C(3')); 69.028 (C(2')); 60.046 (C(5')); 39.108, 38.999, 38.838 (C(1"), C(4"), C(8")); 26.099 (C(5")), 25.645 (C(9")); 25.369 (C(12")); 17.426 (C(15")); 16.076 (C(13")); 15.706 (C(14")). HR ESI MS: m/z calculated for $C_{24}H_{36}FN_2O_6$ (MH$^+$), 466.543. found, 467.10; 335.2 (N(3)-farnesyl-5-fluorouracil). Anal calc. for $C_{24}H_{35}FN_2O_6$ (466.543): C, 61.79; H, 7.56; N, 6.00. Found: C, 61.53; H, 7.38; N, 5.86.

v) 5-Fluoro-1-((3aR,4R,6R,6aR)-6-(hydroxymethyl)-2,2-dimethyltetrahydrofuro-[3,4-d][1,3]dioxol-4-yl)-3-((2E,6E)-3,7,11-trimethyldodeca-2,6,10-trien-1-yl)pyrimidine-2,4(1H,3H)-dione (24)

vii) 5-Fluoro-1-((3aR,4R,6R,6aR)-6-(hydroxymethyl)-2,2-dipropyltetrahydrofuro-[3,4-d][1,3]dioxol-4-yl)-3-((2E,6E)-3,7,11-trimethyldodeca-2,6,10-trien-1-yl)pyrimidine-2,4(1H,3H)-dione (25)

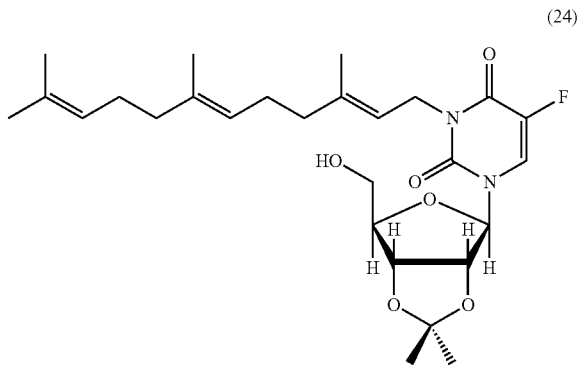
(24)

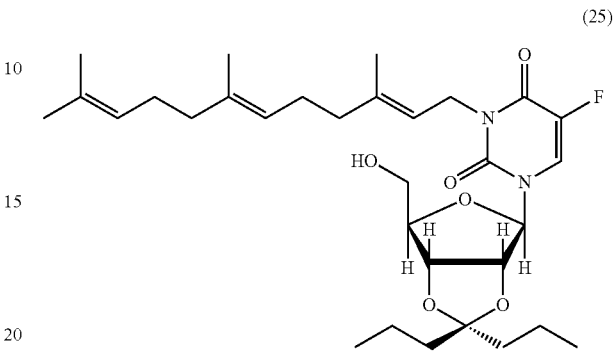
(25)

Compound 23 (0.25 g, 0.5 mmol) was suspended in anhydrous acetone and polymer-linked p-toluene sulfonic acid (1.0 g, 2.5 mmol) was added. The reaction mixture was stirred for 1 h at room temperature. The polymer-bound acid was filtered off, and the filtrate was evaporated and dried over night in high vacuo. Chromatographie (silica gel, column: 6.5×15 cm, CH$_2$Cl$_2$/MeOH, 95:5, v/v) gave, after evaporation of the main zone, compound 24 (780 mg, 43%) as colourless oil. TLC (silica gel, CH$_2$Cl$_2$/MeOH, 95:5, v/v): R$_f$ 0.57. UV (MeOH): λ$_{max}$, 267 nm (ε, 8.900 M$^{-1}$ cm$^{-1}$). HR ESI MS: m/z calculated for C$_{27}$H$_{40}$FN$_2$O$_6$ (MH$^+$), 507.61. found, 507.60; 335.2 (N(1)-farnesyl-5-fluorouracil).

vi) 5-Fluoro-2,3'-O-(1-propylbutylidene)uridine (19b)

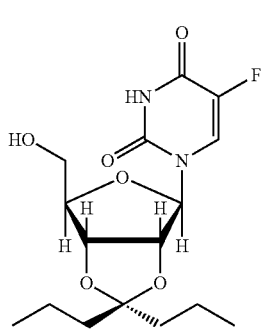
(19b)

For preparation and analysis of compound 19b see: E. Malecki, H. Rosemeyer, *Helv. Chim. Acta* 2010, 93, 1500.

5-Fluoro-2',3'-O-(1-propylbutylidene)uridine (19b) (358.3 mg, 1 mmol) was dissolved in anhydrous DMF (6 ml), and dry potassium carbonate (360 mg, 2.6 mmol) was added. After stirring for 10 min farnesyl bromide (0.35 mmol, 1.1 mmol) was added dropwise under N$_2$ atmosphere. Stirring at ambient temperature was continued for further 24 h. Subsequently, the potassium carbonate was filtered off and washed with CH$_2$Cl$_2$. The filtrate was evaporated and the residue was dried over night in high vacuo. Chromatography (silica gel, column: 6.5×15 cm, CH$_2$Cl$_2$, 95:5, v/v) gave compound 25 (285 mg, 51%) as colourless oil. TLC (silica gel, CH$_2$Cl$_2$/MeOH, 95:5, v/v): R$_f$ 0.71. UV (MeOH): λ$_{max}$, 267 nm (ε, 11.340 M$^{-1}$ cm$^{-1}$).

Anal. calc. for C$_{31}$H$_{47}$FN$_2$O$_6$ (562.713): C, 66.17; H, 8.82; N, 4.98. Found: C, 66.12; H, 8.39; N, 4.82.

viii) 5-Fluoro-1-((3aR,4R,6R,6aR)-6-(hydroxymethyl)-2,2-dinonyltetrahydrofuro[3,4-d][1,3]dioxol-4-yl)pyrimidine-2,4(1H,3H)-dione (19c)

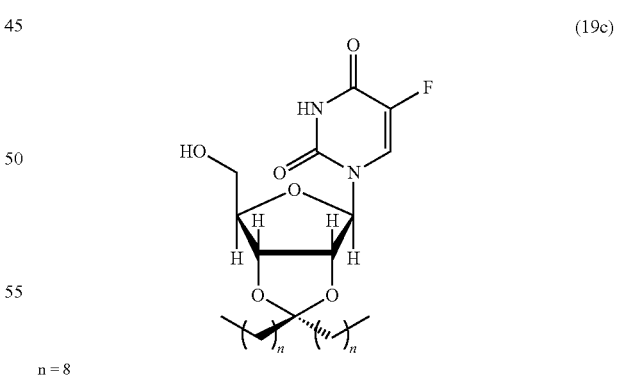
(19c)
n = 8

Anhydrous 5-fluorouridine (1a, 1.0 g, 3.82 mmol) was dissolved in anhydr. DMF (15 ml) and nonadecan-10-one (2.16 g, 7.64 mmol) was added. After addition of HC(OEt)$_3$ (1.0 g, 5.73 mmol) and 4M HCl in 1,4-dioxane (3.4 ml) the reaction mixture was stirred for 48 h at room temperature. Then the mixture was partitioned between CHCl$_3$ (350 ml) and a sat. aq. NaHCO$_3$ soln. (50 ml). The organic layer was washed three times with water (100 ml, each), and the aq. layers were re-extracted with CH$_2$Cl$_2$ (25 ml). The combined organic phases were dried (Na$_2$SO$_4$), filtered and evaporated. The residue was dried over night in high vacuum and then chromatographed (silica gel, column: 6×12 cm, CH$_2$Cl$_2$/MeOH, 95:5, v/v) to give compound 19c (1.38 g, 68%) as a colourless oil. TLC (silica gel, CH$_2$Cl$_2$/MeOH, 95:5, v/v): R$_f$ 0.56. UV (MeOH): $\lambda_{max}$, 265 nm (E, 9.860 M$^{-1}$ cm$^{-1}$). Anal. calc. for C$_{28}$H$_{47}$FN$_2$O$_6$ (526.681): C, 63.85; H, 8.99; N, 5.32. Found: C, 63.78; H, 8.80; N, 5.15.

ix) 2-Cyanoethyl-(((3aR,4R,6R,6aR)-6-(5-fluoro-2,4-dioxo-3,4-dihydropyrimidin-1(2H)-yl)-2,2-dinonyltetrahydrofuro[3,4-d][1,3]dioxol-4-yl)methyl) diisopropyl-Phosphoramidite (27)

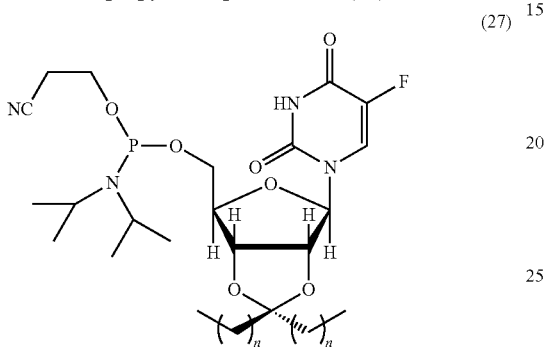

(27)

n = 8

Anhydrous compound 19c (205.4 mg, 0.39 mmol) was dissolved in dry CH$_2$Cl$_2$ (15 ml). Then, ethyldiisopropylamine (Hünig's base, 125 µl, 0.72 mmol) and (chloro)(2-cyanoethoxy)(diisopropylamino)phosphine (156 µl, 0.69 mmol) were added under N$_2$ atmosphere. The reaction mixture was stirred for 15 min at room temperature, and then an ice-cold 5% aq. NaHCO$_3$ solution (12 ml) was added. The mixture was extracted three times with cold CH$_2$Cl$_2$, the combined organic layers were dried (Na$_2$SO$_4$), filtered and evaporated on a rotary evaporator (bath temperature, 25° C.). Chromatography (silica gel, column: 2×8 cm, CH$_2$Cl$_2$/acetone, 8:2, v/v) gave one main zone from which compound 27 (210 mg, 74%) was obtained as colourless oil. TLC (MeOH/acetone, 8:2, v/v): R$_f$ 0.96. HR ESI MS: m/z calculated for C$_{37}$H$_{64}$FN$_2$O$_7$P (MH$^+$), 727.899. found, 727.658. $^{31}$P-NMR (CDCl$_3$): 150.73, 149.75.

x) 2-Cyanoethyl (((3aR,4R,6R,6aR)-6-(5-fluoro-2,4-dioxo-3-((2E,6E)-3,7,11-trimethyldodeca-2,6,10-trien-1-yl)-3,4-dihydropyrimidin-1(2H)-yl)-2,2-dipropyl-tetrahydrofuro[3,4-d][1,3]dioxol-4-yl)methyl) diisopropylphosphoramidite (26)

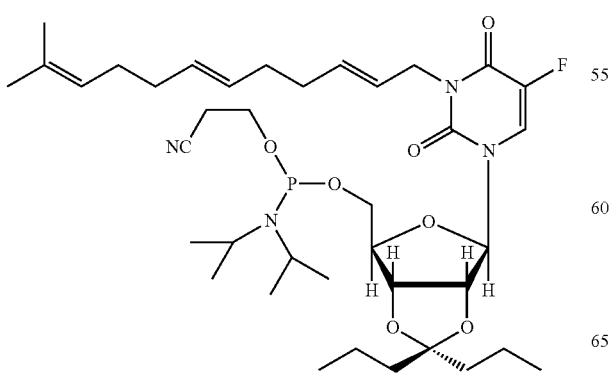

26

Anhydrous compound 25 (256 mg, 0.45 mmol) was 5'-phosphitylated using ethyldiisopropylamine (Hünig's base, 147 µl, 0.85 mmol) and (chloro)(2-cyanoethoxy)(diisopropylamino)phosphine (181 µl, 0.80 mmol) and worked up as described for compound 7. Chromatography (silica gel, column: 2×8 cm, CH$_2$Cl$_2$/MeOH, 8:2, v/v) gave one main zone from which compound 26 (208 mg, 60%) was obtained as colourless oil. TLC (CH$_2$Cl$_2$/MeOH, 8:2, v/v): R$_f$ 0.95. HR ESI MS: m/z calculated for C$_{40}$H$_{64}$FN$_4$O$_7$P (MH$^+$), 763.931. found, 763.65. $^{31}$P-NMR (CDCl$_3$): 149.86, 149.71.

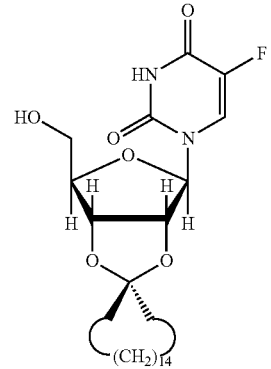

(21)

xi)

Compound 21 was prepared according to E. Malecki, H. Rosemeyer, Helv. Chim. Acta 2010, 93, 1500.

xii) 5-Fluoro-1-[(4'R,6R)-2,3,4,5'-tetrahydro-6'-(hydroxymethyl)spiro[cyclo-pentadecane-1,2'-furo[3,4-d][1,3]dioxol]-4'-yl]pyrimidine-2,4(1H,3H)-dione 2-Cyanoethyldiisopropylphosphoramidite (22)

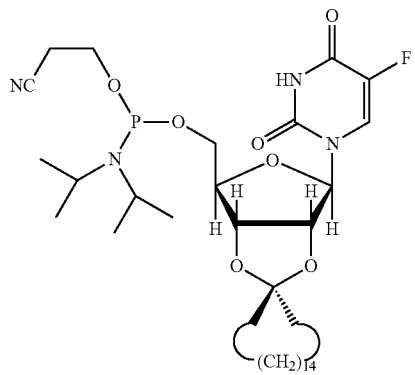

(22)

Anhydrous compound 21 (256 mg, 0.45 mmol) was 5'-phosphitylated using ethyldiisopropylamine (Hünig's base, 147 µl, 0.85 mmol) and (chloro)(2-cyanoethoxy)(diisopropylamino)phosphine (181 µl, 0.80 mmol) and worked up as described for compound 27. Chromatography (silica gel, column: 2×8 cm, CH$_2$Cl$_2$/MeOH, 8:2, v/v) gave one main zone from which compound 22 (208 mg, 60%) was obtained as colourless oil. TLC (CH$_2$Cl$_2$/MeOH, 8:2, v/v): R$_f$ 0.95. $^{31}$P-NMR (CDCl$_3$): 149.56, 149.41.

xiii) Compound 28a was prepared according to E. Malecki, H. Rosemeyer, *Helv. Chim. Acta* 2010, 93, 1500

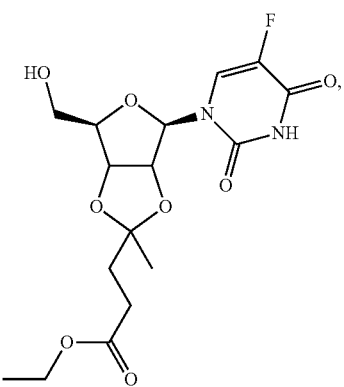

28a xiv) 2',3'-O-[(1R)-4-ethoxy-1-methyl-4-oxobutyl-idene]-5-fluoro-3-[(2E,6E)-3,7,11-trimethyldodeca-2,6,10-trien-1-yl]uridine (29a)

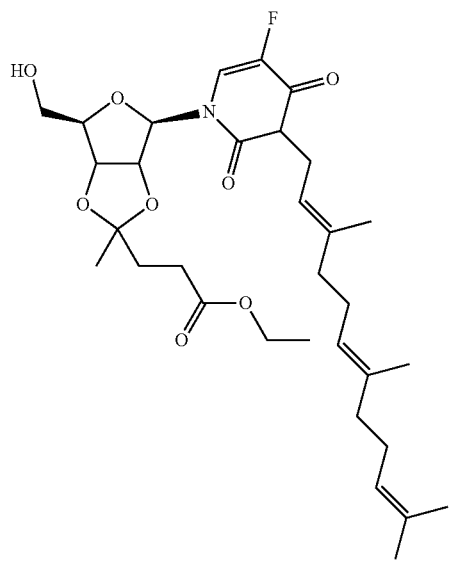

29a

The ester 28a (500 mg, 1.29 mmol) was dissolved in anhydr. DMF (11.5 ml). Under $N_2$ atmosphere $K_2CO_3$ (0.685 g, 4.97 mmol) were added and the mixture was stirred for 10 min at room temp. Then, farnesyl bromide (0.39 ml, 1.42 mmol) were added drop-wise during 2 h. After stirring overnight the reaction mixture was filtered, and the residue was washed with a small amount of $CH_2Cl_2$. The combined filtrates were evaporated to dryness in high vacuo over night. The oily residue was chromatographed on silica gel (column: 5×7.5 cm). Elution with $CH_2Cl_2$ (125 ml) followed by $CH_2Cl_2$/MeOH (95:5, v/v, 500 ml) afforded a main zone which was evaporated to give compd. 29a as a colourless oil.

TLC (silica gel, $CH_2Cl_2$/MeOH 95:5, v/v): $R_f$ 0.73. $^1$H-NMR ($D_6$-DMSO): 8.204 (d, $^3J$(H—C(6), F)=7.0, H—C(6)); 5.881 (d, $^3J$(1',2')=2.0, H—C(1')); 5.197 (t, $^3J$(HO—C(5'), H—C(5')=5.0, HO—C(5')); 5.126 (t, $^3J$(2",1")=7.5, H—C(2")); 5.043 (m, $H_2$—C(1")); 4.911 (dd, $^3J$(2',1')=3.5, $^3J$(2',3')=6.5, H—C(2')); 4.797 (dd, $^3J$(3',2')=6.5, $^3J$(3',4')=3.0, H—C(3')); 4.404-4.391 (m, 2H, H—C(6"), H—C(10")); 4.149 (m, H—C(4')); 4.057 (q, $^3J$=7.0, $CH_2$(ester)); 3.650-3.583 (m, $CH_2$(5')); 2.416 (t, $^3J$=7.0, $CH_2$—C=O); 2.051-1.887 (5 m, 10H, $H_2$—C(4"), $H_2$—C(5"), $H_2$—C(8"), $H_2$—C(9"), $CH_2$(ester)); 1.738 (s, $H_3$—C(13")); 1.629 (s, $H_3$—C(14")); 1.548 (s, $H_3$—C(15")); 1.533 (s, $H_3$—C(12")); 1.269 (s, $CH_3$(acetal)); 1.190 (t, $^3J$=7.0, $CH_3$(ester). $^{13}$C-NMR ($D_6$DMSO): 172.432 (C=O); 156.102 (d, $^2J$(C(4), F)=26.2, C(4)); 148.710 (C(2)); 139.354 (d, $^1J$(C(5), F)=228.9, C(5)); 139.382 (C(3")); 134.536 (C(7")); 130.550 (C(11")); 124.373 (d, $^2J$(C(6), F)=34.7, C(6)); 124.006 (C(6")); 123.486 (C(10")); 118.122 (C(2")); 113.623 (C(acetal)); 91.785 (C(1')); 86.564 (C(4')); 83.988 (C(2')); 80.224 (C(4')); 61.073 (C(5')); 59.823 ($CH_2$(ester)); ~38.0 (3 signals, superimposed by solvent signals, C(1"), C(4"), C(8")); 33.342 ($CH_2$—C=O); 28.103 ($CH_2$(acetal)); 26.108 (C(5")); 25.617 (C(9")); 25.369 (C(12")); 23.479 ($CH_3$(acetal)); 17.420 (C(15")); 16.089 (C(14")); 15.700 (C(13"); 13.968 ($CH_3$(ester)). HR ESI MS: m/z calculated for $C_{31}H_{46}FN_2O_8$ (MH$^+$), 593.696. found, 593.40; 335.2 [N(3)-farnesyl-5-fluorouracil].

xv)

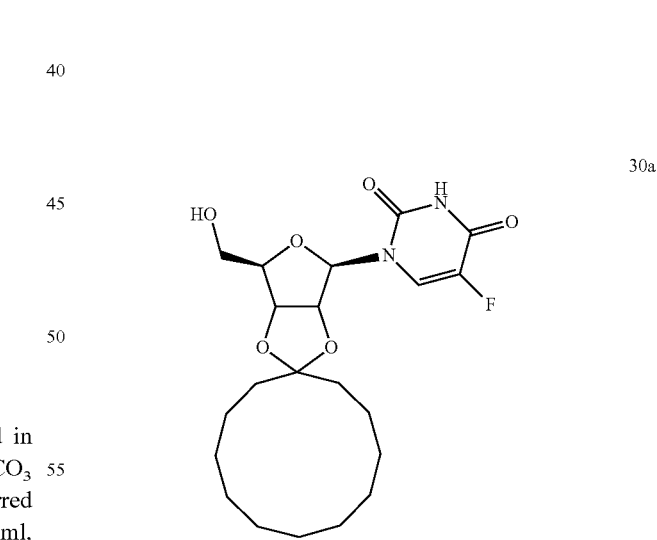

30a

Compound 30a was prepared according to E. Malecki, H. Rosemeyer, *Helv. Chim. Acta* 2010, 93, 1500.

xvi) 2',3'-O-Cyclododecane-1,1-diyl-5-fluoro-3-[(2E,6E)-3,7,11-trimethyldodeca-2,6,10-trien-1-yl]uridine (31a)

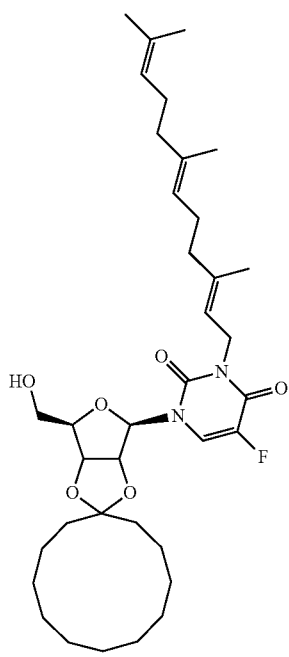

The ketal 30a (563.5 mg, 1.086 mmol) was dissolved in anhydr. DMF. Under $N_2$ atmosphere $K_2CO_3$ (390 mg, 2.82 mmol) were added, and the suspension was stirred for 10 min at room temperature. Then, farnesyl bromide (0.33 ml, 1.19 mmol) was added drop-wise within 2 h. After stirring over night the reaction mixture was filtered, and the solid residues was washed with a small amount of $CH_2Cl_2$. The combined filtrates were evaporated to dryness in high vacuo over night. The oily residue was chromatographed (silica gel, column: 6×10 cm). Elution with $CH_2Cl_2$/MeOH (97:3, v/v) gave a main zone from which compound 31a was isolated as a colourless oil (85%). TLC (silica gel, $CH_2Cl_2$/MeOH (97:3, v/v): $R_f$=0.57. $^1$H-NMR ($D_6$-DMSO): 8.240 (d, $^3J$(H—C(6), F)=7.0, H—C(6)); 5.901 (d, $^3J$(1',2')=2.4, H—C(1')); 5.20 (br. s., HO—C(5')); 5.126 (t, $^3J$(2",1")=6.6, H—C(2")); 5.041 (d, $^3J$(1",2")=6.0, $H_2$—C(1")); 4.848 (dd, $^3J$(2',1')=3.5, $^3J$(2',3')=6.5, H—C(2')); 4.754 (dd, $^3J$(3',2')=6.5, $^3J$(3',4')=3.0, H—C(3')); 4.405-4.392 (m, 2H, H—C(6"), H—C(10")); 4.137 (ψq, $^3J$(4',3')=3.5, $^3J$(4',5' and 5")=3.5, H—C(4')); 3.652-3.563 ((ψ octett, $^2J$(5',5")=−15, $H_2$—C(5')); 2.044-1.886 (4 m, $H_2$—C(8"), $H_2$—C(9"), $H_2$—C(5"), $H_2$—C(4")); 1.738 (m, 5H, $H_3$—C(13"), $2H_{endo}$—C(α')); 1.629 (s, $H_3$—C(14")); 1.562-1.533 (3 m, 8H, $H_3$C(15"), $H_3$—C(12"), $2H_{exo}$—C(α)); 1.448 (m, $2H_{endo}$—C(β')); 1.326-1.307 (m, 16H, 8×$H_2$—C(ketal)). $^{13}$C-NMR ($D_6$DMSO): 156.056 (d, $^2J$(C(4), F)=26.0, C(4)); 148.720 (C(2)); 139.367 (d, $^1J$(C(5), F)=228.9, C(5)); 139.321 (C(3")); 134.493 (C(7")); 130.492 (C(11")); 124.346 (d, $^2J$(C(6), F)=34.7, C(6)); 123.984 (C(6")); 123.586 (C(10")); 118.112 (C(2")); 117.025 (C(acetal)); 91.815 (C(1')); 86.656 (C(4')); 83.602 (C(2')); 80.076 (C(3')); 61.107 (C(5')); 38.953, 38.927, 38.271 (C(1"), C(4"), C(8")); 33.300 (C(a')); 30.301 (C(a)); 25.923 (C(5")); 25.430 (C(9")); 25.195 (C(12")); 17.218 (C(15")); 15.904 (C(14")); 15.500 (C(13")); 25.487, 25.372, 25.170, 24.972, 21.759, 21.522, 21.393, 19.623, 19.510 (9 $CH_2$). HR ESI MS: m/z calculated for $C_{36}H_{56}FN_2O_6$ (MH$^+$), 631.830. found, 631.50; 335.2 [N(3)-farnesyl-5-fluorouracil].

xvii) Coupling of Selected Nucleolipids of 5-Fluorouridine with ethyl 6,8,8-trimethyl-2-oxo-6,7,8,9-tetrahydro-2H-pyrano[3,2-g]quinoline-3-carboxylate-[9(6H)-yl]butanoate [=Atto-425 N(9)-butanoate](32)

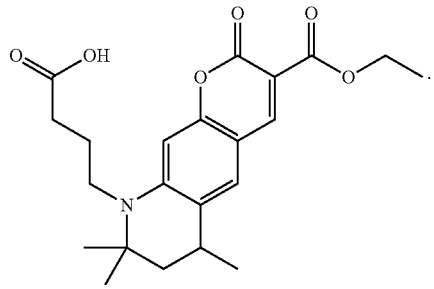

Atto-425 N(9)-butanoate

Five selected nucleolipid derivatives of 5-fluorouridine, carrying lipophilic moieties at the N(3) and/or at the O-2', 3'-position (19c, 28a-31a, formula scheme 10) have been labelled with the coumarine fluorophore Atto-425 ® which was coupled as N(9) butanoate to the 5'-hydroxyl of the corresponding nucleolipid. These compounds were prepared for subsequent determination of the cancerostatic activity of the corresponding nucleolipids. In this context, two further nucleolipids (29a and 31a) were prepared from precursors described in a preceding manuscript [E. Malecki, H. Rosemeyer, Helv. Chim. Acta 2010, 93, 1500]. Their farnesylation followed the protocol as described for compound 25 (scheme 6).

Coupling of 19c, 28a-31a with the fluorophore derivative was performed applying the Steglich reaction (DCC, dimethylaminopyridine). The products were purified by silica gel column chromatography and characterized by fluorescence spectroscopy as well as by HR ESI mass spectrometry.

The following scheme 10 shows the resulting derivatives which are connected to a fluorophore.

Scheme 10

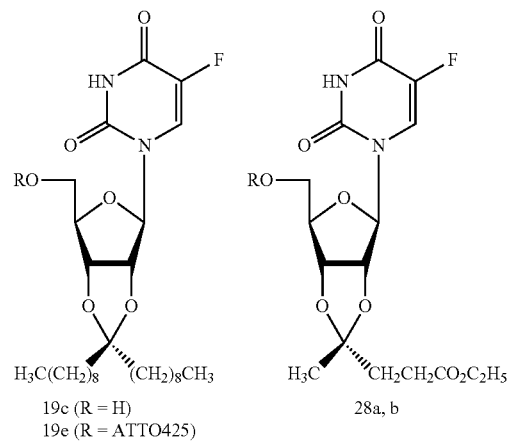

19c (R = H)
19e (R = ATTO425)

28a, b

41

-continued

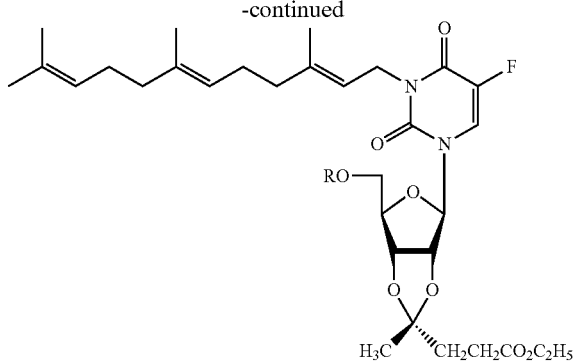

29a, b

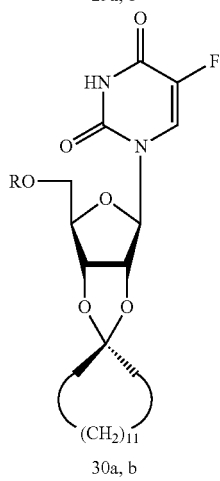

30a, b

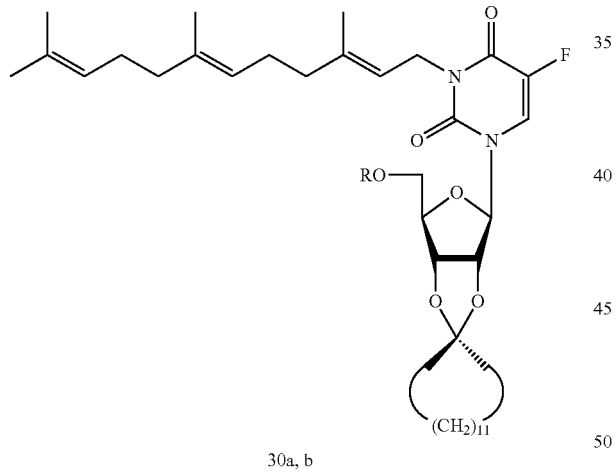

30a, b

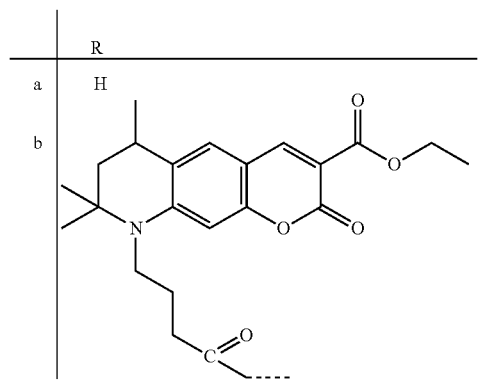

42

The Steglich esterifications were all performed in an analogous way but with slight modifications among each compound. The appropriate products were isolated as diastereoisomeric mixtures due to the stereogenic center at C(6) of the fluorophore.

xviii) 5'-O-{4-[3-Ethoxycarbonyl)-6,8,8-trimethyl-2-oxo-7,8-dihydro-2H-pyrano[3,2-g]quinolin-9(6H)-yl]butanoyl}-5-fluoro-2',3'-O-(1-nonyldecylidene) uridine (19e)

19e

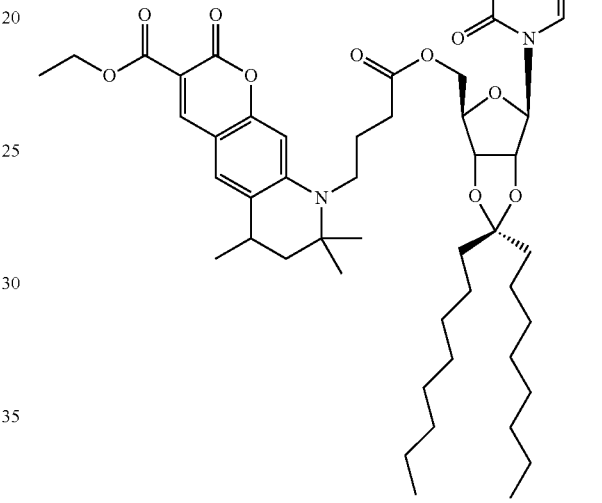

Atto-425 N(9)-butanoate (5 mg, 12.244 µmol) were dissolved in anhydrous $CH_2Cl_2$ (1.5 ml), and dimethylaminopyridine (DMAP, 0.6 mg, 0.01244 mmol), dissolved in $CH_2Cl_2$ (0.5 ml) and compd. 19c (6.55 mg, 12.44 µmol), dissolved in $CH_2Cl_2$ (1.3 ml) were added under $N_2$ atmosphere and cooling in an ice bath. Thereupon, dicyclohexylcarbodiimide (DCC, 2.57 mg, 12.44 mmol), dissolved in $CH_2Cl_2$ (0.11 ml) were added drop-wise over 45 min. After 5 min the soln. was allowed to warm up to ambient temp., and stirring was continued over night under exclusion of light. The reaction was monitored by TLC ($CH_2Cl_2$-MeOH, 93:7, v/v). After addition of further 30 mol-% of DMAP, DCC, as well as of compd. 2c stirring was continued for totally 48 h. The reaction mixture was evaporated in vacuo, and the residue was purified by repeated chromatography on silica gel 60 (column, 2×21.5 cm, $CH_2Cl_2$-MeOH, 98:2, v/v) to obtain compound 21b in quantitative yield as a green fluorescent solid (~13.3 mg). TLC (silica gel, $CH_2Cl_2$/MeOH, 93:7, v/v): $R_f$=0.88. HR ESI MS: m/z calculated for $C_{50}H_{72}FN_3O_{11}$, 910.119. found: 911.1 (MH$^+$), 932.9 (MNa$^+$), 630.4 (MNa$^+$-nonyldecylidene), 608.4 (MH$^+$-nonyldecylidene). Fluorescence spectroscopy: $\lambda_{max}$ (irradiation), 426 nm; $\lambda_{max}$ (emission), 465 nm.

xix) 5'-O-{4-[3-(Ethoxycarbonyl)-6,8,8-trimethyl-2-oxo-7,8-dihydro-2H-pyrano[3,2-g]quinolin-9(6H)-yl]butanoyl}-2',3'-O-[(1R)-4-ethoxy-1-methyl-4-oxobutylidene]-5-fluorouridine (28b)

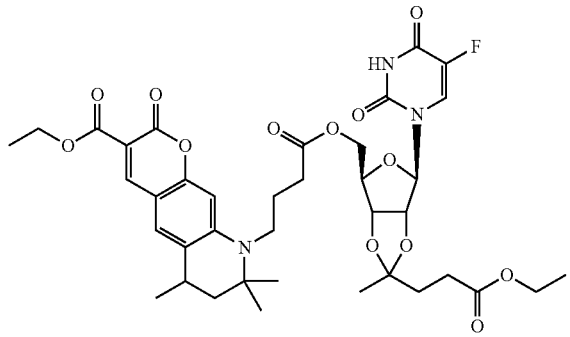

28b

Atto-425 N(9)-butanoate (5 mg, 12.244 μmol) were dissolved in anhydr. $CH_2Cl_2$ (1.5 ml), and dimethylaminopyridine (DMAP, 0.6 mg, 0.01244 mmol), dissolved in $CH_2Cl_2$ (0.5 ml) and compd. 28a (4.83 mg, 12.44 μmol) were added under $N_2$ atmosphere and cooling in an ice bath. Thereupon, dicyclohexylcarbo-diimide (DCC, 2.57 mg, 12.44 mmol), dissolved in $CH_2Cl_2$ (0.11 ml) were added drop-wise over 45 min. After 5 min the soln. was allowed to warm up to ambient temp., and stirring was continued over night under exclusion of light. The reaction was monitored by TLC ($CH_2Cl_2$-MeOH, 9:1, v/v). The product appeared as two fluorescent spots. After addition of further 30 mole-% of DMAP, DCC, as well as of compd. 28a stirring was continued for totally 48 h. The reaction mixture was evaporated in vacuo, and the residue was chromatographed on silica gel 60 (column, 2×15 cm, $CH_2Cl_2$-MeOH, 93:7, v(v) to obtain compound 28b in quantitative yield as a green fluorescent solid (~9.6 mg). TLC (silica gel, $CH_2Cl_2$/MeOH, 9:1, v/v): $R_f$=0.85 and 0.75. HR ESI MS: m/z calculated for $C_{38}H_{46}FN_3O_{13}$ ($MH^+$), 772.783. found, 772.82; 794.4 ($MNa^+$), 630.4 ($MNa^+$-ethyl levulinate), 449.4 ($MH^+$-Atto-425 N(9)-butanoate). Fluorescence spectroscopy: $\lambda_{max}$ (irradiation), 426 nm; $\lambda_{max}$ (emission), 462 nm.

xx) 5'-O-{4-[3-(Ethoxycarbonyl)-6,8,8-trimethyl-2-oxo-7,8-dihydro-2H-pyrano[3,2-g]quinolin-9(6H)-yl]butanoyl}-2',3'-O-[(1R)-4-ethoxy-1-methyl-4-oxobutylidene]-5-fluoro-3-[(2E,6E)-3,7,11-trimethyldodeca-2,6,10-trien-1-yl]uridine (29b)

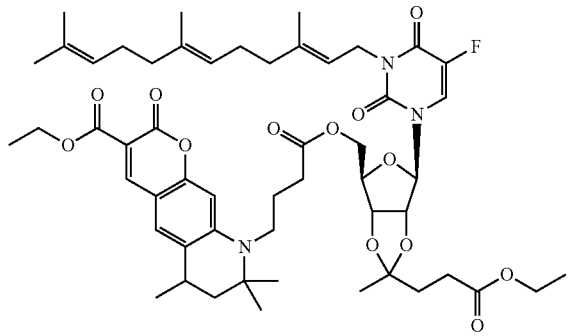

29b

Atto-425 N(9)-butanoate (5 mg, 12.244 μmol) were dissolved in anhydr. $CH_2Cl_2$ (1.5 ml), and dimethylaminopyridine (DMAP, 0.6 mg, 0.01244 mmol), dissolved in $CH_2Cl_2$ (0.5 ml) and compd. 29a (7.37 mg, 12.44 μmol), dissolved in $CH_2Cl_2$ (1.3 ml), were added under $N_2$ atmosphere and cooling in an ice bath. Thereupon, dicyclohexyl-carbodiimide (DCC, 2.57 mg, 12.44 mmol), dissolved in $CH_2Cl_2$ (0.11 ml) were added drop-wise over 45 min. After 5 min the soln. was allowed to warm up to ambient temp., and stirring was continued over night under exclusion of light. The reaction was monitored by TLC ($CH_2Cl_2$-MeOH, 95:5, v/v). After addition of further 30 mol-% of DMAP, DCC, as well as of compd. 29a stirring was continued for totally 48 h. The reaction mixture was evaporated in vacuo, and the residue was purified by repeated chromatography on silica gel 60 (column, 2×23 cm, $CH_2Cl_2$-MeOH, 96:4, v/v) to obtain compound 29b (7.7 mg, 63.4%) as a green fluorescent solid. TLC (silica gel, $CH_2Cl_2$/MeOH, 95:5, v/v): $R_f$=0.83 and 0.64. HR ESI MS: m/z calculated for $C_{53}H_{70}FN_3O_{13}$, 976.134. found: 976.6 ($MH^+$), 999.1 ($MNa^+$), 608.5 ($MH^+$-atto-425 N(9)-butanoate). Fluorescence spectroscopy: $\lambda_{max}$ (irradiation), 426 nm; $\lambda_{max}$ (emission), 460 nm.

xxi) 2',3'-O-Cyclododecane-1,1-diyl-5'-O-{4-[3-(ethoxycarbonyl)-6,8,8-trimethyl-2-oxo-7,8-dihydro-2H-pyrano[3,2-g]quinolin-9(6H)-yl]butanoyl}-5-fluorouridine (30b)

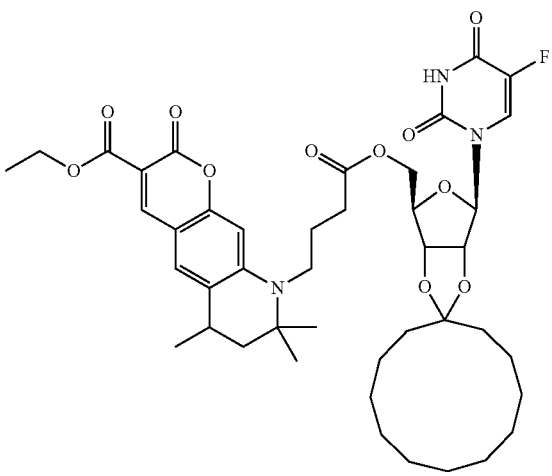

30b

Atto-425 N(9)-butanoate (5 mg, 12.244 μmol) were dissolved in anhydr. $CH_2Cl_2$ (1.5 ml), and dimethylaminopyridine (DMAP, 0.72 mg, 0.01244 mmol), dissolved in $CH_2Cl_2$ (0.6 ml) and compd. 30a (6.37 mg, 14.93 μmol), dissolved in $CH_2Cl_2$ (1.8 ml) were added under $N_2$ atmosphere and cooling in an ice bath. Because of the insufficient solubility of the reagents, MeCN (1 ml) was added. Thereupon, dicyclohexyl-carbodiimide (DCC, 3.08 mg, 14.93 mmol), dissolved in $CH_2Cl_2$ (0.13 ml), were added drop-wise over 45 min. After stirring for 5 min the soln. was allowed to warm up to ambient temp., and stirring was continued over night under exclusion of light. The reaction was monitored by TLC ($CH_2Cl_2$-MeOH, 93:7, v/v). After addition of further 10 mol-% of DMAP, DCC, as well as of compd. 30a stirring was continued for totally 48 h. The reaction mixture was evaporated in vacuo, and the residue was purified by chromatography on silica gel 60 (column, 2×15.5 cm, CH$_2$Cl$_2$-MeOH, 94:6, v/v) to obtain compound 30b (9.5 mg, 94.6%) as a green fluorescent solid. TLC (silica gel, CH$_2$Cl$_2$/MeOH, 93:7, v/v): R$_f$=0.84 and 0.75. HR ESI MS: m/z calculated for C$_{43}$H$_{56}$FN$_3$O$_{11}$, 809.917. found: 810.5 (MH$^+$), 832.5 (MNa$^+$), 630.5 (MNa$^+$-cyclododecanyl), 608.5 (MH$^+$-cyclododecanyl). Fluorescence spectroscopy: λ$_{max}$ (irradiation), 426 nm; λ$_{max}$ (emission), 460 nm.

xxii) 2',3'-O-Cyclododecane-1,1-diyl-5'-O-{4-[3-(ethoxycarbonyl)-6,8,8-trimethyl-2-oxo-7,8-dihydro-2H-pyrano[3,2-g]quinolin-9(6H)-yl]butanoyl}-5-fluoro-3-[(2E,6E)-3,7,11-trimethyldodeca-2,6,10-trien-1-yl]uridine (31b)

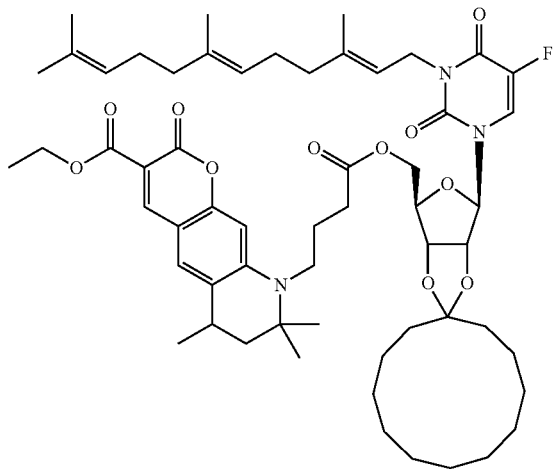

31b

Atto-425 N(9)-butanoate (5 mg, 12.244 μmol) were dissolved in anhydr. CH$_2$Cl$_2$ (1.5 ml), and dimethylaminopyridine (DMAP, 0.6 mg, 0.01244 mmol), dissolved in CH$_2$Cl$_2$ (0.5 ml) and compd. 31a (7.85 mg, 12.44 μmol), dissolved in CH$_2$Cl$_2$ (1.3 ml) were added under N$_2$ atmosphere and cooling in an ice bath. Thereupon, dicyclohexylcarbodiimide (DCC, 2.57 mg, 12.44 mmol), dissolved in CH$_2$Cl$_2$ (0.11 ml) were added drop-wise over 45 min. After 5 min the soln. was allowed to warm up to ambient temp., and stirring was continued over night under exclusion of light. The reaction was monitored by TLC (CH$_2$Cl$_2$-MeOH, 96:4, v/v). After addition of further 30 mol-% of DMAP, DCC, as well as of compd. 31a stirring was continued for totally 48 h. The reaction mixture was evaporated in vacuo, and the residue was purified by chromatography on silica gel 60 (column, 2×25.5 cm, CH$_2$Cl$_2$-MeOH, 98:2, v/v) to obtain compound 31b (10.9 mg, 86.6%) as a green fluorescent solid. TLC (silica gel, CH$_2$Cl$_2$/MeOH, 95:5, v/v): R$_f$=0.88 and 0.68. HR ESI MS: m/z calculated for C$_{58}$H$_{80}$FN$_3$O$_{11}$, 1014.268. found: 1015.3 (MH$^+$), 1036.7 (MNa$^+$), 630.4 (MNa$^+$-cyclododecanyl), 608.4 (MH$^+$-cyclododecanyl). Fluorescence spectroscopy: λ$_{max}$ (irradiation), 426 nm; λ$_{max}$ (emission), 460 nm.

xxiii) 5-Fluoro-1-((3aR,4R,6R,6aR)-6-(((4-methoxyphenyl)diphenylmethoxy)-methyl)-2,2-dipropyltetrahydrofuro[3,4-d][1,3]dioxol-4-yl)pyrimidin-2,4(1H,3H)-dione (3)

Compound 19b (0.5 g; 1.4 mmol) was evaporated trice from anhydrous pyridine and then dissolved in anhydrous pyridine (4 ml). The, 4'-methoxytriphenylmethyl chloride (0.53 g; 1.67 mmol) was added under N$_2$ atmosphere. The reaction mixture was stirred for 18 h at ambient temperature, and the reaction was then quenched by addition of MeOH (3.5 ml). After 10 min an ice-cold aqueous 5% NaHCO$_3$ soln. was added, and the mixture was extracted three times with CH$_2$Cl$_2$ (80 ml, each). The combined organic layers were dried for 30 min (Na$_2$SO$_4$), filtered, evaporated and dried in high vacuo yielding a colourless foam. Chromatography of the residue (silica gel 60H, column: 1×14 cm, CH$_2$Cl$_2$/MeOH, 97:3) afforded one main zone from which compound 3 (0.8 g, 91%) was isolated as a colourless foam. R$_f$ (CH$_2$Cl$_2$/MeOH, 97:3) 0.60. UV (MeOH): 270 (9,000). $^1$H-NMR ((D$_6$)DMSO): 11.86 (s, H—N(3)); 8.05 (d, $^3$J(H—C(6), F)=4.0, H—C(6)); 7.39-7.19 (m, H—C(3"), H—C (8"), H—C(9"), H—C(10")); 6.87 (d, $^3$J(H—C(4"), H—C (3"))=9.0, H—C(4")); 5.80 (s, H—C(1')); 4.99-4.97 (m, H—C(2')); 4.66-4.64 (m, H—C(3')); 4.17-4.14 (m, H—C (4')); 3.74 (s, OCH$_3$(6")); 3.34-3.31 (m, $^2$J(H$_a$—C(5'), H$_\beta$—C(5'))=-10.25, H$_2$—C(5')); 3.14-3.12 (m, $^2$J(H$_\beta$—C (5'), H$_\alpha$—C(5'))=-5.25, H$_2$—C(5')); 1.66-1.63 (m, H$_2$—C (a')); 1.50-1.47 (m, H$_2$—C(α)); 1.43-1.36 (m, H$_2$—C((β')); 1.28-1.21 (m, H$_2$—C((β)); 0.91 (t, $^2$J(H$_a$—C(γ'), H$_b$—C(γ'))=-7.5, (H$_a$—C(γ'), H$_c$—C(γ'))=-7.0, H$_3$—C(γ')); 0.85 (t, $^2$J(H$_a$—C(γ), H$_b$—C(γ))=-7.0, (H$_a$—C(γ), H$_c$—C(γ))=-7.5, H$_3$—C(γ)) $^{13}$C-NMR ((D$_6$)DMSO): 158.17 (C(5")); 156.99 (d, $^2$J(C(4), F)=-26.28, C(4)); 148.83 (C(2)); 144.05 (C(7"); 139.87 (d, $^1$J(C(5), F)=231.50, C(5)); 134.68 (C(2")); 129.89-127.35 (m, C(3"), C(8"), C(9"), C(10")); 126.82 (d, $^2$J(C(6), F)=-5.40, C(6)); 116.79 (C(Ketal)); 113.12 (C(4")); 91.85 (C(1")); 85.94 (C(4')); 85.62 (C(1')); 83.62 (C(2')); 80.66 (C(3')); 64.08 (C(5')); 54.92 (C(6")); 38.67 (C(α')); 38.55 (C(α)); 16.88 (C(β')); 16.27 (C(β)); 14.05 (C(γ')); 14.02 (C(γ)). Anal. calc. for C$_{36}$H$_{29}$FN$_2$O$_7$ (630.702): C, 68.56; H, 6.23; N, 4.44. Found: C, 68.85; H, 6.03; N, 4.23.

xxiv) 5-Fluoro-1-((3aR,4R,6R,6aR)-6-(((4-methoxyphenyl)diphenylmethoxy)-2,2-dipropyltetrahydrofuro[3,4-d][1,3]dioxol-4-yl)-3-((7R,11R)-3,7,11,15-tetramethylhexadec-2-en-1-yl)pyrimidin-2,4(1H, 3H)-dione (4a (E+Z))

Compound 3 (1 g; 1.59 mmol) was dissolved in anhydr. THF (10.6 ml). After addition of phytol (0.61 ml; 1.59 mmol) and Ph$_3$P (0.62 g; 2.38 mmol), the reaction mixture was stirred for 5 min at room temp. under N$_2$ atmosphere and with exclusion of light. Then, the reaction mixture was cooled to 0° C., and a 40% soln. of diethylazodicarboxylate (DEAD) in toluene (0.69 ml; 2.38 mmol) was added drop wise within 1 min. After further 5 min of stirring at 0° C. the mixture was allowed to warm up to room temp., and stirring was continued for 2 h. After evaporation of the solvent in high vacuo (45° C.) the residue was purified by repeated chromatography on silica gel (1. column: 2×25 cm, EtOAc/petrolether, 1:13; 2. column: 2×18 cm, EtOAc/petrolether, 15:75, each solvent with 1% of Et$_3$N). Yield 1.1 g (76%) of colourless foam. R$_f$ (EtOAc/petrol ether, 1:7) 0.55/0.60 (E/Z isomers). UV (MeOH): 270 (9,000). $^1$H-NMR ((D$_6$) DMSO: 8.16 (d, $^3$J(H—C(6)cis, F)=6.5, H—C(6)cis)); 8.25 (d, $^3$J(H—C(6)trans, F)=6.5, H—C(6)trans)); 7.38-7.21 (m, 12H, 2×H—C(3"), 4×H—C(8"), 4×H—C(9"), 2×H—C(10")); 6.84 (d, 2H, $^3$J(H—C(4"), H—C(3"))=9.0, 2×H—C(4")); 5.84 (s, H—C(1')); 4.99-4.97 (m, 2H, H—C(2'), H—C(2''')); 4.67-4.63 (m, H—C(3')); 4.36 (d, $^3$J(H—C(1''') cis, H—C(2''')cis)=5.0, H—C(1''')cis); 4.33 (d, $^3$J(H—C(1''') trans, H—C(2'''))=5.0, H—C(1''')trans); 4.21-4.18 (m, H—C(4')); 3.72 (s, 3H, H$_3$—C(6")); 3.35-3.32 (m, H$_\alpha$—C (5')); 3.15-3.09 (m, H$_\beta$—C(5')); 2.07 (t, 2H, $^3$J(H—C(4''') cis, H—C(5'''))=7.5, H—C(4''')cis); 1.87 (t, 2H, $^3$J(H—C(4''')trans, H—C(5'''))=7.5, H—C(4''')trans); 1.67 (s, 3H, H$_3$—C(20''')); 1.66-1.63 (m, 2H, H$_2$—C($\alpha$')); 1.51-1.43 (m, 3H, H$_2$—C($\alpha$), H—C(15''')); 1.42-1.30 (m, 6H, H$_2$—C($\beta$'), H$_2$—C(5'''), H—C(7'''), H—C(11''')); 1.28-0.98 (m, 16H, H$_2$—C(($\beta$), H$_2$—C(6'''), H$_2$—C(8'''), H$_2$—C(9'''), H$_2$—C(10'''), H$_2$—C(12'''), H$_2$—C(3'''), H$_2$—C(4''')); 0.91 (t, 3H, $^2$J(H$_a$—C($\gamma$'), H$_b$-CM), ((H$_a$—C($\gamma$'), H$_c$—C($\gamma$')))=−7.0, H$_3$—C($\gamma$')); 0.84 (t, 3H, $^2$J((H$_a$—C($\gamma$), H$_b$—C($\gamma$)), ((H$_a$—C($\gamma$), H$_c$—C($\gamma$)))=−7.0, H$_3$—C($\gamma$)). 0.83-0.78 (m, 12H, H$_3$—C(16'''), H$_3$—C(17'''), H$_3$—C(18'''), H$_3$—C(19''')). $^{13}$C-NMR ((D$_6$)DMSO): 158.15 (C(5'')); 156.09 (d, $^2$J(C(4), F)=−25.78, C(4); 148.60 (d, $^4$J(C(2), F)=6.28, C(2)); 144.03 (C(7'')); 139.35 (d, $^1$J(C(5), F)=229.76, C(5)); 139.84 (s, C(3''')cis; 139.56 (s, C(3''')trans); 134.67 (C(2'')); 129.86-126.74 (m, C(3''), C(8''), C(9''), C(10'')); 125.55 (d, $^2$J(C(6), F)=−32.82, C(6)); 117.83 (C(2'')); 116.71 (C(Ketal)); 113.05 (C(4')); 93.22 (C(4')); 86.33 (C(1'')); 85.95 (C(1')); 83.74 (C(2')); 80.82 (C(3')); 64.13 (C(5')); 54.88 (C(6'')); 39.00 (C(1''')); 38.66 (C($\alpha$')); 38.54 (C($\alpha$)); 36.65-36.51 (m, C(6'''), C(8'''), C(10'''), C(12''')); 35.81, 35.70 (2s, C(7'''), C(11''')); 27.25 (C(15''')); 24.27 (C(5''')); 24.01 (C(9''')); 23.62 (C(13''')); 22.41, 22.32 (2s, C(16'''), C(17''')); 19.48, 19.43 (2s, C(18'''), C(19''')); 16.88 (C($\beta$')); 16.27 (C($\beta$)); 15.85 (C(20''')); 14.05 (C($\gamma$')); 14.02 (C($\gamma$)). Anal. calc for C$_{56}$H$_{77}$FN$_2$O$_7$ (909.218): C, 73.98; H, 8.54; N, 3.08. Found: C, 73.75; H, 8.57; N, 2.73.

xxv) 3-((Z)-3,7-Dimethylocta-2,6-dien-1-yl)-5-fluoro-1-((3aR,4R,6R,6aR)-6-(((4-methoxyphenyl)diphenylmethoxy)methyl)-2,2-dipropyl-tetrahydro-furo-[3,4d][1,3]dioxol-4-yl)pyrimidin-2,4(1H,3H)-dione (4b)

Compound 3 (1 g; 1.59 mmol) was dissolved in anhydrous THF (11 ml) and reacted with nerol (0.28 ml; 1.59 mmol), Ph$_3$P (0.62 g; 2.38 mmol) and diethylazodicarboxylate (40% in toluene, 0.69 ml; 2.38 mmol) as described for compd. 4a. The purification of the raw product was performed by chromatography (silica gel 60, column: 2×30 cm, EtOAc/petrolether 1:13, containing 1% of Et$_3$N). From the main zone compd. 4b (0.98 g, 79%) was isolated as a colourless oil upon evaporation of the solvent. R$_f$ (EtOAc/petrol ether, 1:7) 0.42. UV (MeOH): 270 (11,500).

$^1$H-NMR ((D$_6$)DMSO): 8.15 (d, $^3$J(H—C(6), F)=6.0, H—C(6)); 7.38-7.20 (m, 12H, H—C(3''), H—C(8''), H—C(9''), H—C(10'')); 6.85 (d, 2H, $^3$J(H—C(4''), H—C(3''))=9.0, 2×H—C(4'')); 5.84 (s, H—C(1')); 5.12 (t, $^3$J(H—C(2'''), H—C(1'''))=6.0, H—C(2''')); 5.01-5.00 (2s, 2H, H—C(2'), H—C(6''')); 4.66 (t, $^3$J(H—C(3'), H—C(4'))=4.5, H—C(3')); 4.30 ($\psi$quint, 2H, $^3$J(H$_2$—C(1'''), H—C(2'''))=7.5, H$_2$—C(1''')); 4.22-4.20 (m, H—C(4')); 3.73 (s, 3H, H$_3$—C(6'')); 3.35-3.31 (m, H$_\alpha$—C(5')); 3.13-3.11 (m, H$_\beta$—C(5')); 2.14-2.05 (m, 4H, H$_2$—C(4'''), H$_2$—C(5''')); 1.67-1.59 (m, 11H, H$_2$—C($\alpha$'), H$_3$—C(8'''), H$_3$—C(9'''), H$_3$—C(10''')); 1.50-1.46 (m, 2H, H$_2$—C($\alpha$)); 1.43-1.41 (m, 2H, H$_2$—C($\beta$')); 1.27-1.22 (m, (m, 2H, H$_2$—C($\beta$)); 0.92 (t, 3H, $^2$J((H$_a$—C($\gamma$'), H$_b$—C($\gamma$')), ((H$_a$—C($\gamma$'), H$_c$—C($\gamma$')))=−7.0, H$_3$—C($\gamma$')); 0.87 (t, 3H, $^2$J(H$_a$—C($\gamma$), H$_b$—C($\gamma$)), ((H$_a$—C($\gamma$), H$_c$—C($\gamma$)))=−7.0, H$_3$—C($\gamma$)). $^{13}$C-NMR ((D$_6$)DMSO): 158.16 (C(3'')); 156.13 (d, $^2$J(C(4), F)=−25.09, C(4)); 148.64 (C(7'')); 144.05 (d, $^4$J(C(2), F)=25.09, C(2)); 148.64 (C(7'')); 144.05 (d, $^2$J(C(5), F)=229.6, C(5)); 139.37 (C(3''')); 134.70 (C(2'')); 131.06 (C(7'')); 129.88-126.77 (m, C(3''), C(8''), C(9''), C(10'')); 125.69 (d, $^1$J(C(6), F)=32.57, C(6)); 123.84 (C(2''')); 118.78 (C(6''')); 116.69 (C(Ketal)); 113.07 (C(4'')); 93.41 (C(4')); 86.19 (C(1'')); 85.95 (C(1')); 83.76 (C(2')); 80.86 (C(3')); 64.22 (C(5')); 54.89 (C(6'')); 38.93 (C(1''')); 38.69 (C($\alpha$')); 38.54 (C($\alpha$)); 31.56 (C(4''')); 26.27 (C(5''')); 25.37 (C(9''')); 22.85 (C(10''')); 17.39 (C(8'')); 16.90 (C($\beta$')); 16.24 (C($\beta$)); 14.02 (C($\gamma$'), C($\gamma$)). Anal. calc. for C$_{46}$H$_{55}$FN$_2$O$_7$*0.5 C$_6$H$_{12}$ (809.0164): C, 72.68; H, 7.54: N, 3.46. Found: C, 72.48; H, 7.43; N, 3.28.

xxvi) 5-Fluoro-1-((3aR,4R,6R,6aR)-6-(hydroxymethyl)-2,2-dipropyl-tetrahydrofuro[3,4-d][1,3]dioxol-4-yl)-3-((7R,11R)-3,7,11,15-tetramethylhexadec-2-en-1-yl)pyrimidin-2,4(1H, 3H)-dion (5a (E+Z))

Compound 4a (E+Z) (200 mg; 0.22 mmol) was dissolved in CH$_2$Cl$_2$ (4.5 ml). Then, 4.5 ml of a 4% soln. of a dichloroaceric acid in CH$_2$Cl$_2$ was added drop wise. The reaction mixture was stirred for 10 min at ambient temp. and then washed with H$_2$O until the aqueous reacts neutral. The layers were separated by centrifugation, and the organic phase was evaporated to dryness. The residue was dissolved in a small volume of EtOAc, adsorbed to a small amount of silica gel and applied on the top of a chromatography column (silica gel, column: 2×15 cm, EtOAc/petrol ether, 1:4). From the main zone compd. 5a (87 mg, 62%). R$_f$ (EtOAc/petrol ether, 1:4) 0.41. UV (MeOH): 270 (10,600).

$^1$H-NMR ((D$_6$) DMSO): 8.23 (d, $^3$J(H—C(6), F)=6.5, H—C(6)); 5.89 (s, H—C(1')); 5.18-5.11 (m, 2H, H—C(5'), H—C(2'')); 4.90-4.88 (m, 2H, H—C(2'), H—C(2'')); 4.78-4.76 (m, H—C(3')); 4.40 (d, $^3$J(H—C(1'')cis, H—C(2''))=5.0, H—C(1'')cis); 4.39 (d, $^3$J(H—C(1'')trans, H—C(2''))=5.0, H—C(1'')trans); 4.15-4.14 (m, H—C(4')); 3.62-3.60 (m, H$_\alpha$—C(5')); 3.59-3.57 (m, H$_\beta$—C(5')); 2.12 (t, 2H, $^3$J(H—C(4'')cis, H—C(5''))=7.5, H—C(4'')cis); 1.92 (t, 2H, $^3$J(H—C(4'')trans, H—C(5''))=7.5, H—C(4'') trans); 1.71 (s, 3H, H$_3$—C(20'')); 1.68-1.65 (m, 2H, H$_2$—C($\alpha$')); 1.53-1.47 (m, 3H, H$_2$—C($\alpha$), H—C(15'')); 1.46-1.31 (m, 6H, H$_2$—C($\beta$'), H$_2$—C(5''), H—C(7''), H—C(11'')); 1.29-1.04 (m, 16H, H$_2$—C(($\beta$), H$_2$—C(6''), H$_2$—C(8''), H$_2$—C(9''), H$_2$—C(10''), H$_2$—C(12''), H$_2$—C(13''), H$_2$—C(14'')); 0.91 (t, 3H, $^2$J(H$_a$—C($\gamma$'), H$_b$—C($\gamma$')), (H$_a$—C($\gamma$'), H$_c$—C($\gamma$'))=−7.5, H$_3$—C($\gamma$')); 0.86 (t, 3H, $^2$J(H$_a$—C($\gamma$), H$_b$—C($\gamma$)), (H$_a$—C($\gamma$), H$_c$—C($\gamma$))=−7.5, H$_3$—C($\gamma$)); 0.85-0.80 (m, 12H, H$_3$—C(16''), H$_3$—C(17''), H$_3$—C(18''), H$_3$—C(19'')). $^{13}$C-NMR ((D$_6$) DMSO): 157.88 (d, $^2$J(C(4), F)=−46.38, C(4)); 148.71 (d, $^4$J(C(2), F)=3.77, C(2)); 139.33 (d, $^1$J(C(5), F)=228.75, C(5)); 140.04 (s, C(3'')cis); 139.64 (s, C(3'')trans); 124.50 (d, $^2$J(C(6), F)=−34.58, C(6)); 118.68 (s, C(2'')cis); 117.95 (s, C(2'')trans); 116.37 (C(Ketal)); 92.05 (C(4')); 86.88 (C(1')); 84.07 (C(2')); 80.52 (C(3')); 61.16 (C(5')); 38.71 (C(1'')); 38.59 (C($\alpha$')); 38.53 (C($\alpha$)); 36.59-36.50 (m, C(6''), C(8''), C(10''), C(12'')); 35.79, 35.68 (2s, C(7''), C(11'')); 27.25 (C(15'')); 24.23 (C(5'')); 24.23 (C(9'')); 24.00 (C(13'')); 22.43, 22.34 (2s, C(16''), C(17'')); 19.50, 19.45 (2s, C(18''), C(19'')); 16.91 (C(13')); 16.24 (C($\beta$)); 15.94 (C(20'')); 14.06 (C($\gamma$')); 14.02 (C($\gamma$)). Anal. calc. for C$_{36}$H$_{61}$FN$_2$O$_6$ (636.878): C, 67.89; H, 9.65; N, 4.40. Found: C, 67.61; H, 9.79; N, 4.29. log P=+12.5±0.63.

xxvii) 3-((Z)-3,7-Dimethylocta-2,6-dien-1-yl)-5-fluoro-1-((3aR,4R,6R,6aR)-6-(hydroxymethyl)-2,2-dipropyltetrahydrofuro[3,4-d][1,3]dioxol-4-yl)pyrimidin-2,4(1H,3H)-dione (5b)

Compound 4b (1.25 g; 1.63 mmol) was detritylated and purified as described for compd. 5a. Column chromatography (silica gel, column: 2×7.5 cm, EtOAc/petrol ether, 1:4) gave one main zone from which compd. 5b (0.528 g, 66%)

was obtained as a colourless oil) upon evaporation of the solvent. $R_f$(EtOAc/petrol ether, 1:4) 0.25. UV (MeOH): 270 nm (E=9900). $^1$H-NMR ((D$_6$)DMSO): 8.23 (d, $^3$J(H—C(6), F)=7.0, H—C(6)); 5.90 (s, H—C(1')); 5.18-5.13 (m, 3H, H—C(2'), H—C(2''), H—C(6'')); 4.90-4.88 (m, H—OC(5')); 4.77-4.75 (m, H—C(3')); 4.40 (d, 2H, $^3$J(H$_2$—C(1''), H—C(2''))=7.0, H$_2$—C(1'')); 4.15 (q, $^3$J((H—C(4'), (H—C(4'), H$_2$—C(5'))=3.5, H—C(4')); 3.62-3.57 (m, 2H, H$_2$—C(5')); 2.18-2.06 (m, 4H, H$_2$—C(4''), H$_2$—C(5'')); 1.68-1.66 (m, 8H, H$_2$—C($\alpha$'), H$_3$—C(9''), H$_3$—C(10'')); 1.59 (s, 3H, H$_3$—C(8'')); 1.53-1.49 (m, 2H, H$_2$—C($\alpha$)); 1.44-1.39 (m, 2H, H$_2$—C(($\beta$'))); 1.30-1.52 (m, 2H, (m, 2H, H$_2$—C($\beta$)); 0.93 (t, 3H, $^2$J(H$_a$—C($\gamma$'), H$_b$—C($\gamma$')), ((H$_a$—C($\gamma$'), H$_c$—C($\gamma$')))=−7.0, H$_3$—C($\gamma$')); 0.91 (t, 3H, $^2$J(H$_a$—C($\gamma$), H$_b$—C($\gamma$)), (H$_a$—C($\gamma$), H$_c$—C($\gamma$)))=−7.0, H$_3$—C($\gamma$)). $^{13}$C-NMR ((D$_6$)DMSO): 156.10 (d, $^2$J (C(4), F)=−25.65, C(4)); 148.73 (C(2)); 139.35 (d, $^2$J(C(5), F)=228.76, C(5)); 139.52 (C(3'')); 131.06 (C(7'')); 124.48 (d, $^1$J(C(6), F)=34.83, C(6)); 123.84 (C(2'')); 118.93 (C(6'')); 116.38 (C(Ketal)); 92.07 (C(4')); 86.89 (C(1')); 84.10 (C(2')); 80.54 (C(3')); 61.20 (C(5')); 38.73 (C(a')); 38.60 (C(a)); 31.56 (C(4'')); 25.93 (C(5'')); 25.36 (C(9'')); 22.87 (C(10'')); 17.39 (C(8''); 16.92 (C((Y))); 16.24 (C(13)); 14.02 (C($\gamma$')); 13.97 (C($\gamma$)). Anal. calc. for $C_{26}H_{39}FN_2O_6$ (494.596): C, 63.14; H, 7.95; N, 5.66. Found: C, 63.08; H, 8.13; N, 5.69. Log P=+7.65±0.65.

xxviii) 2-Cyanoethyl(((3aR,4R,6R,6aR)-6-(5-fluodo-2,4-dioxo-3-((7R,11R)-3,7,11,15-tetramethyl-hexadec-2-en-1-yl)-3,4-dihydropyrimidin-1(2H)-yl)-2,2-dipropyl-tetrahydrofuro-[3,4-d][1,3]dioxol-4-yl)methyl)diisopropyl-phosphoramidite (6a (E+Z))

Compound 5a (E+Z) (0.2 g; 0.314 mmol) was evaporated three times from anhydr. CH$_2$Cl$_2$ and then dissolved in anhydr. CH$_2$Cl$_2$ (12 ml). Thereupon, diisopropylethylamine (Hünig' base, 101.5 µl; 0.597 mmol) and 2-cyanoethyl-diisopropylchlorophosphine (126 µl; 0.565 mmol) were added under N$_2$ atmosphere. The reaction mixture was stirred at room temp. for exactly 15 min. After addition of an ice-cold 5% aq. NaHCO$_3$ soln. (10 ml) the mixture was extracted three times with CH$_2$Cl$_2$ (5 ml, each). The combined organic layers were dried over Na$_2$SO$_4$ for 1 min under N$_2$ atmosphere and with cooling. After filtration the solution was evaporated to dryness. The residue was flash-chromatographed (silica gel, column: 2×10 cm, CH$_2$Cl$_2$/acetone, 85:15) within app. 20 min. Evaporation of the main zone afforded compd. 6a (0.178 g, 68%) as a colourless oil upon evaporation of the solvent. $R_f$ (CH$_2$Cl$_2$/acetone, 85:15): 0.96. $^{31}$P-NMR (CDCl$_3$): 149.93; 149.75.

xxix) 2-Cyanoethyl(((3aR,4R,6R,6aR)-6-(3-((Z)-3,7-dimethylocta-2,6-dien-1-yl)-5-fluoro-2,4-dioxo-3,4-dihydropyrimidin-1(2H)-yl)-2,2-dipropyl-tetrahydrofuro-[3,4-d][1,3]dioxol-4-yl)methyl)diisopropylphosphoramidit (6b)

Compound 5b (0.2 g; 0.405 mmol) was phosphitylated and purified as described for compd. 5a. Yield: 255 mg (91%) of compd. 6b as colourless oil. $R_f$ (CH$_2$Cl$_2$/acetone, 85:15): 0.96. $^{31}$P-NMR (CDCl$_3$): 149.84; 149.66.

xxx) Synthesis and Bilayer Incorporation

The phosphoramidite 27 was used to prepare the following oligonucleotides with an appending nucleolipid 19c:

```
5'-d(19c-Cy5-TAG GTC AAT ACT)-3'        33

5'-d(19c-TAG GTC AAT ACT)-3'            34

3'-d(ATC CAG TTA TGA)-5'                35
```

The cyanine-5—labelled oligomer 33 was used to study the incorporation efficiency of lipid bilayer incorporation with respect to velocity and stability. The oligomer 34 was used to study the duplex formation between this lipooligo-nucleotide and its complementary strand 35 at the lipid bilayer—water phase boundary layer using SYBR Green as intercalating fluorescent dye.

xxxi) Small-Scale Labelling of Compound 19c with the N-Hydroxysuccinimide Ester of Eterneon 480® (→36)

Eterneon 480® (5 mg; 0.0095 mmol) and compd. 19c (5.3 mg; 0.0095 mmol) were both dissolved in MeCN (1.5 ml, each). The soln. of 19c was added dropwise to the fluorophore soln. under N$_2$ atmosphere and under exclusion of light within 5 min. The reaction mixture was stirred for 26 h at ambient temperature. The product was purified by chromatography (silica gel, column: 2×19 cm, CH$_2$Cl$_2$/MeOH, 99:1). The isolated product 36 forms a deep red solid. $R_f$ (CH$_2$Cl$_2$/MeOH, 99:1) 0.5.

Scheme 11

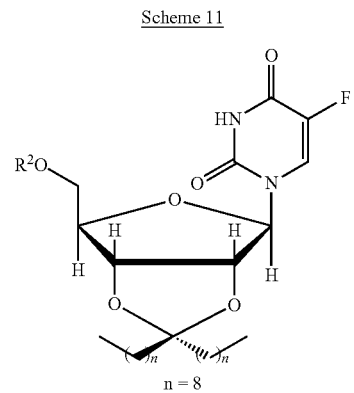

| | R$^2$ |
|---|---|
| 19c | H |
| 36 | Eterneon-480 | xxxii) 5-Fluoro-1((3aR,4R,6R,6aR)-6-(hydroxymethyl)-2,2-dipentadecanyl-tetrahydro-furo[3,4-d][1,3]dioxol-4-yl)pyrimidine-2,4(1H,3H)-done (19d)

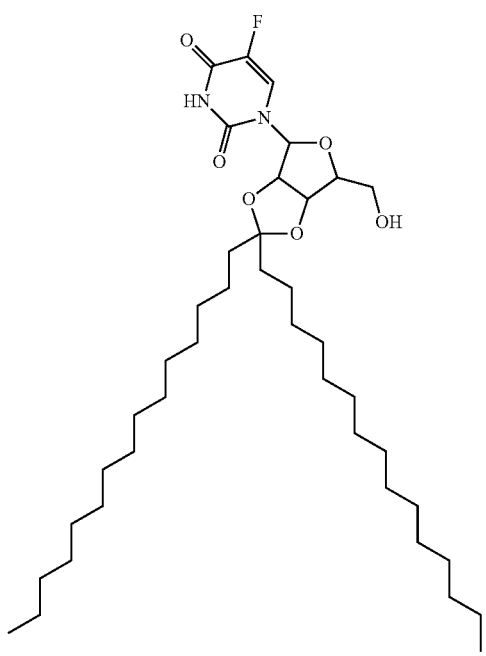

19d

To anhydr. 5-fluorouridine (1 g, 3.82 mmol) in THF (30 ml) was added to sylic acid (0.156 g; 0.9 mmol), hentriacontan-15-one (0.37 g, 8.22 mmol) and triethylorthoformate (0.7 ml, 4.01 mmol) in THF (ca. 30 ml). The reaction mixture was refluxed for 24 h. Then, the reaction was quenched by addition of Et$_3$N (0.22 ml, 1.59 mmol), and the mixture was poured into an ice-cold aq. 5% NaHCO$_3$ solution (20 ml) and stirred for 15 min. Then, the aqueous layer was washed with CH$_2$Cl$_2$; the organic layer was separated and dried (Na$_2$SO$_4$), filtered and evaporated. The residue was triturated with MeOH. The precipitate was filtered off and dried over night in high vacuo. Yield: 0.258 g (0.4 mmol, 49%). TLC (silica gel, CH$_2$Cl$_2$:MeOH; 95:5): R$_F$=0.6. $^1$H-NMR ((D$_6$)DMSO): 11.688 (s, NH); 8.107 (d, $^3$J(F, H—C(6)=7.0, H—C(6)); 5.848 (d, $^3$J(1',2')=1.3, H—C(1')); 5.015 (t, $^3$J(HO—C(5'), CH$_2$(5'))=5.0, HO—C(5')); 4.881 (dd, $^3$J(2',1')=2.5, $^3$J(2',3')=6.5, H—C(2')); 4.761 (dd, $^3$J(3',2')=6.5, $^3$J(3',4')==3.0, H—C(3')); 4.101 (ψdd, $^3$J(4',3')=3.5, $^3$J(4',5')=7.5, H—C(4')); 3.612 (m, J$_{AB}$=−12.0, CH$_2$(5')); 1.681 (m, 2H$_{endo}$—C(α')); 1.533 (m, 2H$_{exo}$—C(α)); 1.398 (m, $^2$H$_{endo}$—C(β')); 1.286 (m, 25×CH$_2$); 0.865 (m, 2×CH$_3$). $^{13}$C-NMR ((D$_6$)DMSO): 156.722 (d, $^2$J(F, C(4))=26.3, C(4)); 148.690 (C(2)); 139.662 (d, 'J(F, C(5))=230.0, C(5)); 125.504 (d, $^2$J(F, C(6))=35.8, C(6)); 116.471 (C(acetal)); 90.938 (C(1')); 86.507 (C(4')); 83.708 (C(3')); 80.296 (C(2')); 61.075 (C(5')); 36.307 (C(α')); 36.065 (C(a)); 30.897, 28.767, 28.711, 28.592, 28.567, 28.469, 28.442, 28.268, 23.164, 22.616, 21.654, (CH$_2$); 13.451 (2×CH$_3$).

xxiii) In-Situ Synthesis of 3-[(2S,4S,6S)-4-(5-fluoro-2,4-dioxo-3,4-dihydropyrimidin-1(2H)-yl)-6-(hydroxymethyl)-2-methyltetrahydrofuro[3,4-d][1,3]dioxol-2-yl]propanoic acid (37) and Coupling to Chitosane (1.1 kDa or 12.0 kDa) (→39)

The ester 28a (1.15 g, 2.97 mmol) was dissolved in EtOH/1 N aq. NaOH (35 ml, 1:1, v/v) and stirred at room temp. for 30 min. Then, the reaction mixture was neutralized by addition of Amberlite IR-120 (H$^+$-form). After filtration of the ion exchange resin and washing with EtOH/H$_2$O (1:1, 10 ml, twice) the combined filtrates were evaporated to dryness to yield the acid 37 as a slightly brownish solid (yield: 95%) which was coupled to the different chitosanes without further purification. {37: TLC (silica gel, CH$_2$Cl$_2$/MeOH, 9:1, v/v): R$_f$=0.3. $^1$H-NMR (D$_6$DMSO): 11.90 (s, 1H, NH); 7.90 (d, 1H, $^3$J(H—C(6), F)=7.0, H—C(6)); 5.82 (d, 1H, $^3$J(H—C(1'), H—C(2'))=1.2, H—C(1')); 5.20 (t, 1H, $^3$J(C(5')-OH, H—C(5'))=5.0, C(5')-OH); 4.84 (dd, 1H, $^3$J(H—C(2'), H—C(1'))=3.0, $^3$J(H-(2'), H—C(3'))=7.0, H—C(2')); 4.77 (dd, 1H, $^3$J(H—C(3'), H—C(2'))=6.5, $^3$J(H—C(3'), H—C(4'))=3.5, H—C(3')); 4.06 (ψg, 1H, $^3$J(H—C(4'), H—C(3'))=3.5, $^3$J(H—C(4'), H$_2$C-(5'))=4.0, H—C(4')); 3.63-3.55 (m, 2H, H$_2$C(5')); 2.13 (t, 2H, $^3$J=7.0, CH$_2$—C=O); 1.95 (t, 2H, $^3$J=7.0, CH$_2$); 1.23 (s, 3H, CH$_3$-acetal). HR ESI MS: m/z calculated for C$_{14}$H$_{16}$FN$_2$NaO$_8$ (MNa$^+$), 382.274. Found: 382.10}.

A) Coupling of the Acid 37 to Chitosane-1.1 kDa (→39). Chitosane [M$_w$, 1.1 kDa, 97.5% deacetylation, 50 mg, 0.045 mmol) was dissolved in diluted acetic acid (pH 5.0, 20 ml). To this soln. the acid 37 (155 mg, 0.405 mmol) was added. The suspension was stirred for 15 min at ambient temperature. Then, N-ethyl-N'-(3-dimethylaminopropyl)carbodiimide hydrochloride (EDC, 158 mg, 0.85 mmol), dissolved in a small amount of H$_2$O, was added. The reaction mixture was stirred over night at ambient temperature and then dialyzed against water (1 l, each; dialysis tube, MW-cut-off: 1.000 Da) for 3 days (3 changes). The content of the dialysis tube was then lyophilized to dryness to obtain the modified biopolymer 39. For determination of the ligand concentration, the product 39 (1 mg) was dissolved in water (1 ml), and the extinction was measured. The ligand concentration was calculated using the extinction coefficient of 28a (12.400 M$^{-1}$ cm$^{-1}$). The results are summarized in Table 3.

B) Coupling of the Acid 37 to Chitosane-12.0 kDa at Various pH-Values (→39).

Five chitosane samples [M$_w$, 12.0 kDa, 75% deacetylation, 100 mg, each) were dissolved in dilute aq. acetic acid solutions, the pH of which were adjusted to pH 3.5, 4.0, 4.5, 5.0, and 5.5, respectively. Subsequently, to each soln. the acid 37 (44.7 mg, 0.117 mmol, each) was added, and the mixtures were stirred for 30 min. at room temp. Then, EDC (67 mg, 0.35 mmol) was added to each solution, and stirring was continued over night. Next, all samples were dialysed against water (1 l, each; dialysis tube, MW-cut-off: 3.500 Da) for 3 days (3 changes). The content of each dialysis tube was then lyophilized to dryness to obtain the modified biopolymer 39. For determination of the ligand concentration (i) unmodified chitosane, (ii) compound 39 (1 mg, each) as well as (iii) compound 37 (785 µg) were completely hydrolyzed in 6N aq. hydrochloric acid (5 ml, each) for 1 h at 100° C. Each resulting soln. was diluted with water to a volume of 50 ml, each. UV absorbances of the diluted solutions were then measured at 268 nm, and the ligand concentration was calculated from the corresponding UV absorbances (see e.g. T. Wada et al., *J. Bioactive Compat. Polym.* 1994, 9, 429). The results are summarized in Table 3.

C) Sequential Coupling of the Acid 37 and of the Dye Atto-488 N(9)-butanoate to Chitosane-(1.1 kDa) to {Oligo [(8)$_x$-co-(7)$_y$-co-(9)$_z$-co-(10)$_w$]$_n$, 11}.

Chitosane [M$_w$, 1.1 kDa, 97.5% deacetylation, 50 mg, 0.045 mmol] was dissolved in diluted acetic acid (pH, 5.0, 20 ml). Thereupon, Atto-488-butanoate (1 mg) was dissolved in a small amount of water and added to the acid 37 (0.24 mg). The mixture was added to the chitosane soln. and stirred for 15 min at ambient temp. under exclusion of light. Next, EDC (0.72 mg) was dissolved in a small amount of $H_2O$ and added to the reaction mixture. After stirring for 1.5 h, the main portion of compound 37 (51.5 mg) was added, and stirring was continued for 15 min. Then, another portion of EDC (51.6 mg)—dissolved in a small amount of water—was added, and stirring was continued overnight. Dialysis against water (1 l, each; dialysis tube, MW-cut-off: 1.000 Da) for 3 days (3 changes), followed by lyophilisation gave the polymer 11. The ligand concentration was determined as described above; the results are summarized in Table 3.

2',3'-O-[1R)-4-Ethoxy-1-methyl-4-oxobutylidene]-5-fluoro-3-[(2E,6E)-3,7,11-trimethyldodeca-2,6,10-trien-1-yl] uridine (29a).

The ester 28a (500 mg, 1.29 mmol) was dissolved in anhydr. DMF (11.5 ml). Under $N_2$ atmosphere $K_2CO_3$ (0.685 g, 4.97 mmol) were added and the mixture was stirred for 10 min at room temp. Then, farnesyl bromide (0.39 ml, 1.42 mmol) was added drop-wise during 2 h. After stirring overnight the reaction mixture was filtered, and the residue was washed with a small amount of $CH_2Cl_2$. The combined filtrates were evaporated to dryness in high vacuo over night. The oily residue was chromatographed on silica gel (column: 5×7.5 cm). Elution with $CH_2Cl_2$ (125 ml) followed by $CH_2Cl_2$/MeOH (95:5, v/v, 500 ml) afforded a main zone which was evaporated to give compd. 29a as a colourless oil. TLC (silica gel, $CH_2Cl_2$/MeOH 95:5, v/v): $R_f$ 0.73. $^1$H-NMR ($D_6$-DMSO): 8.204 (d, $^3$J(H—C(6), F)=7.0, H—C (6)); 5.881 (d, $^3$J(1',2')=2.0, H—C(1')); 5.197 (t, $^3$J(HO—C (5'), H—C(5')=5.0, HO—C(5')); 5.126 (t, $^3$J(2",1")=7.5, H—C(2")); 5.043 (m, $H_2$—C(1")); 4.911 (dd, $^3$J(2',1')=3.5, $^3$J(2',3')=6.5, H—C(2')); 4.797 (dd, $^3$J(3',2')=6.5, $^3$J(3',4')=3.0, H—C(3')); 4.404-4.391 (m, 2H, H—C(6"), H—C(10")); 4.149 (m, H—C(4')); 4.057 (q, $^3$J=7.0, $CH_2$ (ester)); 3.650-3.583 (m, $CH_2$(5')); 2.416 (t, $^3$J=7.0, $CH_2$—C=O); 2.051-1.887 (5 m, 10H, $H_2$—C(4"), $H_2$—C(5"), $H_2$—C(8"), $H_2$—C(9"), $CH_2$(ester)); 1.738 (s, $H_3$—C(13")); 1.629 (s, $H_3$—C(14")); 1.548 (s, $H_3$—C(15")); 1.533 (s, $H_3$—C(12")); 1.269 (s, $CH_3$(acetal)); 1.190 (t, $^3$J=7.0, $CH_3$ (ester). $^{13}$C-NMR ($D_6$DMSO): 172.432 (C=O); 156.102 (d, $^2$J(C(4), F)=26.2, C(4)); 148.710 (C(2)); 139.354 (d, $^1$J(C (5), F)=228.9, C(5)); 139.382 (C(3")); 134.536 (C(7")); 130.550 (C(11")); 124.373 (d, $^2$J(C(6), F)=34.7, C(6)); 124.006 (C(6")); 123.486 (C(10")); 118.122 (C(2")); 113.623 (C(acetal)); 91.785 (C(1')); 86.564 (C(4')); 83.988 (C(2')); 80.224 (C(4')); 61.073 (C(5')); 59.823 ($CH_2$(ester)); ~38.0 (3 signals, superimposed by solvent signals, C(1"), C(4"), C(8")); 33.342 ($CH_2$—C=O); 28.103 ($CH_2$(acetal)); 26.108 (C(5")); 25.617 (C(9")); 25.369 (C(12")); 23.479 ($CH_3$(acetal)); 17.420 (C(15")); 16.089 (C(14")); 15.700 (C(13"); 13.968 ($CH_3$(ester)). HR ESI MS: m/z calculated for $C_{31}H_{46}FN_2O_8$ (MH$^+$), 593.696. found, 593.40; 335.2 [N(3)-farnesyl-5-fluorouracil].

In-Situ Synthesis of the Acid 38 and Coupling to Chitosane (1.1 kDa) (40). The N(3)-farnesylated acid 38 was prepared from its precursor ester 29a as described for the acid 37 starting from 29a (489 mg, 0.825 mmol) and using a mixture of EtOH (10 ml) and 1N aq. NaOH (5 ml). After 30 min of stirring at ambient temp. the mixture was neutralized by addition of Amberlite IR 120, H+ form), filtered, washed with EtOH/$H_2O$, 1:1) and evaporated to dryness giving the acid 38 in quantitative yield as its sodium salt.

Next, chitosane (1.1 kDa, 50 mg, 0.045 mmol) was dissolved in either aq. acetic acid (pH 5.0, 20 ml) (I; yielding a low ligand concentration) or in a mixture of aq. acetic acid (pH 5.0)/1,4-dioxane (20 ml, 1:1, (v/v)) (ii; yielding a high ligand concentration). After addition of the acid 38 (237.6 mg, 0.405 mmol), the mixture was stirred for 15 at ambient temperature. Then EDC (158 mg)-dissolved in a small volume of $H_2O$—was added, and stirring was continued overnight. The resultant was dialysed against water (1 l, each; dialysis tube, MW-cut-off: 1.000 Da) for 3 days (3 changes), followed by lyophilisation giving the polymer 40. Its ligand concentration was determined as described above; the results are summarized in Table 3.

Preparation of Chitosan Foils.

For the successful preparations of chitosan foils freeze-dried chitosanes were suspended in the corresponding solvent mixture (Table 1), slowly stirred for 30 min at room temperature and subsequently de-gassed by ultrasonication for 30 s. Occasionally occurring small air bubbles were removed with the help of a pin. Then, the clear solutions were poured into Petri dishes and stored overnight at ambient temperature. After 16 h the Petri dishes were heated for 1 h in a vacuum drying oven at 30-40° C. Then, the foils were covered with a 1N aq. NaOH solution and stored for 10 min. After removal of the alkaline solution the foils were intensively washed with $H_2O$. They can be stored in $H_2O$ for several days until use.

TABLE 1

Reaction conditions for the preparation of chitosan foils.

| Entry | $M_n$ [kDa]/ amount [mg] | $H_2O$ [ml] | HAc [ml] | HCOOH [ml] | MeOH [ml] | v/v/v relation of solvents | PEG 200 [ml] | PEG 6.000 [g] | Properties of foil |
|---|---|---|---|---|---|---|---|---|---|
| E | 14.0/100 | 8 | 1 | — | 1 | 8:1:1 | — | — | ductile, tear-proof |
| J | 82.0/500 | 40 | 5 | — | 5 | 8:1:1 | — | — | smooth surface |
| K | 82.0/500 | 40 | 5 | — | 5 | 8:1:1 | 5 | — | ductile, tear-proof |
| P[1)] | 20-200/400 | 24 | — | 8 | 8 | 6:2:2 | — | — | ductile, tear-proof |
| Q[2)] | 20-200/400 | 24 | — | 8 | 8 | 6:2:2 | — | — | ductile, tear-proof |
| T | 20-200/400 | 24 | — | 8 | 8 | 6:2:2 | — | 0.3 | turbid, tear-proof |

[1)]The mixture was poured into a single Petri dish, resulting in a foil of ≈1 mm thickness.
[2)]The mixture was equally partitioned between two Petri dishes giving foils of ≈0.5 mm thickness.

Coupling of the Acid 37 to Chitosan Foils and Determination of Ligand Concentrations.

For the covalent immobilization of the acid 37 to chitosan foils (Table 2) compound 37 (158 mg, 0.4 mmol or 79 mg, 0.2 mmol) was dissolved in $H_2O$ (10 ml) which had been slightly acidified (pH 4 or 5, see Table 4) with AcOH. Thereupon, the corresponding chitosan foil (10×10×1 mm) was put into the solution, and p-dioxane (10 ml) was added. The mixture was stirred for 1 h at room temperature. Then, N-ethyl-N'-(3-dimethylaminopropyl)-carbodiimide hydrochloride (EDC, 158 mg, 0.85 mmol) was added, and stirring was continued overnight. The foil was washed with $H_2O$, transferred into a dialysis tube (cut-off mass, 3.000 Da), filled with $H_2O$, and dialyzed against $H_2O$ (1 l, 3 days, 3 changes). The foils were dried at 25° C. in a vacuum drying oven overnight.

TABLE 2

Reaction conditions of the coupling of compound 37 to chitosan foils.

| foil | amount of 37 [mmol] | pH | time [days] | ligand concentration [mg of ligand/g of foil] |
|---|---|---|---|---|
| P | 0.4 | 5.0 | 1 | 44.5 |
| Q | 0.4 | 4.0 | 2 | 94.8 |
| Q | 0.2 | 4.0 | 4 | 69.6 |
| Q | 0.2 | 5.0 | 4 | 96.3 |

For the determination of the ligand concentration of the dried conjugates the corresponding chitosan foils (Table 2, 1 mg, each) as well as 1 mg of the un-coupled chitosan foil and acid 37 (785 µg) were suspended in 6N aq. hydrochloric acid (20 ml, each). Aliquots of 5 ml, each, were heated at 100° C. for 1.5 h, upon which the foils went completely into solution. After cooling to room temperature each solution was diluted with $H_2O$ (5 ml), and their UV absorbance at 268 nm was measured. The resulting ligand concentrations are given in Table 2.

Diffusion of Rhodamin B Through Chitosan Foils

Figure 9A:
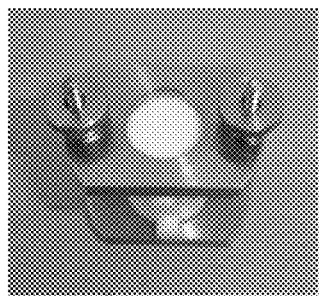
FIG. 9a is one view of a Franz diffusion cell having two Teflon chambers of 1.5 mL volume each.

Further, the diffusion of the water-soluble dye Rhodamin B through the chitosan foils from the experiments J, K, Q, and T was measured using a simple Franz diffusion cell (FIG. 9).

Figure 10:
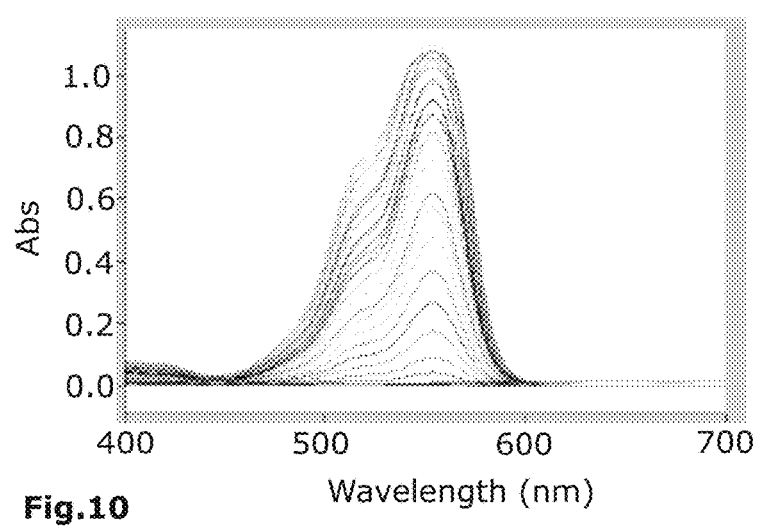
FIG. 10 illustrates the aerial overlay of Vis spectra of the accept cell content after passing the chitosan foil from experiment J (Table 2)

The diffusion device consists of two compartments of 1.5 ml volume, each, between which the corresponding chitosan foil (from experiments 3, K, Q, and T) was fixed. The left compartment (donor cell) was filled with the aqueous Rhodamin B solution, the other one (acceptor cell) with pure $H_2O$. Every 4 minutes the content of the acceptor chamber was removed with a Hamilton syringe, and its V is spectrum was recorded, the results of which are shown in FIG. 10.

Acidic Cleavage of the O-2,3'-Ketal Connector of 28a and Degradation of Chitosan-Bound 5-Fluorouridine by Chitosanase from Streptomyces sp. 174.

Both, the acidic hydrolysis of the O-2',3'-ketal moiety of the ester 28a as well as the chitosanase-catalyzed degradation of chitosan foil-bound 5-fluorouridine was measured. Acidic stability was determined by incubating compound 28a (2 mg) in 1N aqueous HCl/MeCN 1:1 (v/v), neutralization by $Et_3N$ and subsequent RP-18 HPLC analysis as described above (FIG. 12).

Degradation of Chitosan-Foil-Bound 5-Fluorouridine by Chitosanase from Streptomyces sp. 174

The degradation of chitosan-foil-bound 5-fluorouridine by chitosanase from Streptomyces sp. 174 was studied using the above described Franz diffusion cell. For this purpose, first, a piece (4×4×1 mm) of the foil from experiment P (Table 2) was placed into the donor chamber of the Franz cell in $H_2O$. The two compartments were separated by a swollen dialysis membrane (cut-off mass: 1.000 Da). After filling the acceptor chamber with $H_2O$, chitosanase (5 µl of an enzyme suspension, 30 U/mg of protein) was added to the donor chamber containing the blank foil. The whole cell was placed at 37° C. in an oven. Inspection of the cell content after 2 days showed that the foil was completely solubilized.

Figure 14:
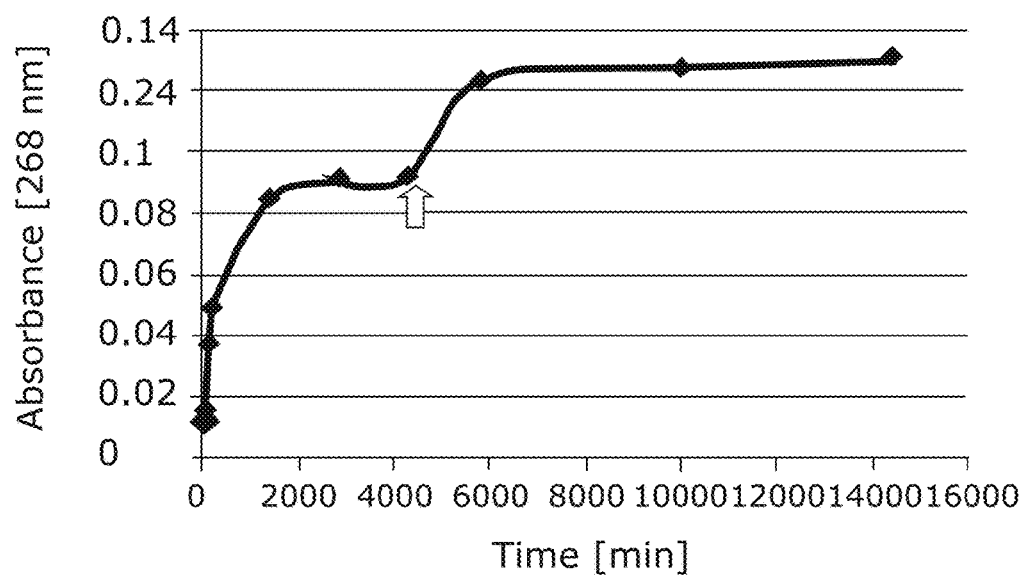
FIG. 14 illustrates the chitosanase-catalyzed degradation of a 5-FU-chitosan foil-conjugate.

The enzyme-catalyzed degradation (5 µl of a chitosanase suspension, 30 U/mg of protein) of a 5-FU-loaded foil (Table 2, 4$^{th}$ entry, 4×4×1 mm piece) was investigated. For this purpose the UV absorbance at 268 nm of the aqueous solution of the acceptor chamber was measured at intervals within a period of 10 days and plotted vs. time (FIG. 14).

Sequential Coupling of the Acid 38 and the Dye Atto-488 N(9)-butanoate to Chitosane-(1.1 kDa) to {Oligo[(8)$_x$-co-(7)$_y$-co-(9)$_z$-co-(10)$_w$]$_n$, 12}.

Chitosane [$M_w$, 1.1 kDa, 97.5% deacetylation, 50 mg, 0.045 mmol) was dissolved in diluted acetic acid (pH, 5.0)/1,4-dioxane (1:1, (v/v), 20 ml). Thereupon, Atto-488-butanoate (1 mg) was dissolved in a small amount of water and added to the acid 38 (0.365 mg), dissolved in a small volume of $H_2O$/1,4-dioxane (1:1). Both solutions were then combined and stirred for 15 min at ambient temperature under exclusion of light. Next, EDC (0.770 mg), dissolved in a small amount of $H_2O$, was added, and stirring was continued for 1 h. Subsequently, the main portion of the acid 38 (157.9 mg) was added and—after further 15 min—a second portion of EDC (51.6 mg, dissolved in a small volume of $H_2O$). Then, the mixture was stirred overnight at ambient temperature. Dialysis was performed (MW-cut-off: 1.000 Da) for 3 days (3 changes) under exclusion of light. Lyophilization gave the polymer 12; its ligand concentration was determined as described above, and the results are summarized in Table 3.

TABLE 3

Reaction conditions and ligand concentration of chitosan-bound 5-fluorouridine derivatives.

| Chitosan | pH (aq. HAc) | Ligand(s) (5-FU-Derivative), Atto dye) | Ligand concentration [mg of 5-FU-derivative/g modified Chitosan] |
|---|---|---|---|
| 1.1 kDa | 5.0 | (28a) | 443.5 |
| 1.1 kDa | 5.0 | (28a), (Atto-488) | 212.1 |
| 1.1 kDa | 5.0 | (29a) | 383.0; 1412.4$^{a)}$ |
| 1.1 kDa | 5.0 | (28a), (Atto-488) | 606.7$^{a)}$ |
| 12 kDa | 5.5 | (28a) | 0 |
| 12 kDa | 5.0 | (28a) | 86.8 |
| 12 kDa | 4.5 | (28a) | 85.7 |
| 12 kDa | 4.0 | (28a) | 141.6 |
| 12 kDa | 3.5 | (28a) | 7.3 |

$^{a)}$Coupling reactions were performed in a mixture of aq. HAc/1,4-dioxane (1.1, v/v).

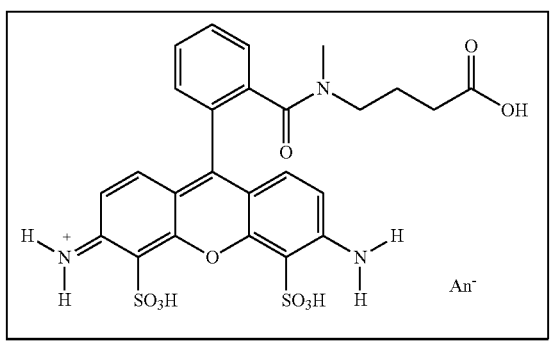
(Atto-488)

Measurements on the Derivatives

1) Incorporation of the Eterneon-Labeled Compound (36) into an Artificial Bilayer Measurements of the incorporation of the prepared derivatives has been carried out on with the apparatus "Ionovation Explorer" of Ionovation GmbH, Germany which is equipped with a standard inverted fluorescence microscope and a computer controlled perfusion unit as well as a disposable, optical transparent microfluidic sample carrier with perfusion capabilities. A "Bilayer Port" gives direct access to the lipid bilayer, while both sides of the bilayer can be perfused via the cis and trans channel. Calibration wells allow optical control experiments when needed. A detailed setup of the apparatus is described in E. Werz, et. al. Chemistry & Biodiversity, Vol. 9, 2012, 272-281. The measurements on compound 36 are reflected in the following figures:

FIG. 1-1: Z-Scan of an empty bilayer

Figures 1, 2:
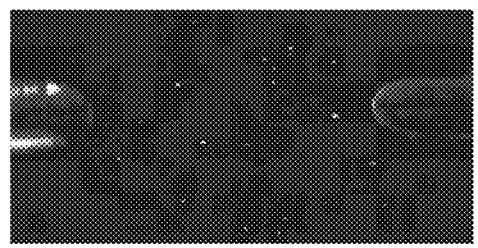

FIG. 1-2: Z-Scan after injection of a dilute soln. of 36 in MeCN (1 μl) into the cis compartment of the slide and torn of the bilayer.

Figures 1, 2, 3:
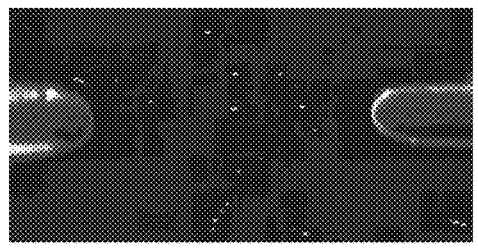

FIG. 1-3: Z-Scan after 5 min of incubation. Slowly massing of aggregates at the Teflon annulus.

FIG. 1-4: Z-Scan after further 5 min of incubation. Most of the aggregates are covering the teflon annulus.

FIG. 1-5: Repeat of the experiment as reflected in FIG. 1-1. Z-Scan of the empty bilayer.

FIG. 1-6: Z-Scan after injection of a MeCN soln. of 36 (1 μl) to the cis compartment of the slide and 5 min of incubation.

FIG. 1-2 shows that upon injection of a dilute MeCN solution of compound 36 into the cis compartment of the bilayer slide the bilayer is torn at once. As a result, compound 36 forms high molecular-weight aggregates (micelles) which slowly mass at the teflon-coated aperture annulus (FIGS. 1-2, 1-3 and 1-4). Photon correlation spectroscopy (PCS) measurements with a scattering angle of 90° gives a size distribution (Poisson distribution) of the resulting particles with mean values between ca. 600 and 1200 nm. In a second experiment a concentrated solution of 36 in MeCN was injected into the cis compartment of the bilayer slide. In this case it was observed that during an incubation time of 5 min the dye-labelled nucleolipid is immobilized within the bilayer (FIGS. 1-5 and 1-6).

FIG. 2 shows the relative brightness intensities of the bilayer before and after addition of compound 36.

2. Lipophilicity of Various Derivatives as Shown in Table 4

The lipophilicity of various 5-fluorouridine derivatives has been studied since the lipophilicity has inter alia an influence on the incorporation into oligo(2'-deoxynucleotides). The lipophilicity of the novel hydrophobic nucleoside derivatives has been studied in different by two ways: (i) log P values of the compounds were calculated (Table 4) and compared with those of the unmodified nucleoside 1a, (ii) the chromatographic mobilities of the compounds were measured in terms of retention times ($t_R$ in min) by RP-18 HPLC.

Table 4 shows the calculated log P as well as the corresponding $t_R$ values of the various compounds. It can be seen that the calculated log P values bestride more than ten orders of magnitude.

TABLE 4

Calculated log P and RP-18 HPLC Retention Times of Hydrophobic 5-Fluorouridine Derivatives.

| Compd. | Calc, log P | RP-18 HPLC $t_R$ [min] |
| --- | --- | --- |
| 1a, 5-fluorouridine | −1.34 ± 0.46 | 1 |
| 19a | +0.50 ± 0.56 | unstable |
| 23 | +6.26 ± 0.62 | 27 |
| 24 | +7.56 ± 0.67 | 24 |
| 19c | +9.00 ± 0.56 | >600 |
| 25 | +9.68 ± 0.67 | 87 |

3. Lipophilic Oligonucleotides and their Bilayer Insertion.

The phosphor-amidites 26 and 27-together with a cyanine-3 phosphoramidite-were used to prepare two oligonucleotides with the following sequences:

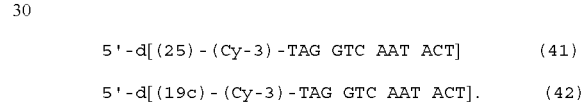

The oligomers were characterized by MALDI-TOF mass spectrometry. The ms analysis revealed that during recording the spectrum the oligomer 41—prepared with a pending N(3)-farnesylated 5-fluorouridine residue (25)—underwent an acid-induced deprenylation of the sesquiterpene side chain by one isoprene moiety yielding an oligomer which carries a terminal N(3)-geranylated 5-fluorouridine nucleotide derivative. This was surprising as we have successfully synthesized simultaneously corresponding oligomers which carry nucleotide residues with either pending N(3)-farnesylated thymidine or N(1)-farnesylates inosine; in those cases no cleavage of the sesquiterpene moiety was observed during MALDI TOF analysis which points an electronic long-range influence of the fluorine substituent on the farnesyl side chain.

Bilayer Insertion.

The insertion of the oligonucleotides 41 and 42 was tested at artificial bilayer membranes composed of POPE/POPC (8:2, w/w) in n-decane (100 mg/ml) in a set-up as described in E. Werz, et. al. Chemistry & Biodiversity, Vol. 9, 2012, 272-281.

The setup is a horizontal bilayer chamber wherein the chamber contains two compartments (Cis and Trans) which are separated by a thin PTFE film. The film is perforated by a 100 μm hole which is the only connection between the trans and cis compartment. When a lipid solution is painted over the hole a bilayer forms spontaneously. The distance from the bilayer to the coverslide is 100 μm. Thus, the membrane is accessible by a high numerical aperture water objective. Electrodes in cis and trans allow electrophysiological recordings of the bilayer. The cis and trans compartments have a buffer volume of 100 μl. The membrane spans the aperture in the PTFE film. The interface of the film and the bilayer is bridged by the torus which contains the bulk solvent and lipids.

Figures 1, 2, 3, 4:
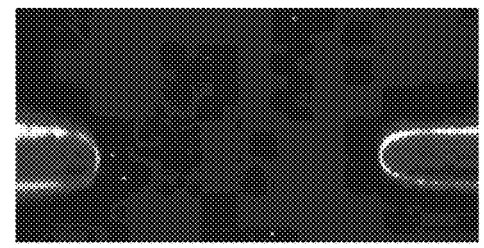

The following Figures show the measurement results wherein FIG. 3 reflects the measurements concerning the bilayer insertion of 5'-d[25]-(Cy-3)-TAG GTC AAT ACT] (41) and FIG. 4 reflects the bilayer insertion of 5'-d[(19c)-(Cy-3)-TAG GTC AAT ACT] (42).

Figures 1, 2, 3, 4, 5:
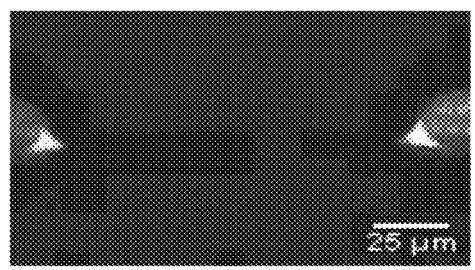

FIG. 3-1: Side view on empty bilayer
FIG. 3-2: Sloped view on empty bilayer
FIG. 3-3: Side view on bilayer after addition of 41
FIG. 3-4: Sloped view on bilayer after addition of 41
FIG. 3-5: Side view on filled bilayer after 1. Perfusion
FIG. 3-6: Sloped view on filled bilayer after 1. Perfusion
FIG. 3-7: Side view on filled bilayer after 2. Perfusion
FIG. 3-8: Sloped view on filled bilayer after 2. Perfusion
FIG. 4-1: Side view on empty bilayer
FIG. 4-2: Sloped view on empty bilayer
FIG. 4-3: Side view on bilayer after addition of 42
FIG. 4-4: Sloped view on bilayer after addition of 42
FIG. 4-5: Side view on filled bilayer after 1. Perfusion
FIG. 4-6: Sloped view on filled bilayer after 1. Perfusion
FIG. 4-7: Side view on filled bilayer after 2. Perfusion
FIG. 4-8: Sloped view on filled bilayer after 2. Perfusion From FIGS. 3-1 to 3-8 and 4-1 to 4-8 it can be seen that both lipophilized oligonucleotides are successfully incorporated into the artifical bilayer. Comparison of the brightness of the layers, however, clearly show that the oligomer 42 carrying a double-tailed nucleolipid moiety is better inserted. In this case even several perfusions of 60 s, each, do not lead to a significant removal of the conjugate from the bilayer while in case of the oligomer 41 the brightness of the layer decreases after two perfusions Determination of the Diffusion Times of Oligonucleotides FIG. 5 shows a schematic breadboard construction for the determination of the diffusion times of oligonucleotides.

The diffusion times (µs) of 41 and 42 were measured, both without and in the presence of an artificial bilayer. For the determination of the free diffusion times the corresponding oligomer solution (50 nM) was diluted so that in the confocal measuring volume (~$10^{-15}$ l) only one fluorescent molecule was present. Each measurement was performed ten-fold for 30 s, each. In order to determine the diffusion times of the lipophilized oligonucleotides (41, 42) in the presence of a bilayer five measuring positions above, beneath and in the bilayer were chosen. This was necessary because the bilayer is floating within certain limits, which makes it difficult to target it most exactly (FIG. 5, measuring points 1-5). Each measurement was performed (i) by recording reference data of a stable, blank bilayer, (ii) addition of the oligonucleotide sample and a subsequent 25-min incubation, followed by recording of the data, (iii) recording of further data series after perfusion of the chambers. Table 5 summarizes the results.

TABLE 5

Diffusion times (µs) of 41 and 42 without and in the presence of a lipid bilayer.

| Sample | Free diffusion time [µs] |
|---|---|
| buffer | 45.70 ± 10.25 |
| 41 | 279.67 ± 141.08 |
| 42 | 390.39 ± 249.05 |

TABLE 5-continued

Diffusion times (µs) of 41 and 42 without and in the presence of a lipid bilayer.

| | Diffusion times in the presence of a bilayer [µs] at measuring point 3 (FIG. 6) |
|---|---|
| Empty bilayer | 829.88 ± 124.90 |
| 41 | 33547 ± 16751, after 1. perfusion |
| 42 | 12866 ± 1364, after 2. perfusion |
| 42 | 75952 ± 8201, after 1 perfusion |
| 42 | 53868 ± 11623, after 2. perfusion |
| 42 | 19891 ± 3266, after 3. perfusion |

It can be seen that the free diffusion time of the oligomer with a double-chained 5-fluorouridine derivative (42) exhibits a significantly longer free diffusion time than the oligomer 41 which points to the formation of a high-molecular-weight aggregate of the nucleolipid. Also near a lipid bilayer the oligonucleotide with a 19c-residue at the 5'-terminus is incorporated more strongly into the bilayer and exhibits, therefore, a significantly higher diffusion time compared to 41.

Oncological Tests

Cell Lines and Culture Conditions

In vitro experiments were performed using HT-29 (human colon carcinoma) cell line (DSMZ, GmbH, Braunschweig, Germany). The cells were cultured in 90% RPMI 1640 supplemented with 10% fetal bovine serum (FBS), 100 U/ml penicillin, 0.1 mg/ml streptomycin. Cells were maintained at 37° C. in a humidified atmosphere of 5% $CO_2$ and 95% air; the medium was changed every 48 h.

Substances Under Test

The following 5-Fluorouridin-derivatives have been tested:

28a denoted as 5-FU-A (comparative)

30a denoted as 5-FU-B (comparative)

19c denoted as 5-FU-C(according to the invention)

29a denoted as 5-FU-D (according to the invention) and 31a denoted as 5-FU-E (according to the invention)

5-FU-A:

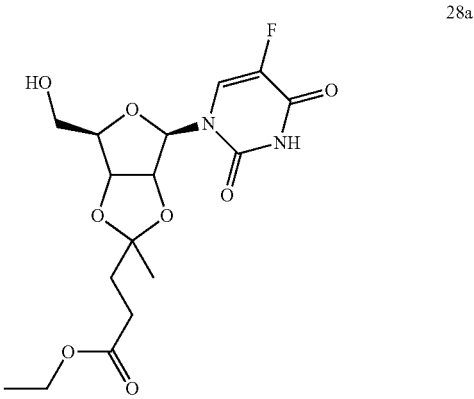 [SMILES: CCOC(=O)CCC1(C)OC2C(O1)[C@@H](CO)O[C@H]2n1cc(F)c(=O)[nH]c1=O]

28a

5-FU-B

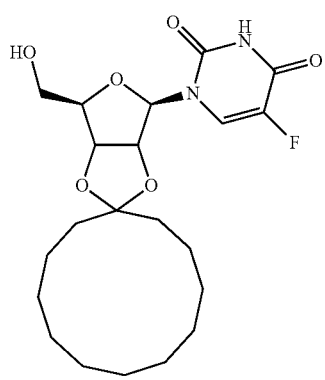

5-FU-C:

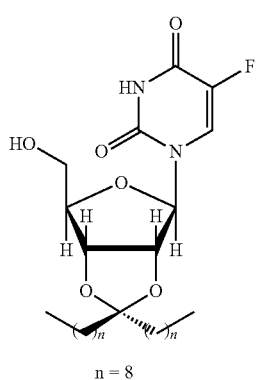

n = 8

5-FU-D

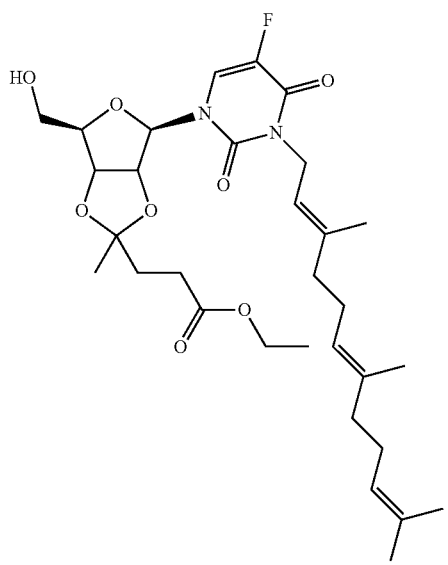

5-FU-E

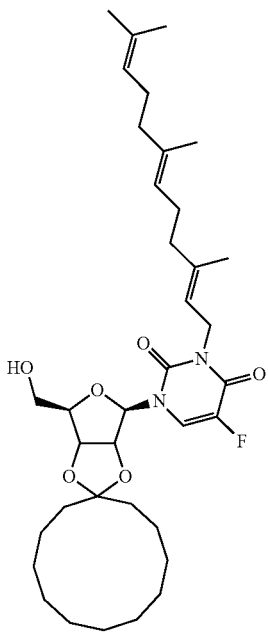

(19c)

Determination of Viability/Survival of 5-FU and Derivates $1 \times 10^4$ human HT-29 in 100 μl medium/well were seeded in 96-well plates (BD Falcon™, Becton Dickinson GmbH, Heidelberg, Germany). After 24 h, the medium was changed and different concentrations of 5-fluorouracil, 5-fluorouridin and 5-fluorouridin derivative molecules (10, 20, 40 or 80 μM) were tested. After 24, 48 or 72 h incubation, viability/survival was measured using PrestoBlue™ reagent (Invitrogen-Life Technologies GmbH, Darmstadt, Germany). PrestoBlue™ reagent is more sensible than alamarBlue®, which is a redox indicator of enzyme activity widely used in whole organism screening for viability/cytotoxicity (1-6). PrestoBlue™ was directly added to the cells into the culture medium at a final concentration of 10%. Thereafter the plates were returned to the incubator. 30 min, 1 h, 2 h, 3 h and 4 h after addition of PrestoBlue™ the optical density (OD) was measured at 570 nm and 600 nm (as reference) with a SUNRISE ELISA-reader (Tecan, Salzburg, Austria). Results are expressed in % of survival [OD 570/600 nm of samples x 100/OD 570/600 nm of control without substances)]. As control (=100% viability) cells were cultured with medium alone (i.e. without addition of test substances). The Sigma Plot software was used to carry out statistical analyses by the unpaired Student's t test. Data are shown as mean±SEM. A p value<0.05 was considered as statistically significant.

Figures 1, 2, 3, 4, 5, 6:
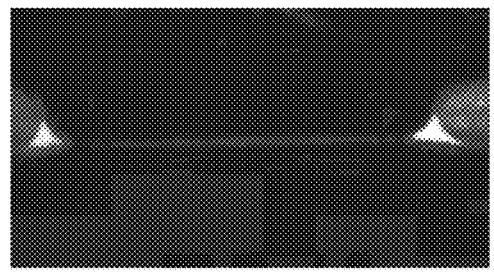
Figure 2:
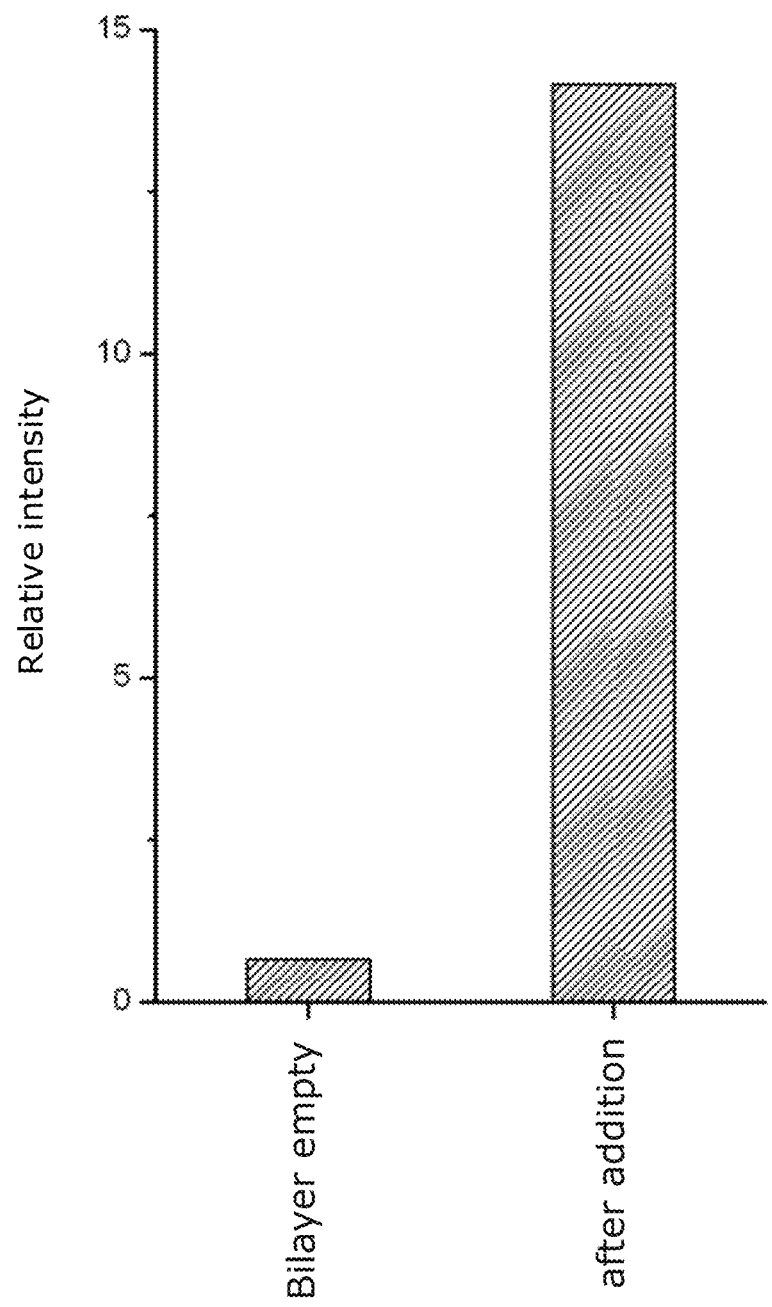
Figures 1, 3:
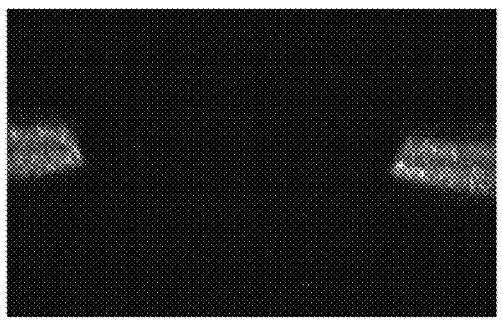
Figures 2, 3:
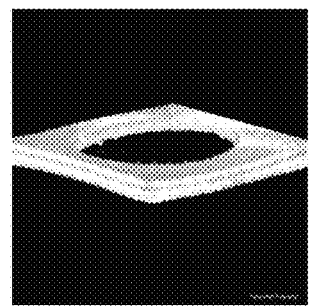
Figure 3:
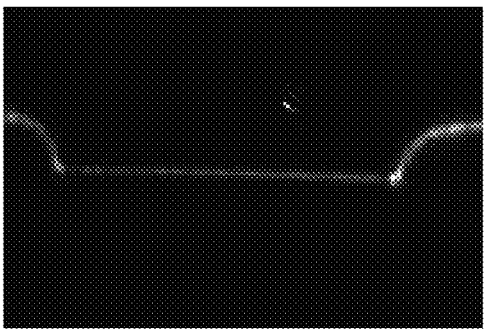
Figures 3, 4:
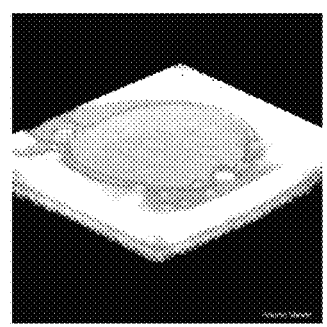
Figures 3, 4, 5:
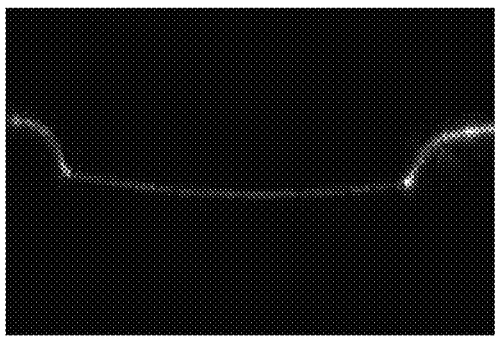
Figures 3, 4, 5, 6:
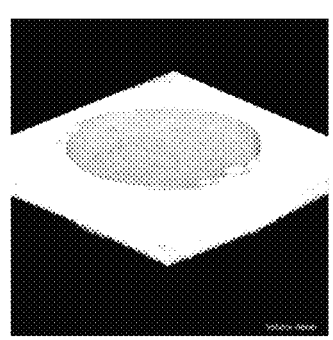
Figures 3, 4, 5, 6, 7:
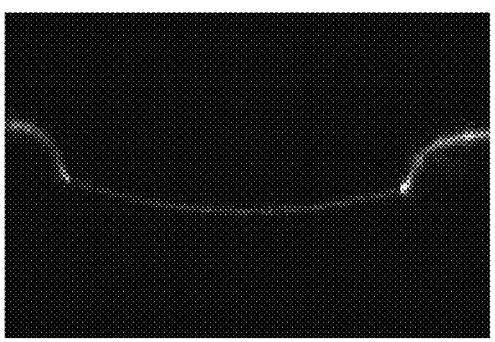
Figures 3, 4, 5, 6, 7, 8:
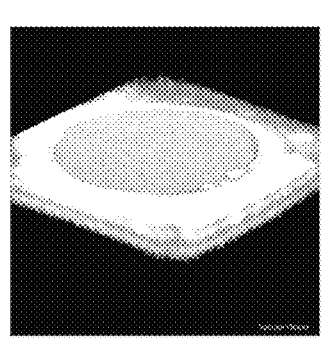
Figures 1, 4:
Figures 2, 4:
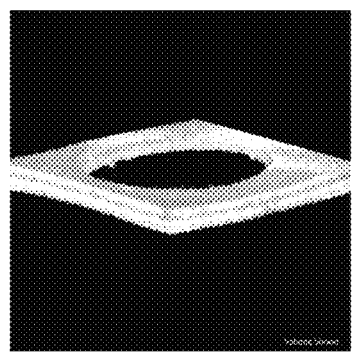
Figures 3, 4:
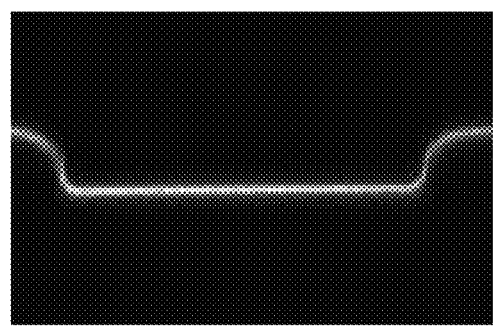
Figure 4:
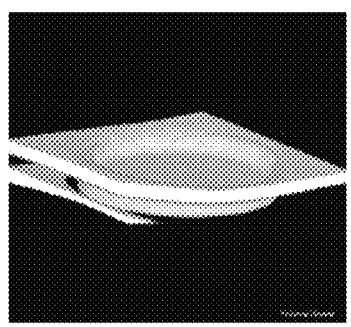
Figures 4, 5:
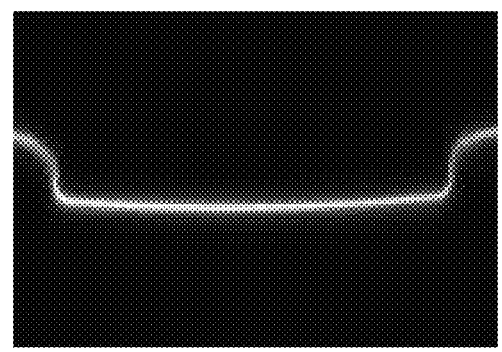
Figures 4, 5, 6:
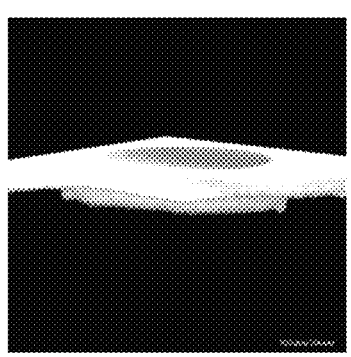
Figures 4, 5, 6, 7:
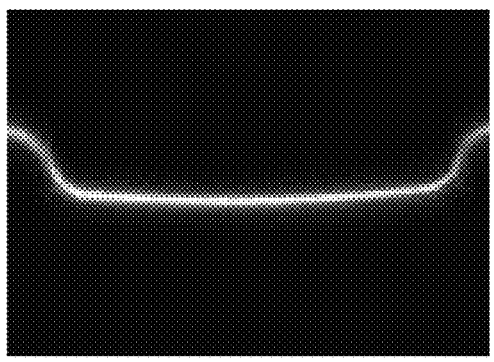
Figures 4, 5, 6, 7, 8:
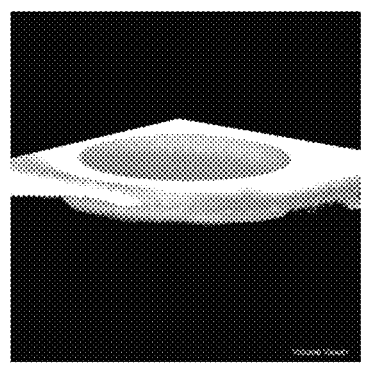
Figure 5:
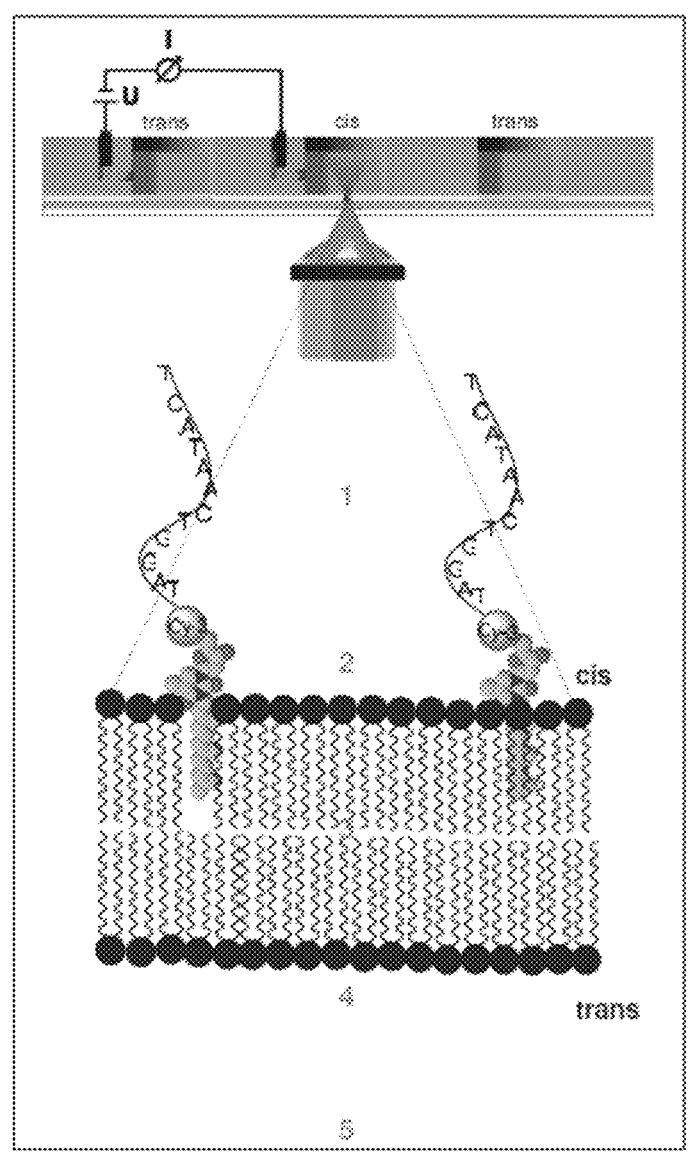
Figure 6:
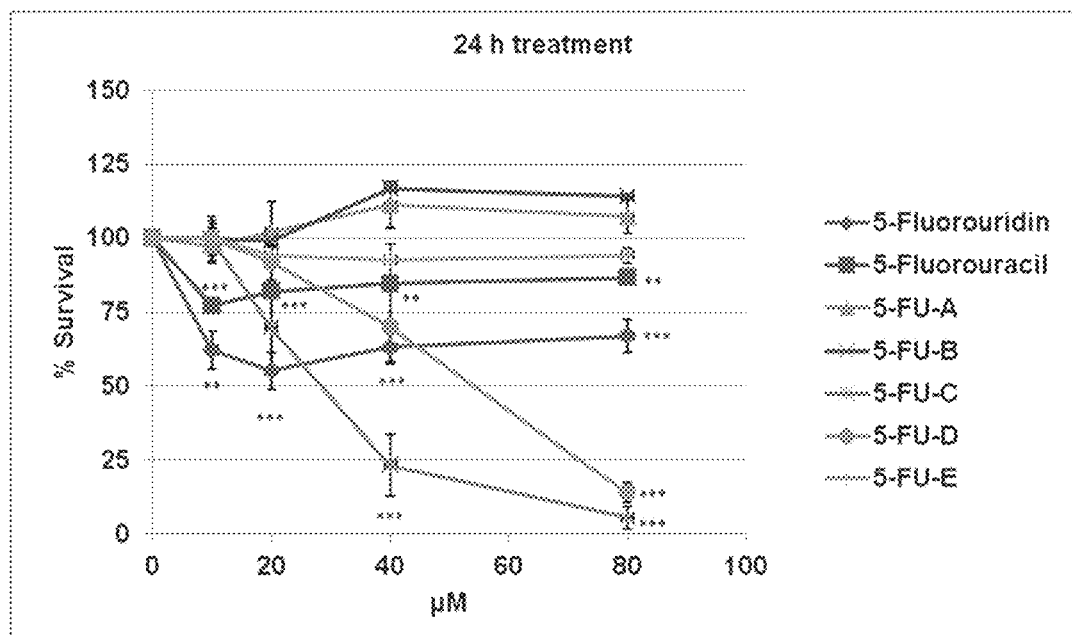
Figure 7:
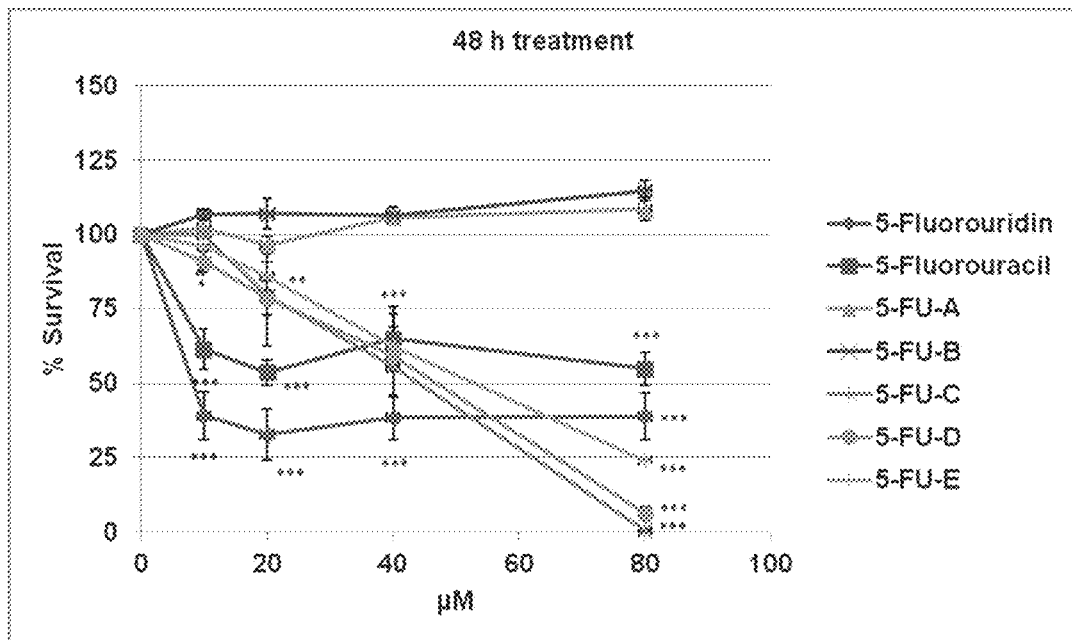
Figure 8:
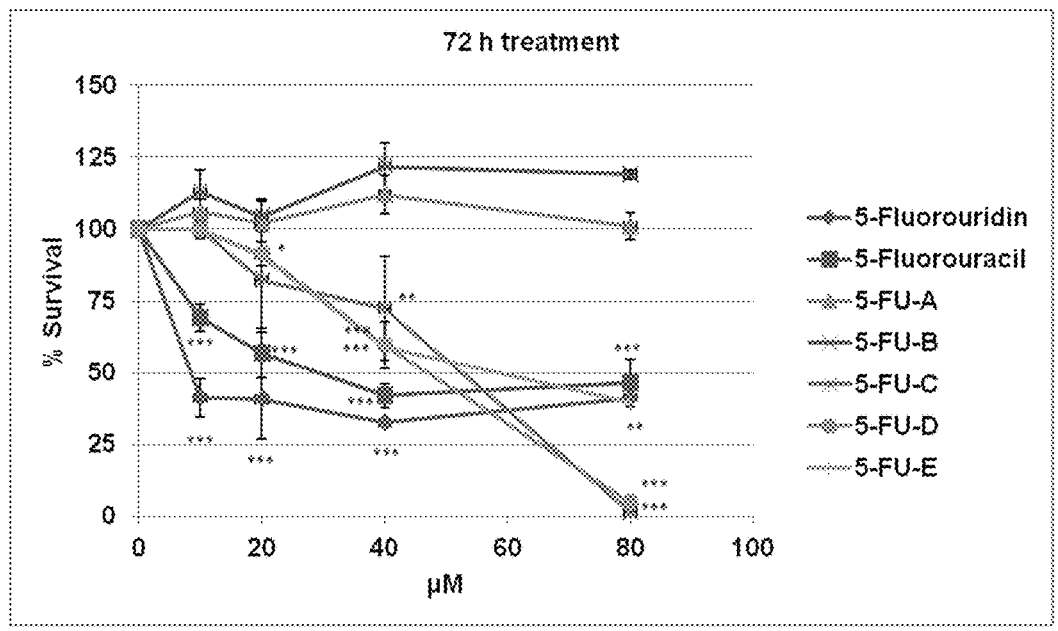

Oncological Tests Results are Reflected in FIGS. 6 to 8

FIG. 6: Viability/survival of human colon carcinoma cell line HT-29 after 24 h incubation with 5-fluorouridin (5-FU), its derivatives 5-FU-A, -B. -C, -D or -E or 5-fluorouracil as control. Values are given in % survival of control (without treatment/medium alone; =100% survival), as mean±SEM; p, significance vs. control without treatment, *p<0.05, p<0.01, *p<0.001. N=4 independent experiments, using 4-6 wells per treatment and experiment.

FIG. 7: Viability/survival of human colon carcinoma cell line HT-29 after 48 h incubation with 5-fluorouridin (5-FU), its derivatives 5-FU-A, -B. -C, -D or -E or 5-fluorouracil as control. Values are given in % survival of control (without treatment/medium alone; =100% survival), as mean±SEM;

p, significance vs. control without treatment, *p<0.05, p<0.01, *p<0.001. N=4 independent experiments, using 4-6 wells per treatment and experiment.

FIG. 8: Viability/survival of human colon carcinoma cell line HT-29 after 72 h incubation with 5-fluorouridin (5-FU), its derivatives 5-FU-A, -B. -C, -D or -E or 5-fluorouracil as control. Values are given in % survival of control (without treatment/medium alone; =100% survival), as mean±SEM; p, significance vs. control without treatment, *p<0.05, p<0.01, *p<0.001. N=4 independent experiments, using 4-6 wells per treatment and experiment.

As can be seen from the oncological test results the compounds of the invention 29a and 31a demonstrate a significant higher activity against carcinoma cells than the comparative compounds and the 5-fluorouridine and 5-fluorouracil.

Figure 9B:
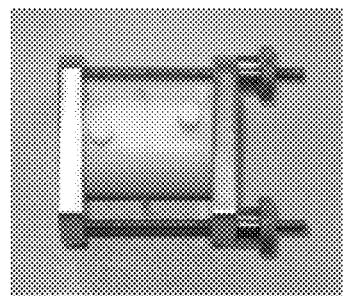
FIG. 9b is another view of a Franz diffusion cell having two Teflon chambers of 1.5 mL volume each.

FIG. 9 and FIG. 9b show the Franz diffusion cell, consisting of two Teflon chambers of 1.5 ml volume each, used in the diffusion tests of Rhodamin B through the chitosan foils according to the invention as described above.

FIG. 10 shows the serial overlay of Vis spectra of the acceptor cell content after passing the chitosan foil from experiment J (Table 2).

Figure 11:
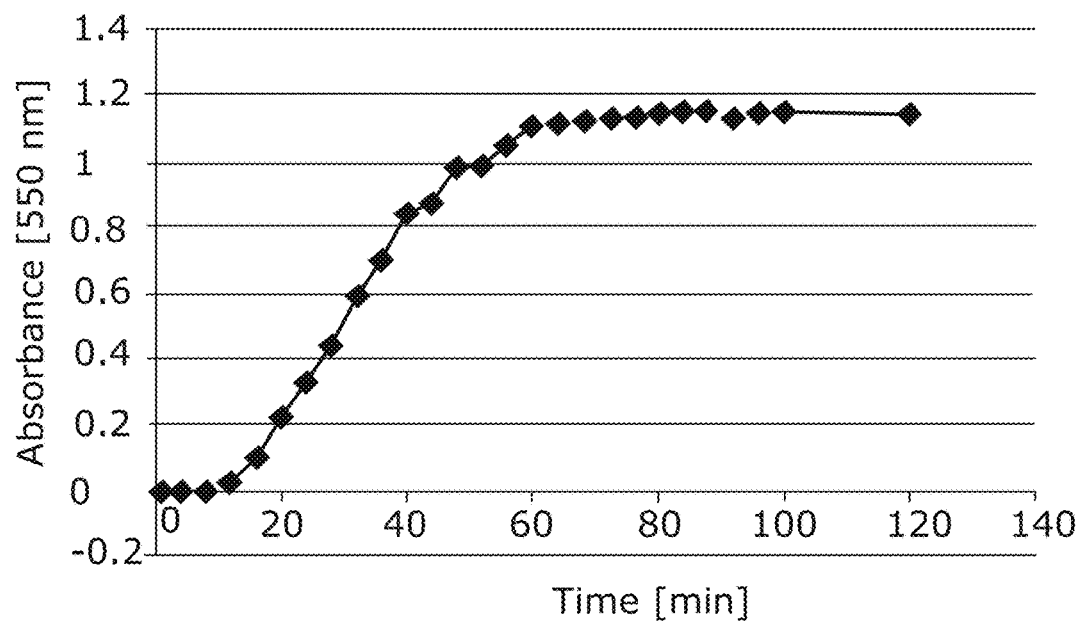
FIG. 11 illustrates the Rhodamin B absorbance at 550 nm as a function of time.

FIG. 11 shows the Rhodamin B absorbance at 550 nm as a function of time. As can be seen, in all cases a logistic increase was observed. The duration of the lag phase is correlated with the foils thickness.

For all graphs regression curves were calculated as well as the linear equations of the tangents at their inflection points. The slopes of these tangents are defined as the corresponding diffusion rates. Table 6 summarizes the results.

TABLE 6

Diffusion rates of Rhodamin B through chitosan foils. The foils from the experiments K and T were fabricated in the presence of polyethylenglycol.

| Foil from experiment | Diffusion rate [$\Delta A_{550}$/min] |
|---|---|
| J | 0.0266 |
| K | 0.0346 |
| Q | 0.0457 |
| T | 0.0530 |

From Table 6 it can be seen that the addition of polyethylenglycol enhances the diffusion rate of the dye through the chitosan foil significantly. This is in line with the results from raster electron microscopies which exhibit a much more porous structure of the foils prepared in the presence of PEG.

Figure 12:
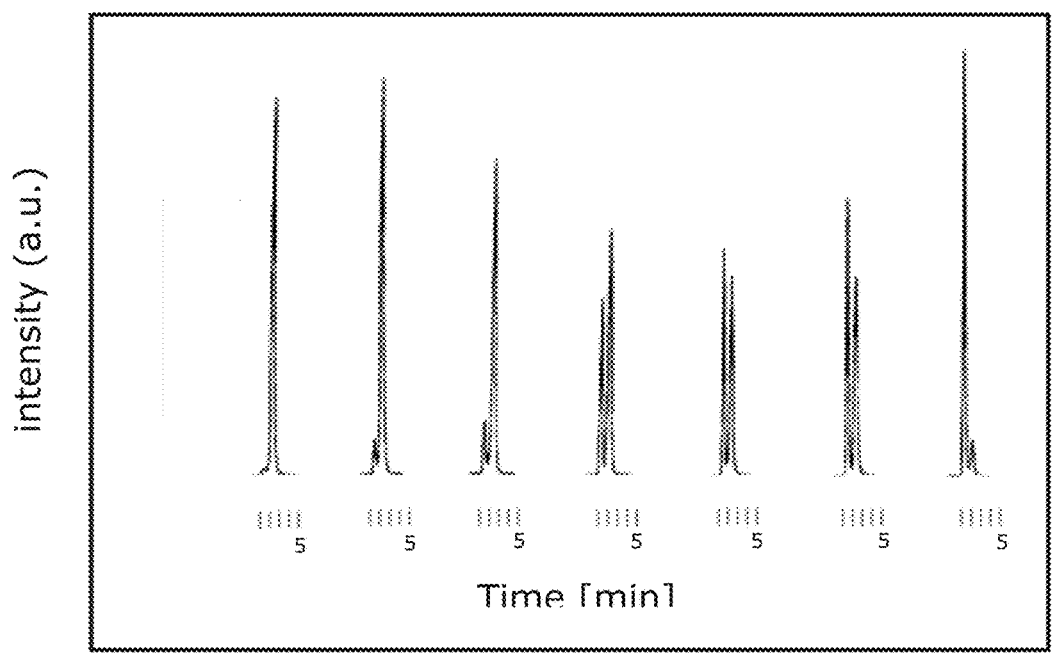
FIG. 12 illustrates the RP-18 HPLC profiles of the hydrolysis reactions of the 28a derivative in aqueous HCl/MeCN 1:1 (v/v)
Figure 13:
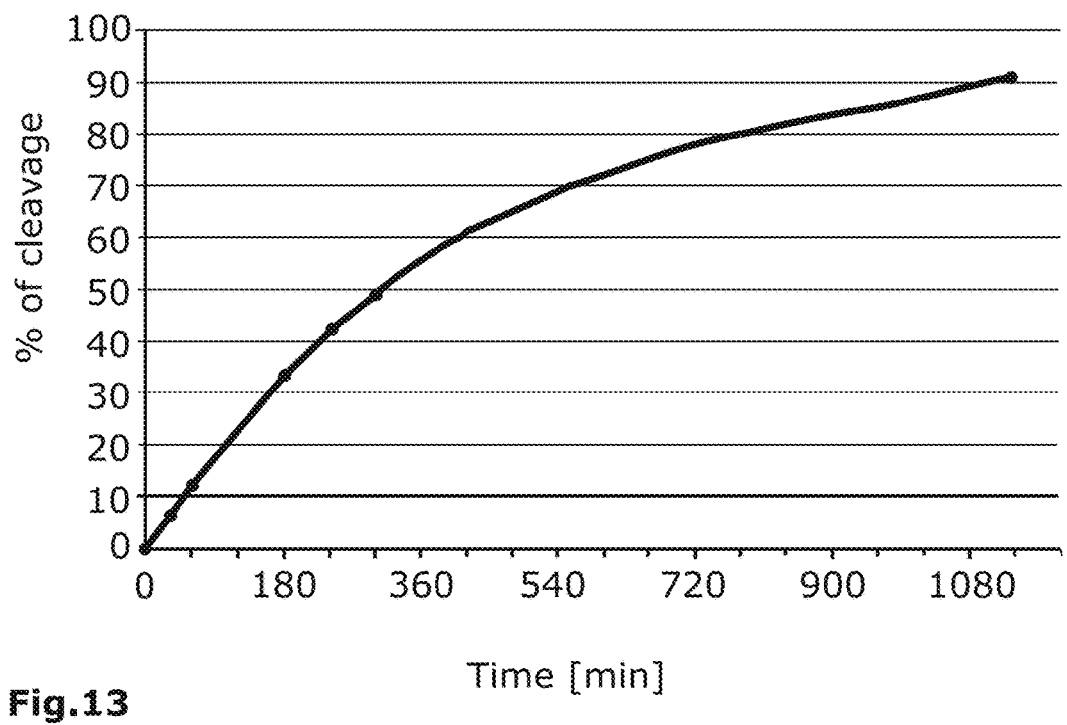
FIG. 13 illustrates a plot of the HPLC measurements of FIG. 12 vs. time.

FIG. 12 shows the RP-18 HPLC profiles of the hydrolysis reactions of 28a in aqueous HCl/MeCN 1:1 (v/v). The faster migrating zone contains always pure 5-fluorouridine, the slower migrating zone the residual ketal 28a. The half-life value was calculated graphically from a plot of the peak integral of both, the residual ketals and 5-fluorouridine vs. reaction time (FIG. 13). Upon acidic hydrolysis only the nucleoside and no 5-fluorouracil were formed.

FIG. 13 shows the plot of the HPLC measurements of FIG. 12 versus time. The half-life value was calculated graphically from the plot. As can be seen, the half-life of the ester 28a under acidic conditions amounts to ≈300 min.

FIG. 14 shows the chitosanase-catalyzed degradation of a 5-FU-chitosan foil-conjugate. The figure displays the absorbance (268 nm) of the acceptor cell content of the diffusion cell (FIG. 5) as a function of time. The arrow indicates the addition of a second chitosanase portion.

As can be seen from FIG. 14, after 4 days the absorbance of the solution in the acceptor chamber became constant. At this time a further aliquot of enzyme suspension (5 µl) was added, upon which the absorbance increased further. This result might be due to a loss of enzyme activity after the long reaction time at 37° C. and/or by a significant product inhibition of the enzyme. After a total degradation time of 240 h both compartments of the diffusion cell show the same absorbance at 268 nm indicating the end of the reaction.

FIG. 15-1 shows a chitosan foil according to the present invention, fabricated from a material with a molecular weight of 20-200 kDa. A qualitative inspection reveals that the foil is relatively tensile and tear-proof and exhibits a low surface roughness.

FIG. 15-2 shows a REM picture of the chitosan foil shown in FIG. 15-1.

FIG. 16 shows the REM picture of a chitosan foil which has been fabricated in the presence of PEG 6000.

The invention claimed is:

1. A compound represented by formula (I)

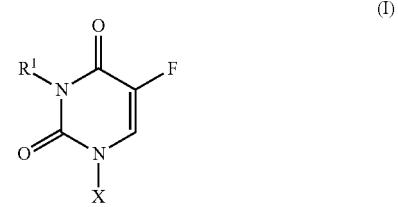

wherein X is

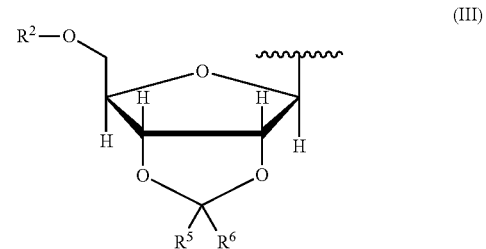

$R^1$ is selected from

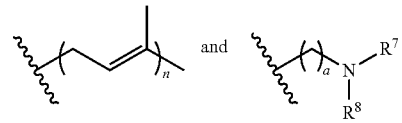

and substituted or unsubstituted cyclic terpene moieties, wherein the substituted or unsubstituted terpene moieties are selected from the group consisting of geranyl, farnesyl, neryl, and phythyl, $R^7$ and $R^8$ are independently selected from $C_1$ to $C_{30}$ alkyl, n is an integer ranging 1 to 4; and a is an integer ranging from 1 to 20;

$R^2$ is H;

$R^5$ and $R^6$ form a ring having at least 5 members, wherein the ring may be substituted or interrupted by one or more hetero atom(s) and/or functional group(s);

with the proviso that $R^1$ and $R^2$ are not both H and with the proviso that the compound comprises at least two chains each of which having 4 or more carbon atoms.

2. A pharmaceutical composition comprising the compound of claim 1 in combination with a pharmaceutically acceptable carrier.

3. A method of treating human colon carcinoma cancer, the method comprising administering the pharmaceutical composition of claim 2 to a patient.

4. A process for preparing the compound according to claim 1, the process comprising the following steps:

a) providing a compound of formula (IA) and introducing protecting groups for hydroxyl groups

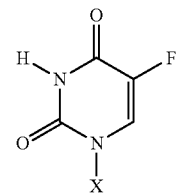

(IA)

b) coupling an alcohol of the formula $R^1$—OH in a Mitsunobu type reaction with the compound (IA) to produce a hydroxyl protected analog of compound (I) and c) optionally, removing the protecting groups for hydroxyl groups.

5. The process according to claim 4, wherein $R^1$—OH is selected from the group consisting of nerol, phythol, abietol, eicosapentaenol and docosahexaenol.

* * * * *